(12) United States Patent
Nomura et al.

(10) Patent No.: US 8,906,518 B2
(45) Date of Patent: Dec. 9, 2014

(54) TRIAZOLE DERIVATIVE, LIGHT-EMITTING ELEMENT, LIGHT-EMITTING DEVICE, AND ELECTRONIC DEVICE

(75) Inventors: Hiroko Nomura, Kanagawa (JP);
Sachiko Kawakami, Kanagawa (JP);
Nobuharu Ohsawa, Kanagawa (JP);
Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 154 days.

(21) Appl. No.: 12/332,970

(22) Filed: Dec. 11, 2008

(65) Prior Publication Data
US 2009/0160324 A1 Jun. 25, 2009

(30) Foreign Application Priority Data
Dec. 21, 2007 (JP) .................................. 2007-330608

(51) Int. Cl.
| H01L 51/50 | (2006.01) |
| C09K 11/06 | (2006.01) |
| C07D 249/08 | (2006.01) |
| C07D 209/42 | (2006.01) |
| C07D 401/14 | (2006.01) |
| C07D 403/14 | (2006.01) |
| C07D 403/12 | (2006.01) |
| H01L 51/00 | (2006.01) |

(52) U.S. Cl.
CPC ............. *C09K 11/06* (2013.01); *H01L 51/0085* (2013.01); *C07D 209/42* (2013.01); *C09K 2211/1022* (2013.01); *H01L 51/5012* (2013.01); *H01L 2251/308* (2013.01); *C07D 249/08* (2013.01); *C09K 2211/1007* (2013.01); *C07D 401/14* (2013.01); *C09K 2211/1029* (2013.01); *H01L 51/0072* (2013.01); *H01L 51/0067* (2013.01); *C07D 403/14* (2013.01); *C09K 2211/1059* (2013.01); *H01L 51/5016* (2013.01); *C07D 403/12* (2013.01); *H01L 51/0061* (2013.01); *Y10S 428/917* (2013.01)
USPC .......... 428/690; 428/917; 257/40; 548/266.4; 313/504

(58) Field of Classification Search
None
See application file for complete search history.

(56) References Cited

U.S. PATENT DOCUMENTS

| 5,834,130 | A | * | 11/1998 | Kido ............................ 428/690 |
| 5,869,199 | A | | 2/1999 | Kido |
| 6,541,129 | B1 | | 4/2003 | Kawamura et al. |
| 7,399,537 | B2 | | 7/2008 | Kawamura et al. |
| 8,178,217 | B2 | | 5/2012 | Nomura et al. |
| 8,389,735 | B2 | * | 3/2013 | Murata et al. .................. 548/145 |
| 2002/0136924 | A1 | | 9/2002 | Higashi et al. |
| 2002/0182441 | A1 | | 12/2002 | Lamansky et al. |
| 2003/0143430 | A1 | | 7/2003 | Kawamura et al. |
| 2004/0110031 | A1 | * | 6/2004 | Fukuda et al. .................. 428/690 |
| 2004/0115476 | A1 | | 6/2004 | Oshiyama et al. |
| 2005/0031899 | A1 | | 2/2005 | Nomura et al. |
| 2005/0048310 | A1 | | 3/2005 | Cocchi et al. |
| 2006/0263636 | A1 | * | 11/2006 | Ohsawa et al. ............... 428/690 |
| 2007/0149784 | A1 | * | 6/2007 | Murata et al. .................. 548/143 |
| 2007/0222376 | A1 | | 9/2007 | Ohsawa et al. |
| 2008/0241591 | A1 | | 10/2008 | Kawamura et al. |
| 2008/0286607 | A1 | | 11/2008 | Nomura et al. |
| 2009/0102361 | A1 | * | 4/2009 | Miki et al. .................... 313/504 |
| 2012/0199818 | A1 | | 8/2012 | Nomura et al. |

FOREIGN PATENT DOCUMENTS

| EP | 1 029 909 A1 | 8/2000 |
| JP | 2000-68059 | 3/2000 |
| JP | 2000-309566 A | 11/2000 |
| JP | 2002-352957 | 12/2002 |
| JP | 2003-7467 | 1/2003 |
| JP | 2004-14440 | 1/2004 |
| JP | 2004-71380 | 3/2004 |
| JP | 2004-111134 A | 4/2004 |
| JP | 2004-152527 | 5/2004 |
| JP | 2004-214050 | 7/2004 |
| JP | 2004-220931 | 8/2004 |
| JP | 2004-253298 | 9/2004 |
| JP | 2007-197429 | 8/2007 |
| JP | 2007-287676 A | 11/2007 |
| WO | WO 03/007394 A2 | 1/2003 |
| WO | WO 2007020881 A1 * | 2/2007 |
| WO | WO 2007026847 A1 * | 3/2007 |
| WO | WO 2007/074893 A1 | 7/2007 |

OTHER PUBLICATIONS

Hughes et al. J. Mater. Chem. 2005, 15, 94-107. Date of online publication: Nov. 18, 2004.*
Kim et al. Synthetic Metals 2007, 157, 743-750. Date of online publication: Sep. 17, 2007.*
Remmers et al. "The Optical, Electronic, and Electroluminescent Properties of Novel Poly(p-phenylene)-Related Polymers" Macromolecules 1996, 29, 7432-7445. Year of publication: 1996.*
International Search Report re application No. PCT/JP2008/072226, dated Jan. 6, 2009.
Written Opinion re application No. PCT/JP2008/072226, dated Jan. 6, 2009.
Search Report re European Application No. EP 08864807.6, dated Apr. 4, 2011.

* cited by examiner

*Primary Examiner* — Andrew K Bohaty
(74) *Attorney, Agent, or Firm* — Husch Blackwell LLP

(57) ABSTRACT

A substance having high excitation energy is provided. In particular, a substance having high triplet excitation energy is provided. Further, a light-emitting element, a light-emitting device, and an electronic device each having high emission efficiency and low driving voltage are provided. A triazole derivative to which an amino group is bonded is provided. In addition, a light-emitting element, a light-emitting device, and an electronic device each including the triazole derivative to which the amino group is bonded are provided.

12 Claims, 23 Drawing Sheets

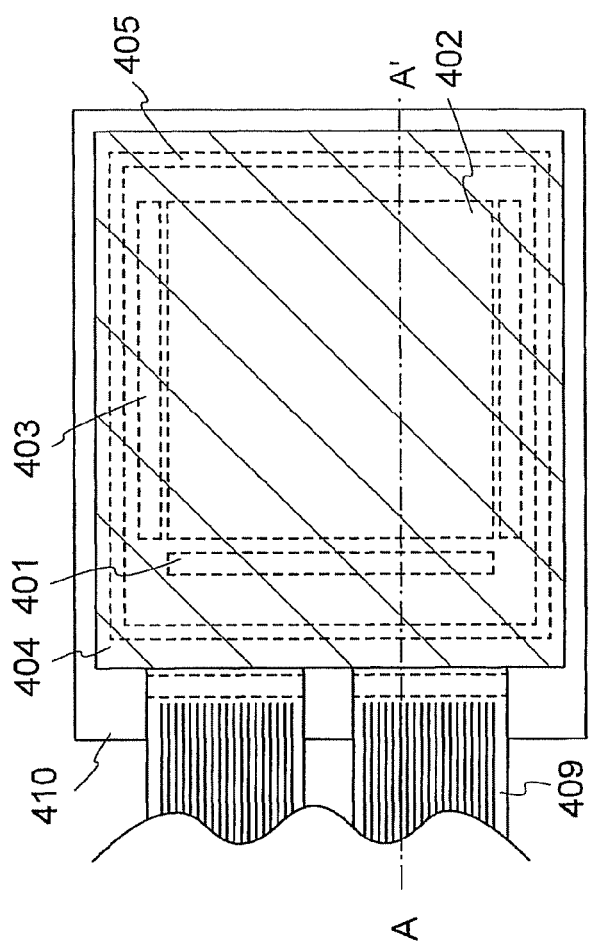
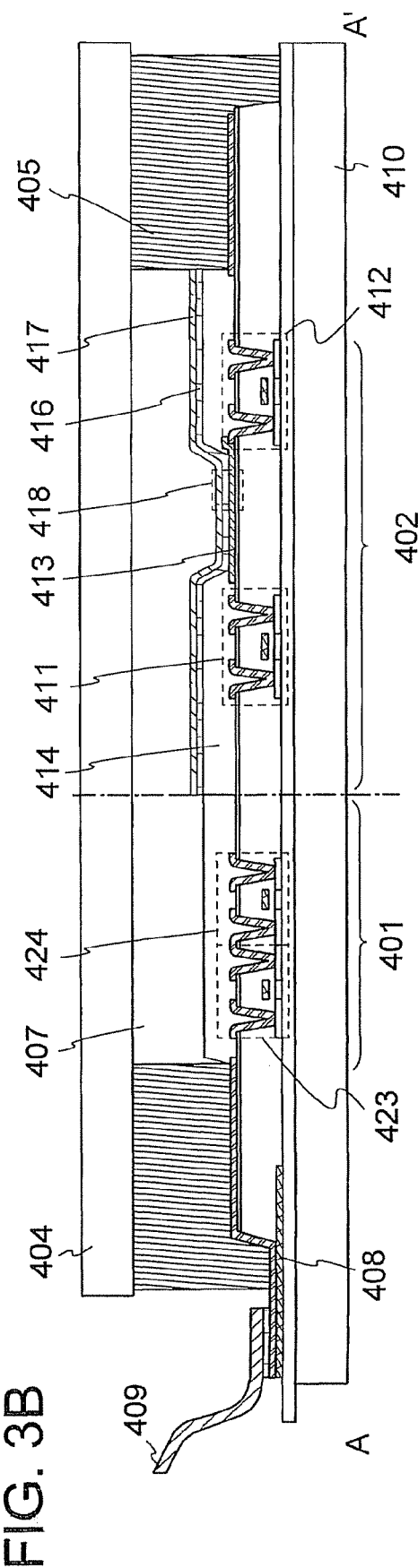
FIG. 3A
FIG. 3B

TRIAZOLE DERIVATIVE, LIGHT-EMITTING ELEMENT, LIGHT-EMITTING DEVICE, AND ELECTRONIC DEVICE

TECHNICAL FIELD

The present invention relates to a light-emitting material applicable to a light-emitting element utilizing electroluminescence. Further, the present invention relates to a light-emitting element using the light-emitting material and to a light-emitting device and an electronic device each using the light-emitting element.

BACKGROUND ART

There is a greater variety in types of organic compounds compared to inorganic compounds, and materials that have a variety of different functions can be designed and synthesized. Because of such advantages, attention has been focused on electronics devices in which organic compounds are used in recent years. For example, solar cells, light-emitting elements, transistors, and the like in which organic compounds are used as functional materials are some typical examples of these electronics devices.

These electronics devices are devices that use the electrical properties and optical properties of organic compounds; of these devices, in particular, research and development of light-emitting elements in which organic compounds are used as light-emitting substances has been showing an impressive amount of progress.

The structure of these light-emitting elements is a simple structure in which only a light-emitting layer that contains an organic compound, which is a light-emitting substance, is provided between electrodes, and these light-emitting elements have been attracting attention as elements of next-generation flat panel display panels because of their characteristics such as a thin shape, lightweight, high response speed, and low voltage driving. Furthermore, displays in which these light-emitting elements are used also have the characteristics such as superior contrast and image quality and a wide viewing angle.

The light-emitting mechanism of the light-emitting elements in which organic compounds are used as light-emitting substances is carrier injection. In other words, by application of a voltage to a light-emitting layer interposed between electrodes, holes and electrons injected from the electrodes recombine to place the light-emitting substance into an excited state, and the light-emitting substance emits light when the light-emitting substance returns to the ground state from the excited state. Further, as the types of excited states, there can be a singlet excited state (S*) and a triplet excited state (T*). Furthermore, it is thought that the ratio of S* to T* in a light-emitting element is statistically 1:3.

At room temperature, a compound that converts a singlet excited state into luminescence (hereinafter referred to as a fluorescent compound) exhibits only luminescence from a singlet excited state (fluorescence), not luminescence from a triplet excited state (phosphorescence). Therefore, the internal quantum efficiency (the ratio of generated photons to injected carriers) of a light-emitting element using a fluorescent compound is thought to have a theoretical limit of 25% on the basis that S*:T*=1:3.

On the other hand, by using a compound that converts a triplet excited state into luminescence (hereinafter referred to as a phosphorescent compound), internal quantum efficiency can be improved from 75% to 100% theoretically. That is, emission efficiency can be three to four times as high as that of a fluorescent compound. From such a reason, in order to achieve a light-emitting element with high efficiency, a light-emitting element using a phosphorescent compound has been actively developed recently.

When a light-emitting layer of a light-emitting element is formed using a phosphorescent compound as described above, in order to suppress concentration quenching of the phosphorescent compound or quenching due to triplet-triplet annihilation, the light-emitting layer is often formed so that the phosphorescent compound is dispersed in a matrix formed of another substance. In that case, a substance serving as a matrix is referred to as a host material, a substance that is dispersed in a matrix, such as a phosphorescent compound, is referred to as a guest material.

When a phosphorescent compound is used as a guest material, a host material is needed to have triplet excitation energy (an energy difference between a ground state and a triplet excited state) higher than that of the phosphorescent compound. In Patent Document 1 (Japanese Published Patent Application No. 2002-352957), TAZ is used as a host material of a phosphorescent compound which emits green light.

However, there has been a problem in that TAZ has difficulty in accepting holes in exchange for having high triplet excitation energy and accordingly driving voltage increases. Therefore, a substance that has high triplet excitation energy and also can easily accept or transport both holes and electrons (i.e. a bipolar substance) is required as a host material for a phosphorescent compound.

Furthermore, because singlet excitation energy (the difference in energy between a ground state and a singlet excited state) is greater than triplet excitation energy, a material that has high triplet excitation energy will also have high singlet excitation energy. Consequently, a substance that has high triplet excitation energy is also useful in a light-emitting element formed using a fluorescent compound as a light-emitting substance.

DISCLOSURE OF INVENTION

In view of the foregoing problem, the present invention provides a substance having high excitation energy, in particular, a substance having high triplet excitation energy. Further, the present invention provides a bipolar substance.

Further, the present invention improves emission efficiency of a light-emitting element.

Furthermore, the present invention reduces driving voltage of a light-emitting element.

Moreover, the present invention reduces power consumption of a light-emitting element, a light-emitting device, or an electronic device.

As a result of intense study, the present inventors have found that the above problem can be solved by a certain triazole derivative. In other words, one aspect of the present invention is a triazole derivative in which an amino group represented by a general formula (G2) is bonded to any one of $Ar^1$ to $Ar^3$ of a triazole derivative represented by a general formula (G1) below.

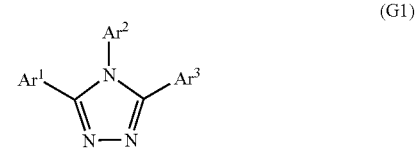

(G1)

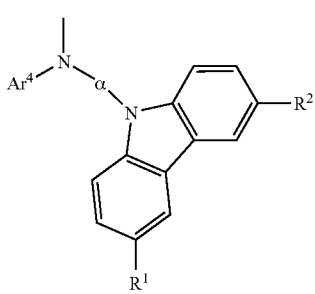

In the above general formula (G1), $Ar^1$ to $Ar^3$ individually represent an aryl group having 6 to 25 carbon atoms or a heteroaryl group having 3 to 9 carbon atoms. In the above general formula (G2), $Ar^4$ represents an aryl group having 6 to 25 carbon atoms, α represents an arylene group having 6 to 25 carbon atoms, and $R^1$ and $R^2$ individually represent hydrogen, an alkyl group having 1 to 4 carbon atoms, an aryl group having 6 to 25 carbon atoms, or an alkoxy group having 1 to 4 carbon atoms.

Further, an aspect of the present invention is a triazole derivative represented by a general formula (G3).

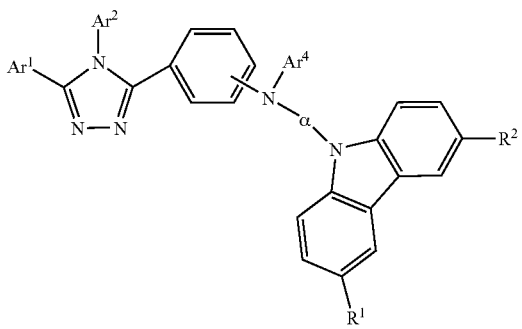

In the above general formula (G3), $Ar^1$ and $Ar^2$ individually represent an aryl group having 6 to 25 carbon atoms or a heteroaryl group having 3 to 9 carbon atoms, $Ar^4$ represents an aryl group having 6 to 25 carbon atoms, α represents an arylene group having 6 to 25 carbon atoms, and $R^1$ and $R^2$ individually represent hydrogen, an alkyl group having 1 to 4 carbon atoms, an aryl group having 6 to 25 carbon atoms, or an alkoxy group having 1 to 4 carbon atoms.

Further, an aspect of the present invention is a triazole derivative represented by a general formula (G4) below.

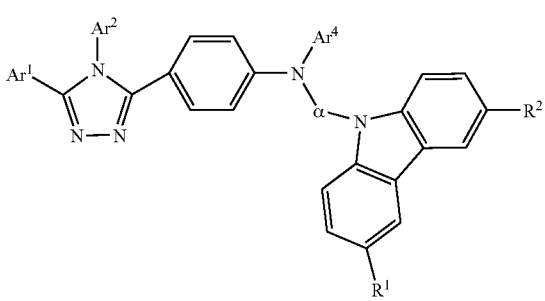

In the above general formula (G4), $Ar^1$ and $Ar^2$ individually represent an aryl group having 6 to 25 carbon atoms or a heteroaryl group having 3 to 9 carbon atoms, $Ar^4$ represents an aryl group having 6 to 25 carbon atoms, α represents an arylene group having 6 to 25 carbon atoms, and $R^1$ and $R^2$ individually represent hydrogen, an alkyl group having 1 to 4 carbon atoms, an aryl group having 6 to 25 carbon atoms, or an alkoxy group having 1 to 4 carbon atoms.

Further, an aspect of the present invention is a triazole derivative represented by a general formula (G5) below.

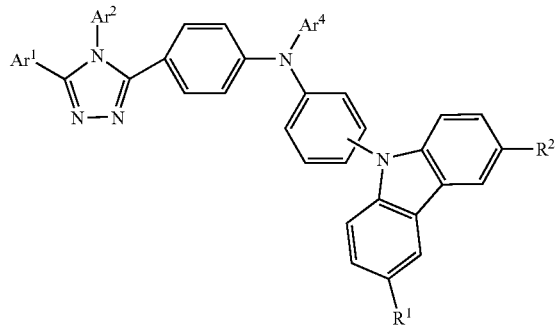

In the above general formula (G5), $Ar^1$ and $Ar^2$ individually represent an aryl group having 6 to 25 carbon atoms or a heteroaryl group having 3 to 9 carbon atoms, $Ar^4$ represents an aryl group having 6 to 25 carbon atoms, and $R^1$ and $R^2$ individually represent hydrogen, an alkyl group having 1 to 4 carbon atoms, an aryl group having 6 to 25 carbon atoms, or an alkoxy group having 1 to 4 carbon atoms.

Further, an aspect of the present invention is a triazole derivative represented by a general formula (G6) below.

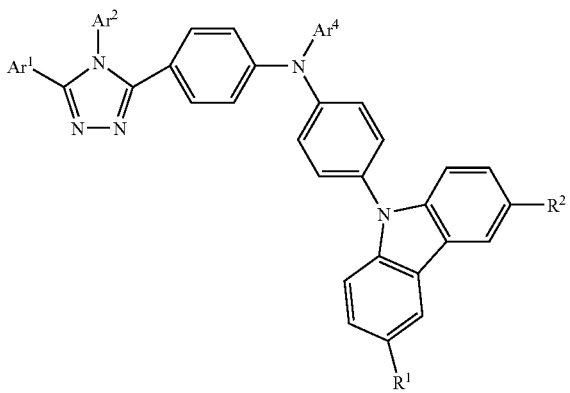

In the above general formula (G6), $Ar^1$ and $Ar^2$ individually represent an aryl group having 6 to 25 carbon atoms or a heteroaryl group having 3 to 9 carbon atoms, $Ar^4$ represents an aryl group having 6 to 25 carbon atoms, and $R^1$ and $R^2$ individually represent hydrogen, an alkyl group having 1 to 4 carbon atoms, an aryl group having 6 to 25 carbon atoms, or an alkoxy group having 1 to 4 carbon atoms.

Further, an aspect of the present invention is a triazole derivative represented by a general formula (G7) below.

Further, an aspect of the present invention is a triazole derivative represented by a general formula (G9) below.

(G7)

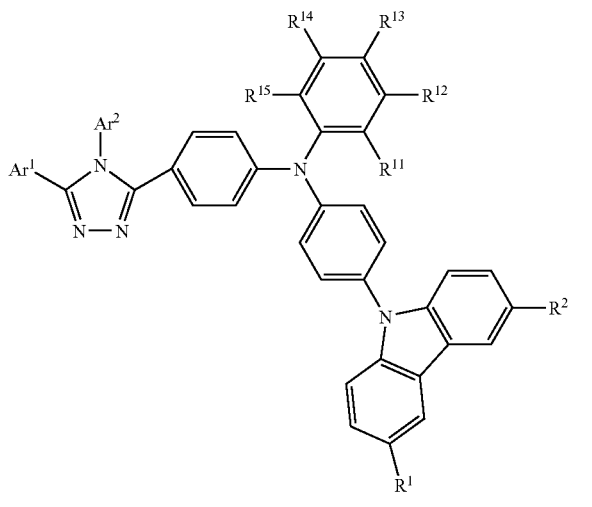

(G9)

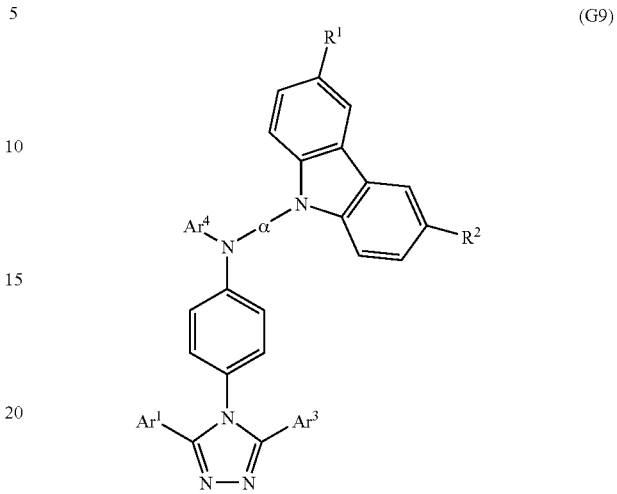

In the above general formula (G7), $Ar^1$ and $Ar^2$ individually represent an aryl group having 6 to 25 carbon atoms or a heteroaryl group having 3 to 9 carbon atoms, $R^1$ and $R^2$ individually represent hydrogen, an alkyl group having 1 to 4 carbon atoms, an aryl group having 6 to 25 carbon atoms, or an alkoxy group having 1 to 4 carbon atoms, and $R^{11}$ to $R^{15}$ individually represent any of hydrogen, an alkyl group having 1 to 4 carbon atoms, or a phenyl group.

In any of the above-described structures, it is preferable that $Ar^1$ and $Ar^2$ be individually a phenyl group or a pyridyl group.

Further, an aspect of the present invention is a triazole derivative represented by a general formula (G8) below.

In the above general formula (G9), $Ar^1$ and $Ar^3$ individually represent an aryl group having 6 to 25 carbon atoms or a heteroaryl group having 3 to 9 carbon atoms, $Ar^4$ represents an aryl group having 6 to 25 carbon atoms, α represents an arylene group having 6 to 25 carbon atoms, and $R^1$ and $R^2$ individually represent hydrogen, an alkyl group having 1 to 4 carbon atoms, an aryl group having 6 to 25 carbon atoms, or an alkoxy group having 1 to 4 carbon atoms.

Further, an aspect of the present invention is a triazole derivative represented by a general formula (G10) below.

(G8)

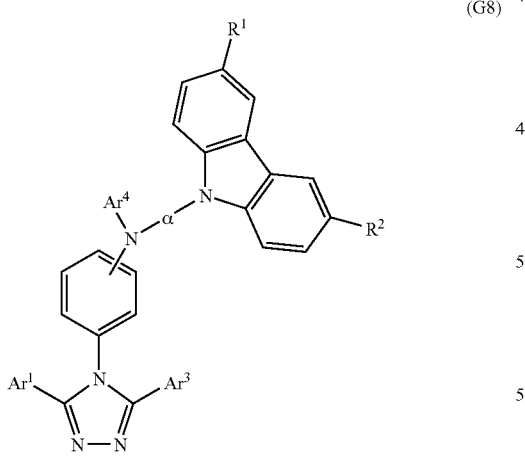

(G10)

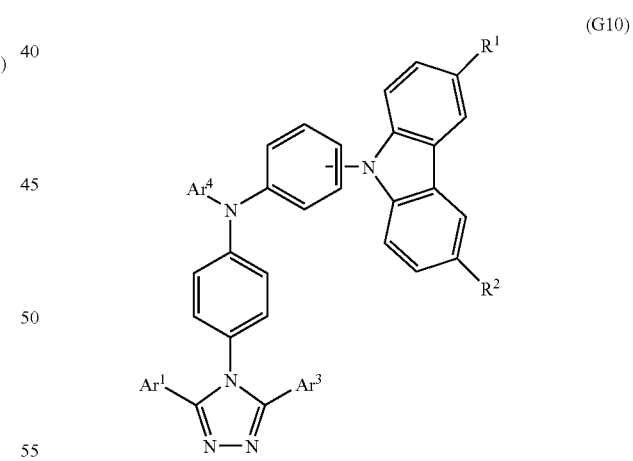

In the above general formula (G8), $Ar^1$ and $Ar^3$ individually represent an aryl group having 6 to 25 carbon atoms or a heteroaryl group having 3 to 9 carbon atoms, $Ar^4$ represents an aryl group having 6 to 25 carbon atoms, α represents an arylene group having 6 to 25 carbon atoms, and $R^1$ and $R^2$ individually represent hydrogen, an alkyl group having 1 to 4 carbon atoms, an aryl group having 6 to 25 carbon atoms, or an alkoxy group having 1 to 4 carbon atoms.

In the above general formula (G10), $Ar^1$ and $Ar^3$ individually represent an aryl group having 6 to 25 carbon atoms or a heteroaryl group having 3 to 9 carbon atoms, $Ar^4$ represents an aryl group having 6 to 25 carbon atoms, and $R^1$ and $R^2$ individually represent hydrogen, an alkyl group having 1 to 4 carbon atoms, an aryl group having 6 to 25 carbon atoms, or an alkoxy group having 1 to 4 carbon atoms.

Further, an aspect of the present invention is a triazole derivative represented by a general formula (G11) below.

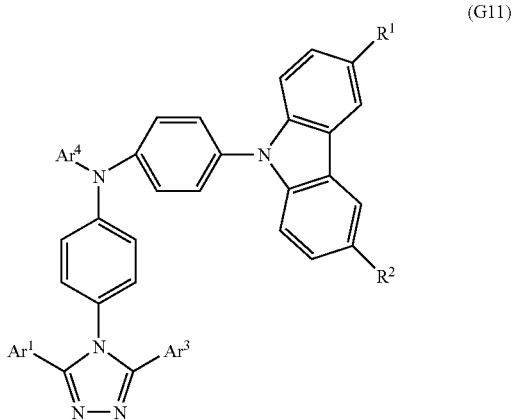

(G11)

In the above general formula (G11), $Ar^1$ and $Ar^3$ individually represent an aryl group having 6 to 25 carbon atoms or a heteroaryl group having 3 to 9 carbon atoms, $Ar^4$ represents an aryl group having 6 to 25 carbon atoms, and $R^1$ and $R^2$ individually represent hydrogen, an alkyl group having 1 to 4 carbon atoms, an aryl group having 6 to 25 carbon atoms, or an alkoxy group having 1 to 4 carbon atoms.

Further, an aspect of the present invention is a triazole derivative represented by a general formula (G12) below.

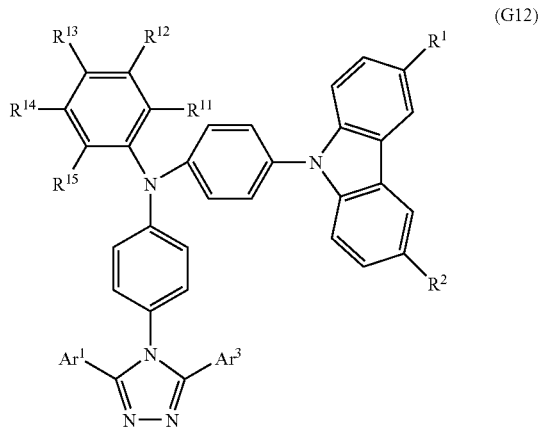

(G12)

In the above general formula (G12), $Ar^1$ and $Ar^1$ individually represent an aryl group having 6 to 25 carbon atoms or a heteroaryl group having 3 to 9 carbon atoms, $R^1$ and $R^2$ individually represent hydrogen, an alkyl group having 1 to 4 carbon atoms, an aryl group having 6 to 25 carbon atoms, or an alkoxy group having 1 to 4 carbon atoms, and $R^{11}$ to $R^{15}$ individually represent any of hydrogen, an alkyl group having 1 to 4 carbon atoms, or a phenyl group.

In any of the above-described structures, it is preferable that $Ar^1$ and $Ar^3$ be individually a phenyl group or a pyridyl group.

Further, an aspect of the present invention is a light-emitting element including the above triazole derivative between a pair of electrodes.

Further, an aspect of the present invention is a light-emitting element including a light-emitting layer between a pair of electrodes, and the light-emitting layer has any triazole derivative described above.

Further, an aspect of the present invention is a light-emitting element including a light-emitting layer between a pair of electrodes, and the light-emitting layer has any triazole derivative described above and a substance that emits phosphorescence.

Further, an aspect of the present invention is a light-emitting device including the above light-emitting element and a control circuit configured to control light emission from the light-emitting element.

Further, an aspect of the present invention is an electronic device including a display portion, and the display portion includes the above light-emitting element and a control circuit configured to control light emission from the light-emitting element.

The category of the light-emitting device of the present invention includes an image display device and a light-emitting device each using a light-emitting element. Further, the category of the light-emitting device of the present invention includes a module in which a connector, for example, an anisotropic conductive film, a tape automated bonding (TAB) tape, or a tape carrier package (TCP) is attached to a light-emitting element, and also a module in which an integrated circuit (IC) is directly mounted on a light-emitting element by a chip on glass (COG) method. Furthermore, the category includes a light-emitting device used for a lightning apparatus and the like.

By implementing the present invention, a substance having high excitation energy, in particular, a substance having high triplet excitation energy can be obtained. Further, a bipolar substance can be obtained.

Moreover, by applying such a substance to a light-emitting element, a light-emitting element having has high emission efficacy can be provided. Further, a light-emitting element with low driving voltage can be provided.

Furthermore, by manufacturing a light-emitting device using the light-emitting element described above, a light-emitting device with less power consumption can be provided. Moreover, by applying such a light-emitting device to an electronic device, an electronic device with less power consumption can be provided.

BRIEF DESCRIPTION OF DRAWINGS

FIGS. 3A and 3B illustrate a light-emitting device according to an aspect of the present invention.

BEST MODE FOR CARRYING OUT THE INVENTION

Figure 1:
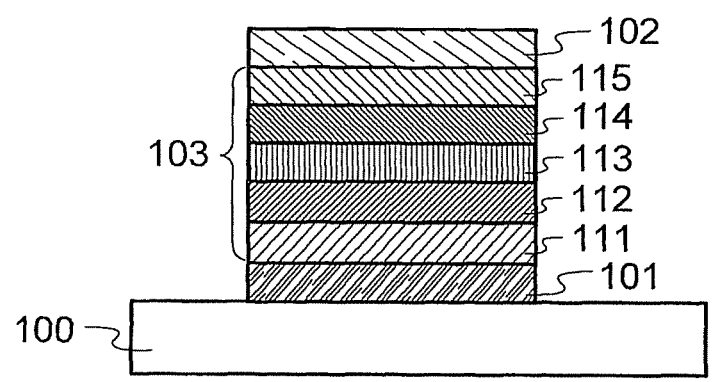
FIG. 1 illustrates a light-emitting element according to an aspect of the present invention.

Hereinafter, embodiment modes of the present invention will be described in detail with reference to the accompanying drawings. Note that the present invention is not limited to the description below, and it is easily understood by those skilled in the art that a variety of changes and modifications can be made without departing from the spirit and scope of the present invention. Therefore, the present invention should not be interpreted as being limited to the content of the embodiment modes described below.

Embodiment Mode 1

In Embodiment Mode 1, a triazole derivative of the present invention is described.

The triazole derivative of the present invention includes, in one molecule, a triazole skeleton having an electron-transporting property and high triplet excitation energy, and an amine skeleton having a hole-transporting property.

Specifically, the triazole derivative of the present invention is a triazole derivative that is a 1,2,4-triazole derivative, in which an aryl group or a heteroaryl group is bonded to each of the 3-, 4-, and 5-positions of triazole and an amino group is included in any one of the aryl group or the heteroaryl group.

In other words, the triazole derivative of the present invention is a triazole derivative in which the secondary amine represented by the general formula (G2) is bonded to any one of $Ar^1$ to $Ar^3$ of the triazole derivative represented by the general formula (G1).

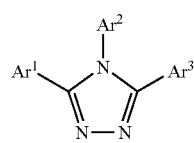

(G1)

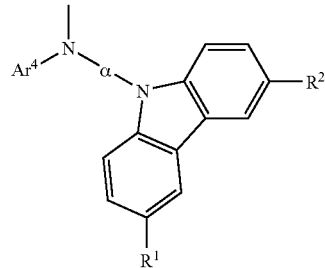

(G2)

In the above general formulae (G1) and (G2), $Ar^1$ to $Ar^3$ individually represent an aryl group having 6 to 25 carbon atoms or a heteroaryl group having 3 to 9 carbon atoms, α represents an arylene group having 6 to 25 carbon atoms, and $R^1$ and $R^2$ individually represent hydrogen, an aryl group having 6 to 25 carbon atoms, an alkyl group having 1 to 4 carbon atoms, or an alkoxy group having 1 to 4 carbon atoms.

In other words, there are two main types of triazole derivative of the present invention: a triazole derivative represented by a general formula (G1') and a triazole derivative represented by a general formula (G1").

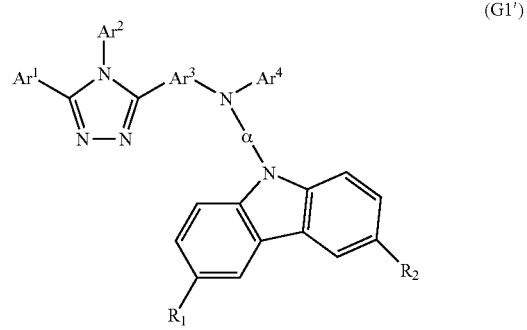

(G1')

In the above general formula (G1'), $Ar^1$ and $Ar^2$ individually represent an aryl group having 6 to 25 carbon atoms or a heteroaryl group having 3 to 9 carbon atoms, $Ar^3$ represents an arylene group having 6 to 25 carbon atoms or a heteroarylene group having 3 to 9 carbon atoms, $Ar^4$ represents an aryl group having 6 to 25 carbon atoms, α represents an arylene group having 6 to 25 carbon atoms, and $R^{11}$ and $R^{12}$ individually represent hydrogen, an aryl group having 6 to 25 carbon atoms, an alkyl group having 1 to 4 carbon atoms, or an alkoxy group having 1 to 4 carbon atoms.

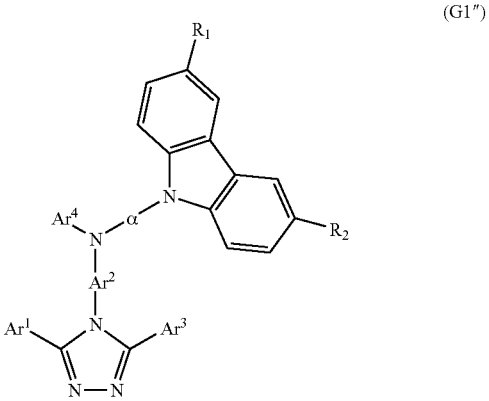

(G1")

In the above general formula (G1"), $Ar^1$ and $Ar^3$ individually represent an aryl group having 6 to 25 carbon atoms or a heteroaryl group having 3 to 9 carbon atoms, $Ar^2$ represents an arylene group having 6 to 25 carbon atoms or a heteroarylene group having 3 to 9 carbon atoms, $Ar^4$ represents an aryl group having 6 to 25 carbon atoms, α represents an arylene group having 6 to 25 carbon atoms, and $R^{11}$ and $R^{12}$ individually represent hydrogen, an aryl group having 6 to 25 carbon atoms, an alkyl group having 1 to 4 carbon atoms, or an alkoxy group having 1 to 4 carbon atoms.

The aryl group may have a substituent. In addition, the aryl group is preferably an aryl group having 6 to 25 carbon atoms for ease of synthesis. For example, there are a phenyl group, an o-tolyl group, a m-tolyl group, a p-tolyl group, a 4-tert-butylphenyl group, a 1-naphthyl group, a 2-naphthyl group, a 2-biphenyl group, a 3-biphenyl group, a 4-biphenylyl group, a 9,9-dimethylfluoren-2-yl group, a spiro-9,9'-bifluoren-2-yl group, and the like. Examples of these substituents are illustrated in structural formulae (1-1) to (1-9).

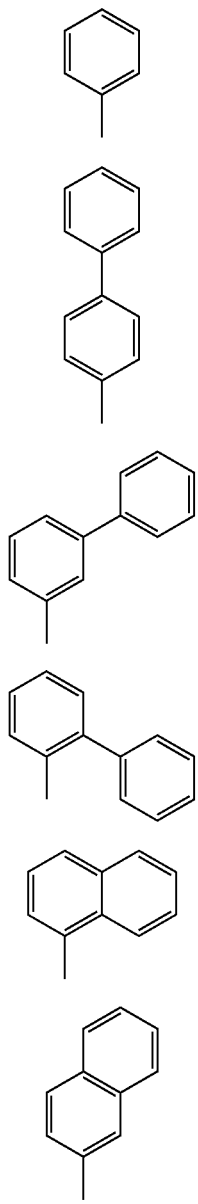

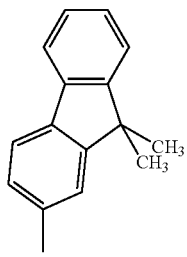

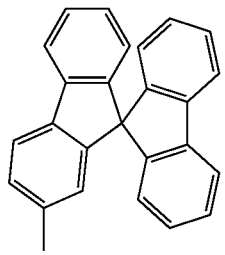

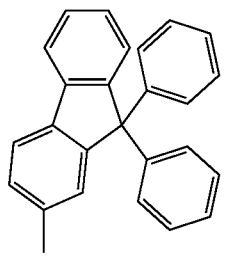

Further, the heteroaryl group may have a substituent. In addition, the heteroaryl group is preferably a heteroaryl group having 3 to 9 carbon atoms for ease of synthesis. For example, there are a 1,3,5-triazin-2-yl group, a 1,2,4-triazin-3-yl group, a pyrimidin-4-yl group, a pyrazin-2-yl group, a 2-pyridyl group, a 3-pyridyl group, a 4-pyridyl group, a quinolyl group, and the like. Examples of these substituents are illustrated in structural formulae (2-1) to (2-14).

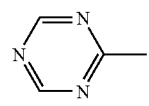

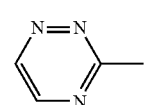

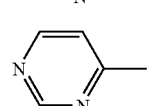

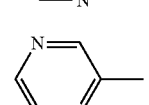

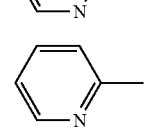

-continued (2-6) 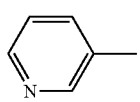

(2-7) 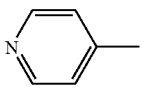

(2-8) 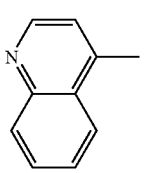

(2-9) 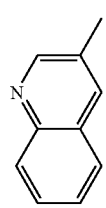

(2-10) 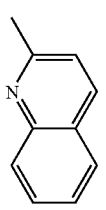

(2-11) 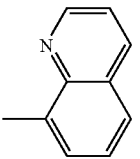

(2-12) 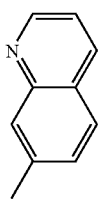

(2-13) 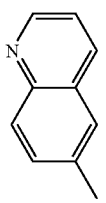

(2-14) 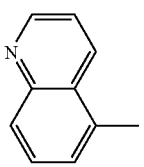

Further, the arylene group may have a substituent. In addition, the arylene group is preferably an arylene group having 6 to 25 carbon atoms for ease of synthesis. For example, there are a 1,2-phenylene group, a 1,3-phenylene group, a 1,4-phenylene group, a 2,5-dimethyl-1,4-phenylene group, a 1,4-naphthylene group, a 1,5-naphthylene group, a 4,4'-biphenylene group, a 9,9-dimethylfluorene-2,7-diyl group, a spiro-9,9'-bifluorene-2,7-diyl group, and the like. Examples of these substituents are illustrated in structural formulae (3-1) to (3-9).

(3-1) 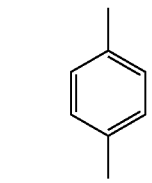

(3-2) 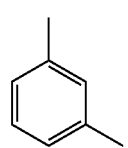

(3-3) 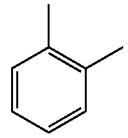

(3-4) 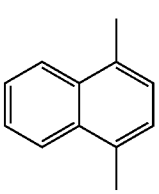

(3-5) 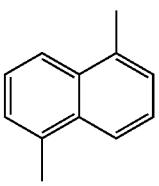

(3-6) 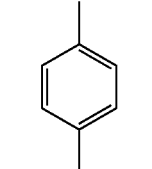

(3-7) 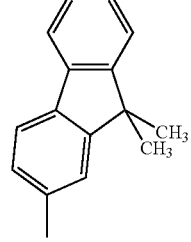

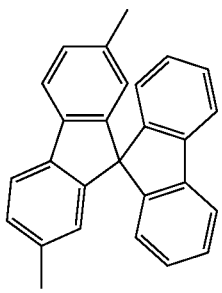

(3-8)

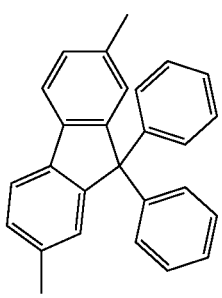

(3-9)

Further, the heteroarylene group may have a substituent. In addition, the heteroarylene group is preferably a heteroarylene group having 3 to 9 carbon atoms for ease of synthesis. For example, there are a pyridine-2,5-diyl group, a pyridine-2,6-diyl group, and the like. Examples of these substituents are illustrated in structural formulae (4-1) to (4-3).

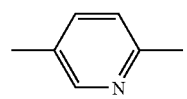

(4-1)

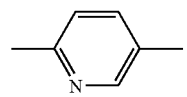

(4-2)

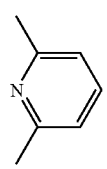

(4-3)

Further, the alkyl group is preferably an alkyl group having 1 to 4 carbon atoms for ease of synthesis. As an alkyl group having 1 to 4 carbon atoms, for example, there are a methyl group, an ethyl group, an isopropyl group, an n-propyl group, an isobutyl group, a sec-butyl group, an n-butyl group, a tert-butyl group, and the like.

Further, the alkoxy group is preferably an alkoxy group having 1 to 4 carbon atoms for ease of synthesis. As an alkoxy group having 1 to 4 carbon atoms, for example, there are a methoxy group, an ethoxy group, an isopropoxy group, an isobutoxy group, a tert-butoxy group, and the like.

The triazole derivative represented by the general formula (G1') is preferably a triazole derivative represented by a general formula (G3) for ease of synthesis.

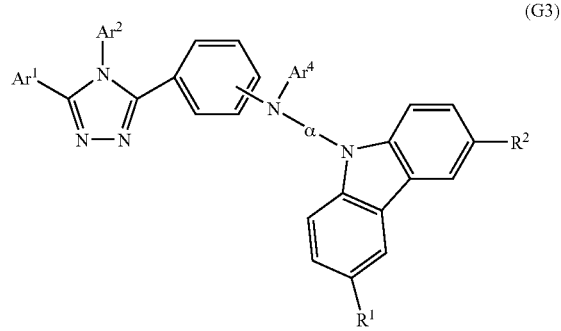

(G3)

In the general formula (G3), $Ar^1$ and $Ar^2$ individually represent an aryl group having 6 to 25 carbon atoms or a heteroaryl group having 3 to 9 carbon atoms, $Ar^4$ represents an aryl group having 6 to 25 carbon atoms, α represents an arylene group having 6 to 25 carbon atoms, and $R^{11}$ and $R^{12}$ individually represent hydrogen, an aryl group having 6 to 25 carbon atoms, an alkyl group having 1 to 4 carbon atoms, or an alkoxy group having 1 to 4 carbon atoms.

As the triazole derivative represented by the general formula (G3), the triazole derivative represented by the general formula (G4) is preferable because the steric hindrance is reduced and thus synthesis is facilitated.

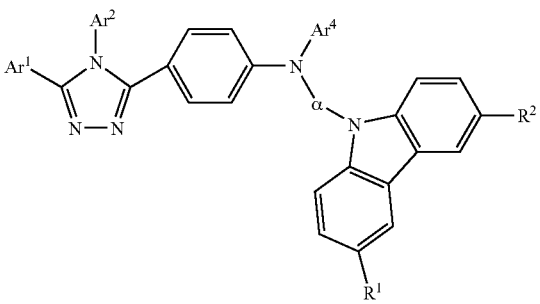

(G4)

In the general formula (G4), $Ar^1$ and $Ar^2$ individually represent an aryl group having 6 to 25 carbon atoms or a heteroaryl group having 3 to 9 carbon atoms, $Ar^4$ represents an aryl group having 6 to 25 carbon atoms, α represents an arylene group having 6 to 25 carbon atoms, and $R^{11}$ and $R^{12}$ individually represent hydrogen, an aryl group having 6 to 25 carbon atoms, an alkyl group having 1 to 4 carbon atoms, or an alkoxy group having 1 to 4 carbon atoms.

As the triazole derivative represented by the general formula (G4), the triazole derivative represented by the general formula (G5) is preferable because the steric hindrance is reduced and thus synthesis is facilitated.

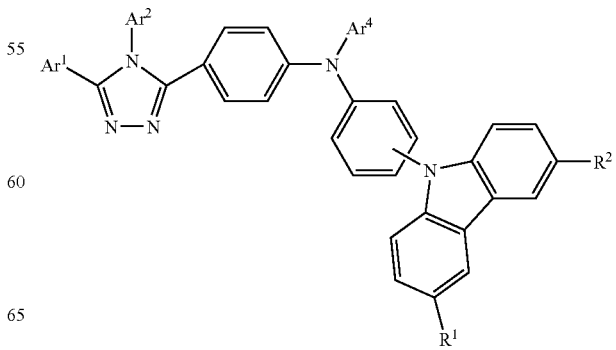

(G5)

In the general formula (G5), $Ar^1$ and $Ar^2$ individually represent an aryl group having 6 to 25 carbon atoms or a heteroaryl group having 3 to 9 carbon atoms, $Ar^4$ represents an aryl group having 6 to 25 carbon atoms, and $R^{11}$ and $R^{12}$ individually represent hydrogen, an aryl group having 6 to 25 carbon atoms, an alkyl group having 1 to 4 carbon atoms, or an alkoxy group having 1 to 4 carbon atoms.

As the triazole derivative represented by the general formula (G5), the triazole derivative represented by the general formula (G6) is preferable because the steric hindrance is reduced and thus synthesis is facilitated.

(G6)

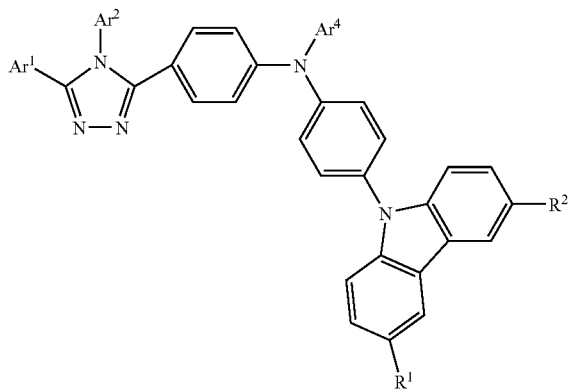

In the general formula (G6), $Ar^1$ and $Ar^2$ individually represent an aryl group having 6 to 25 carbon atoms or a heteroaryl group having 3 to 9 carbon atoms, $Ar^4$ represents an aryl group having 6 to 25 carbon atoms, and $R^{11}$ and $R^{12}$ individually represent hydrogen, an aryl group having 6 to 25 carbon atoms, an alkyl group having 1 to 4 carbon atoms, or an alkoxy group having 1 to 4 carbon atoms.

As the triazole derivative represented by the general formula (G6), the triazole derivative represented by the general formula (G7) is preferable because the steric hindrance is reduced and thus synthesis is facilitated.

(G7)

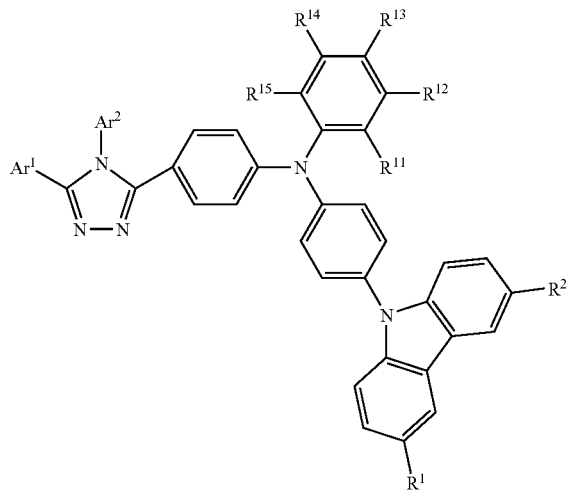

In the general formula (G7), $Ar^1$ and $Ar^2$ individually represent an aryl group having 6 to 25 carbon atoms or a heteroaryl group having 3 to 9 carbon atoms, and $R^{11}$ and $R^{12}$ individually represent hydrogen, an aryl group having 6 to 25 carbon atoms, an alkyl group having 1 to 4 carbon atoms, or an alkoxy group having 1 to 4 carbon atoms.

In the general formulae (G1') and (G3) to (G7), for ease of synthesis, it is preferable that $Ar^1$ and $Ar^2$ be individually a phenyl group or a pyridyl group. Further, because of the high triplet excitation energy, it is preferable that $Ar^1$ and $Ar^2$ be individually a phenyl group or a pyridyl group. In particular, a pyridyl group is preferable. By adopting a pyridyl group, the electron-transporting property of the triazole derivative increases to improve carrier balance; accordingly, the triazole derivative can be preferably used for a light-emitting element. Since the balance between injected electrons and holes is important particularly for a light-emitting layer of a light-emitting element, the triazole derivative of the present invention is more preferably used for a light-emitting layer.

A triazole derivative represented by a general formula (G1'') is preferably the triazole derivative represented by the general formula (G8) for ease of synthesis.

(G8)

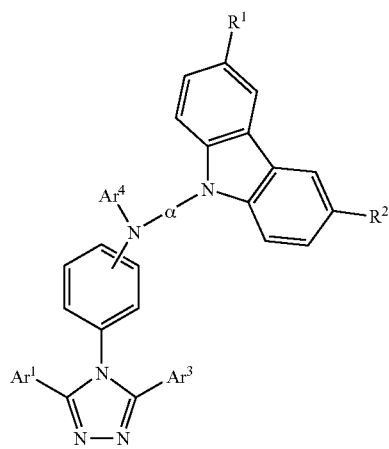

In the general formula (G8), $Ar^1$ and $Ar^3$ individually represent an aryl group having 6 to 25 carbon atoms or a heteroaryl group having 3 to 9 carbon atoms, $Ar^4$ represents an aryl group having 6 to 25 carbon atoms, α represents an arylene group having 6 to 25 carbon atoms, and $R^{11}$ and $R^{12}$ individually represent hydrogen, an aryl group having 6 to 25 carbon atoms, an alkyl group having 1 to 4 carbon atoms, or an alkoxy group having 1 to 4 carbon atoms.

As the general formula (G8), the triazole derivative represented by the general formula (G9) is preferable because the steric hindrance is reduced and thus synthesis is facilitated.

(G9)

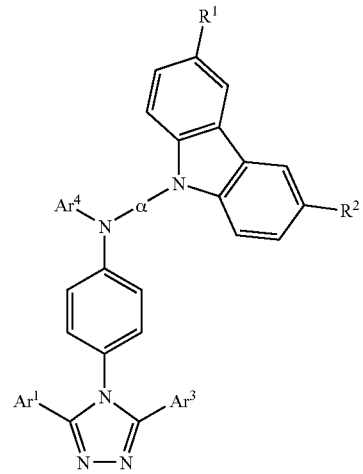

In the general formula (G9), $Ar^1$ and $Ar^3$ individually represent an aryl group having 6 to 25 carbon atoms or a heteroaryl group having 3 to 9 carbon atoms, $Ar^4$ represents an aryl group having 6 to 25 carbon atoms, α represents an arylene group having 6 to 25 carbon atoms, and $R^{11}$ and $R^{12}$ individually represent hydrogen, an aryl group having 6 to 25 carbon atoms, an alkyl group having 1 to 4 carbon atoms, or an alkoxy group having 1 to 4 carbon atoms.

As the triazole derivative represented by the general formula (G9), the triazole derivative represented by the general formula (G10) is preferable because the steric hindrance is reduced and thus synthesis is facilitated.

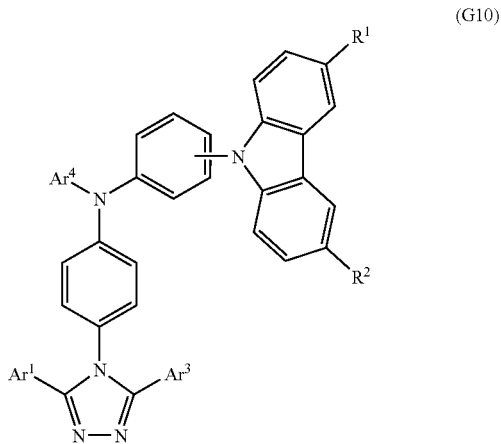

(G10)

In the general formula (G10), $Ar^1$ and $Ar^3$ individually represent an aryl group having 6 to 25 carbon atoms or a heteroaryl group having 3 to 9 carbon atoms, $Ar^4$ represents an aryl group having 6 to 25 carbon atoms, and $R^{11}$ and $R^{12}$ individually represent hydrogen, an aryl group having 6 to 25 carbon atoms, an alkyl group having 1 to 4 carbon atoms, or an alkoxy group having 1 to 4 carbon atoms.

As the triazole derivative represented by the general formula (G10), the triazole derivative represented by the general formula (G11) is preferable because the steric hindrance is reduced and thus synthesis is facilitated.

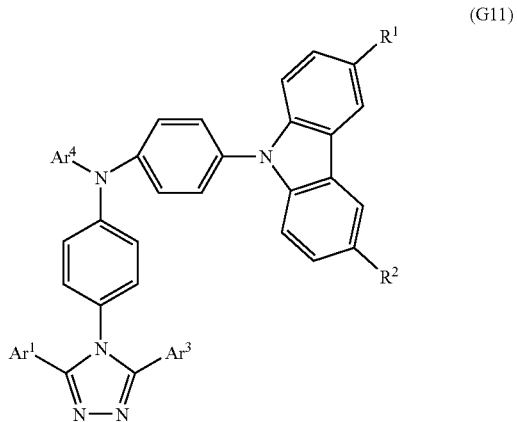

(G11)

In the general formula (G11), $Ar^1$ and $Ar^3$ individually represent an aryl group having 6 to 25 carbon atoms or a heteroaryl group having 3 to 9 carbon atoms, $Ar^4$ represents an aryl group having 6 to 25 carbon atoms, and $R^{11}$ and $R^{12}$ individually represent hydrogen, an aryl group having 6 to 25 carbon atoms, an alkyl group having 1 to 4 carbon atoms, or an alkoxy group having 1 to 4 carbon atoms.

As the triazole derivative represented by the general formula (G11), the triazole derivative represented by the general formula (G12) is preferable because the steric hindrance is reduced and thus synthesis is facilitated.

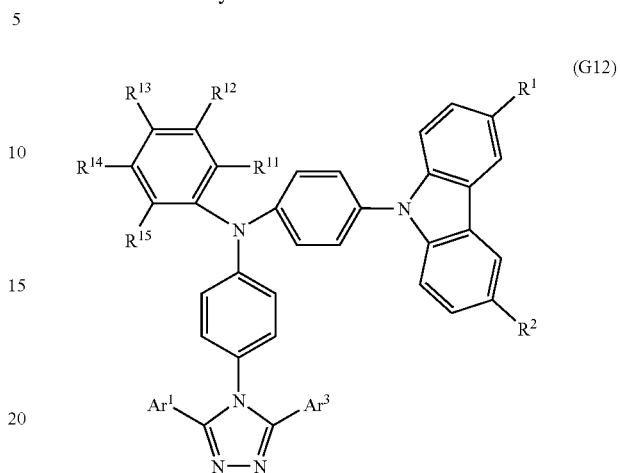

(G12)

In the above general formula (G12), $Ar^1$ and $Ar^3$ individually represent an aryl group having 6 to 25 carbon atoms or a heteroaryl group having 3 to 9 carbon atoms, and $R^{11}$ and $R^{12}$ individually represent hydrogen, an aryl group having 6 to 25 carbon atoms, an alkyl group having 1 to 4 carbon atoms, or an alkoxy group having 1 to 4 carbon atoms.

In the general formulae (G1″) and (G8) to (G12), for ease of synthesis, it is preferable that $Ar^1$ and $Ar^3$ be individually a phenyl group or a pyridyl group. Because of the high triplet excitation energy, it is preferable that $Ar^1$ and $Ar^3$ be individually a phenyl group or a pyridyl group. In particular, a pyridyl group is preferable. By adopting a pyridyl group, the electron-transporting property of the triazole derivative increases to improve carrier balance. Accordingly, the triazole derivative of the present invention can be preferably used for a light-emitting element. Since the balance between injected electrons and holes is important particularly for a light-emitting layer of a light-emitting element, the triazole derivative of the present invention is more preferably used for a light-emitting layer.

As the triazole derivatives represented by the general formulae (G1′) and (G1″), specifically, triazole derivatives represented by structural formulae (1) to (119) and (120) to (199) can be given. However, the present invention is not limited these.

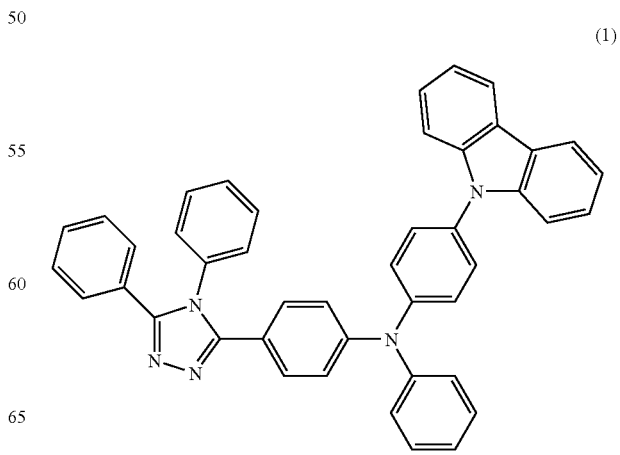

(1)

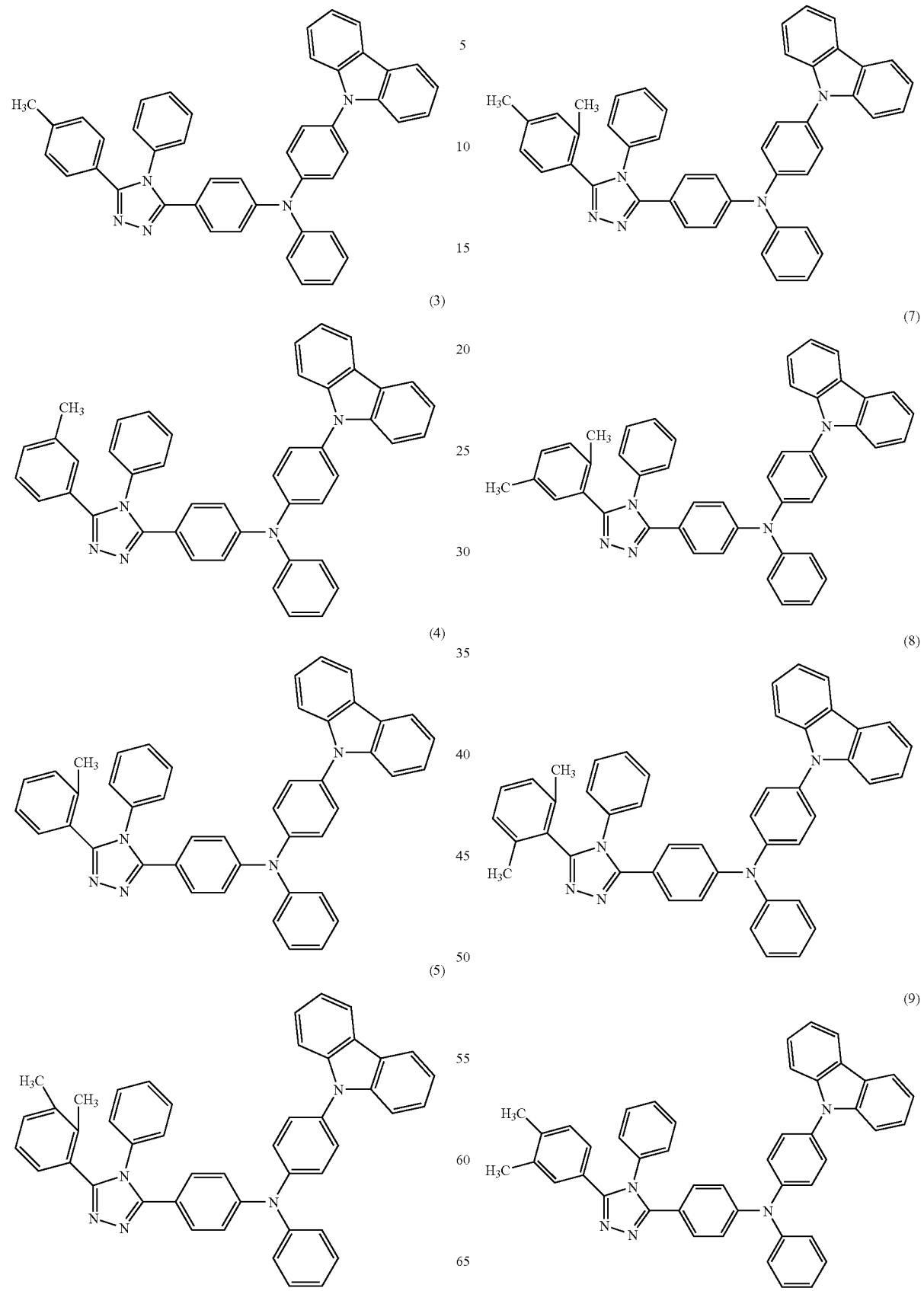

(10)
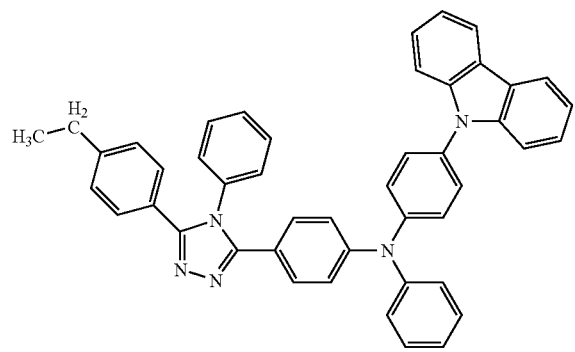
(11)
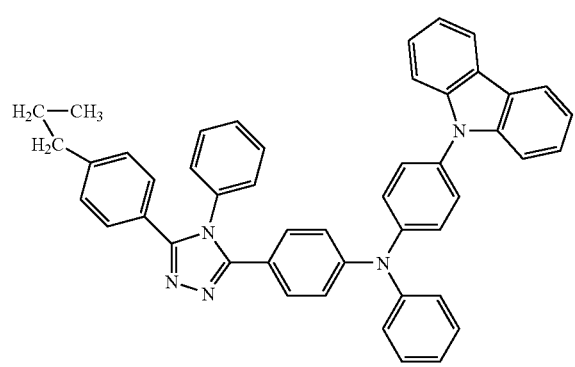
(12)
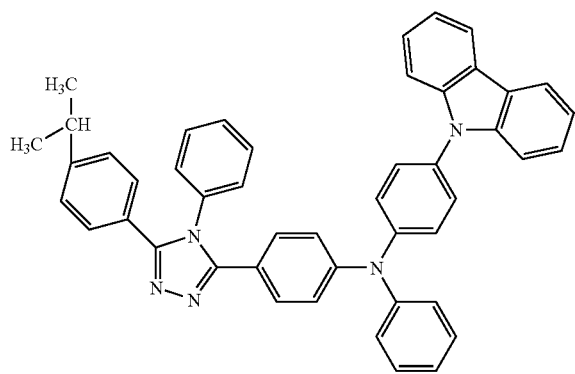
(13)
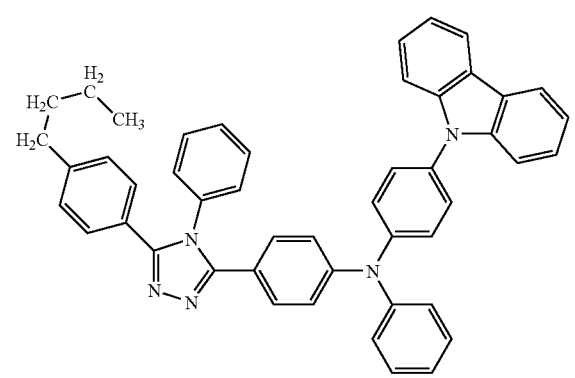
(14)
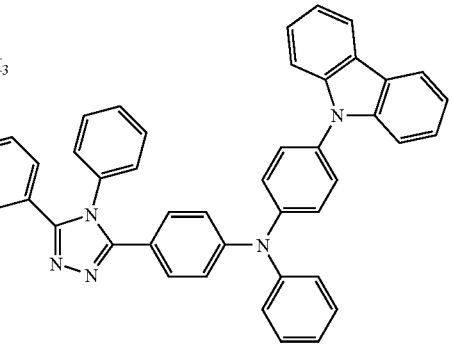
(15)
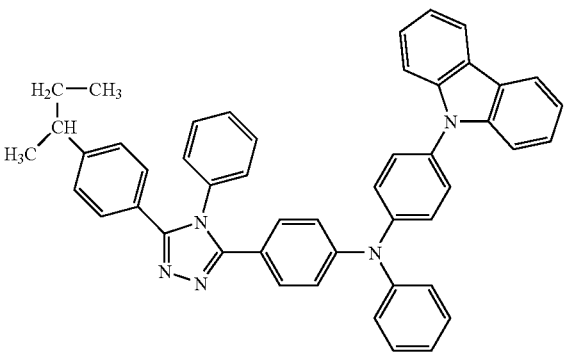
(16)
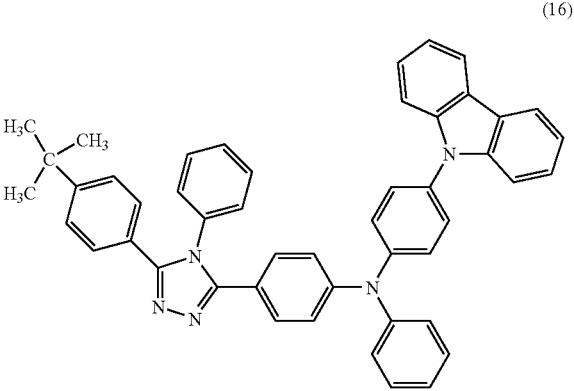
(17)
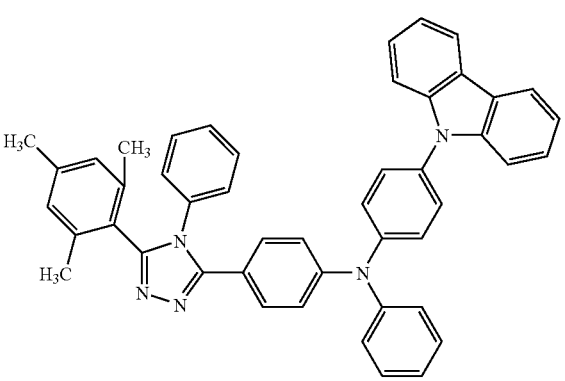

(18)
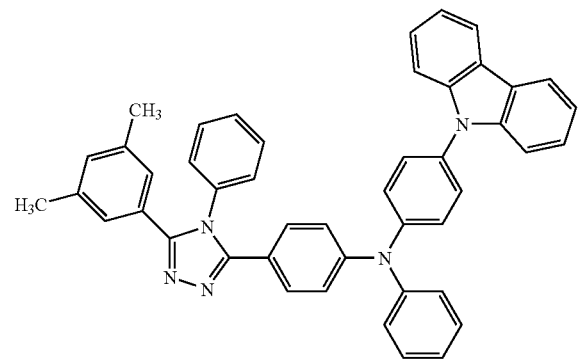
(22)
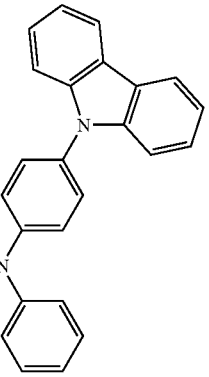
(19)
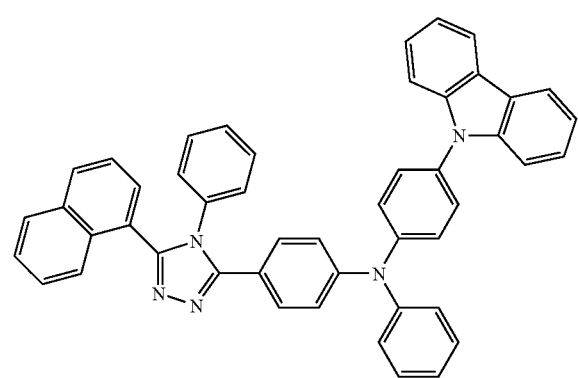
(23)
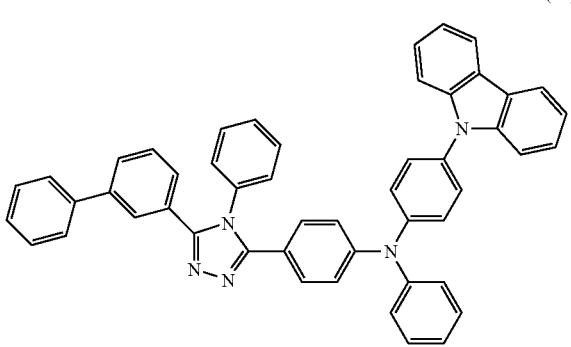
(20)
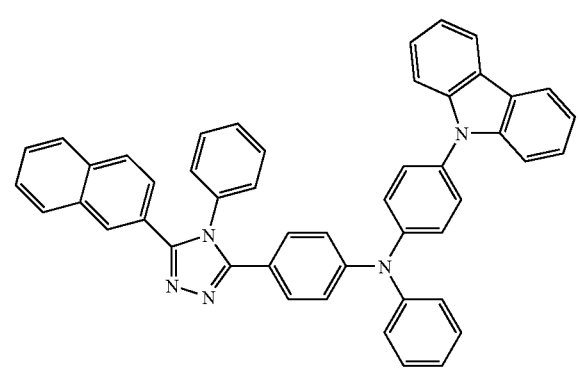
(24)
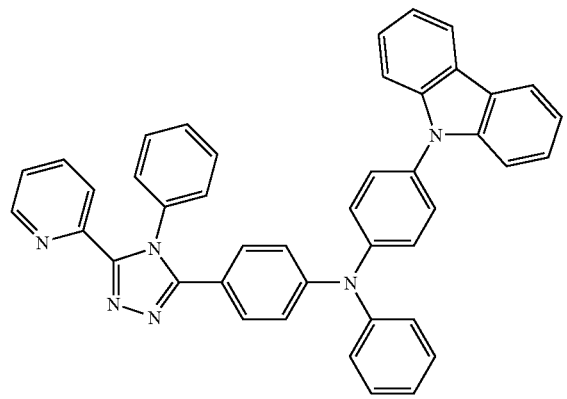
(21)
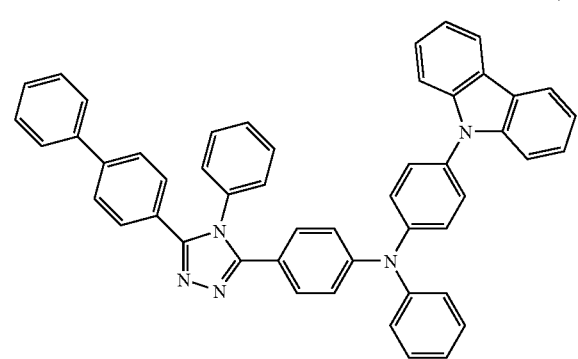
(25)
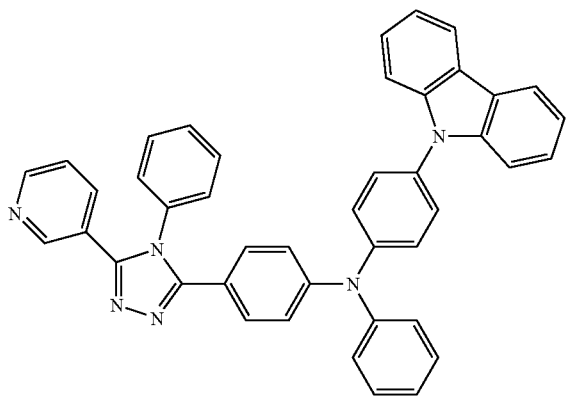

(26)
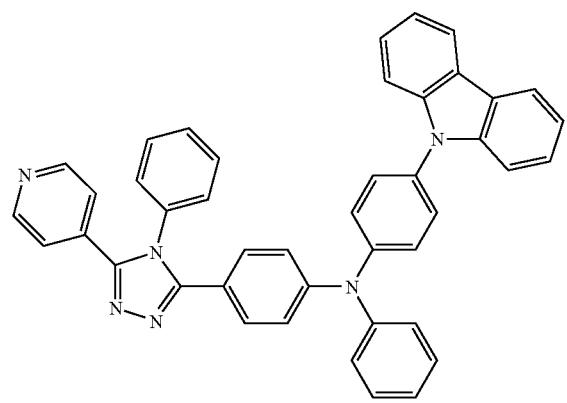
(27)
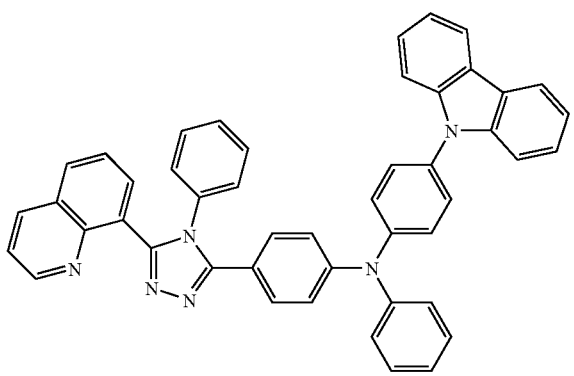
(28)
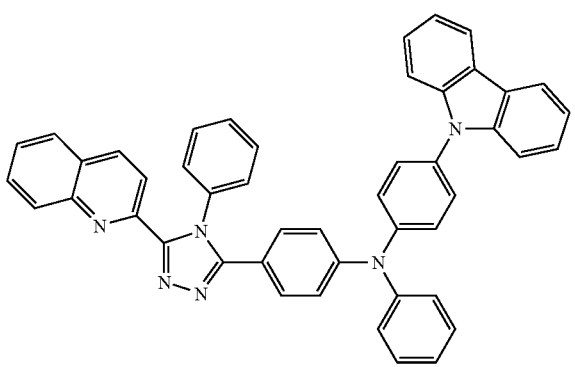
(29)
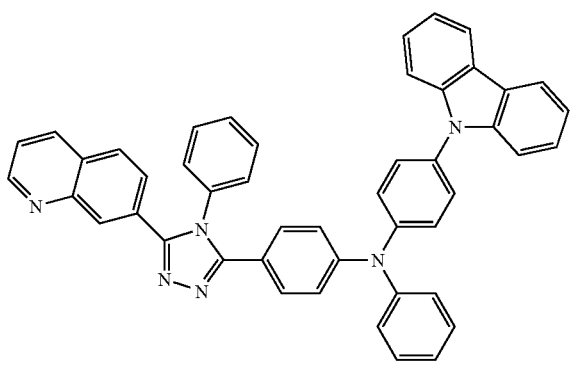
(30)
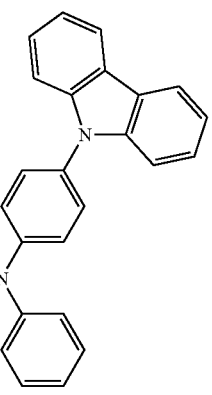
(31)
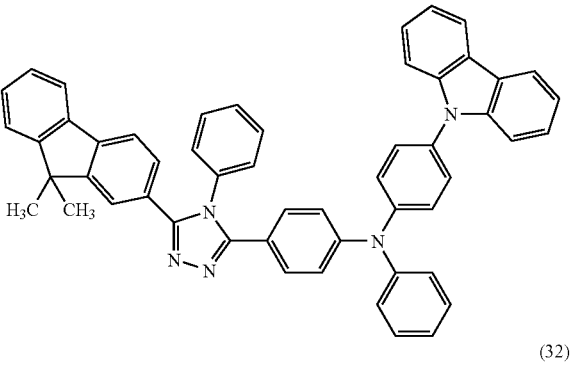
(32)
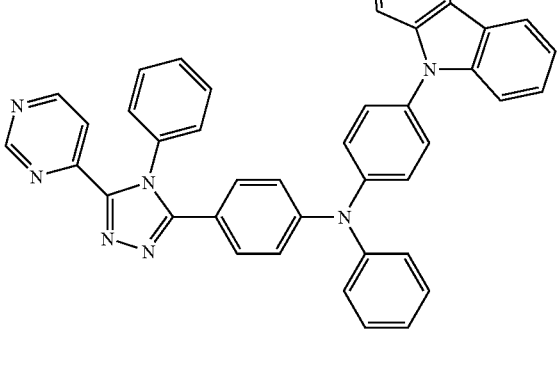
(33)
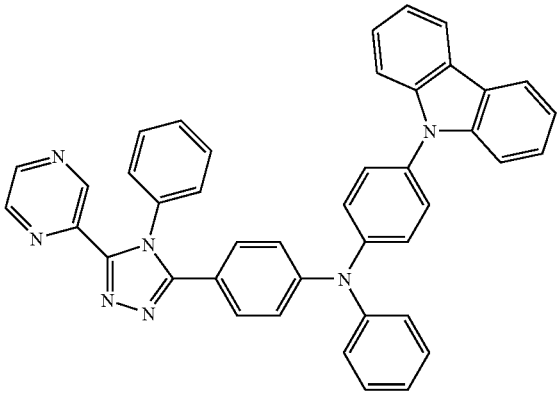

(34)
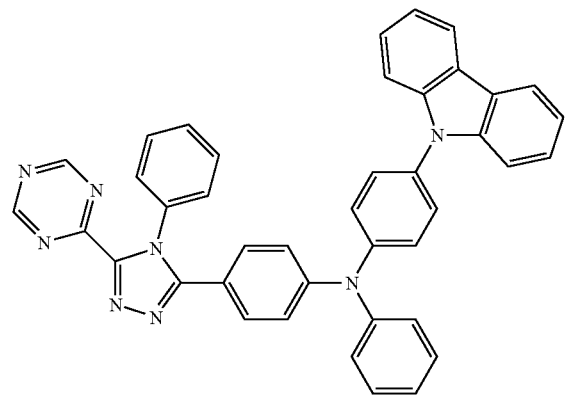
(35)
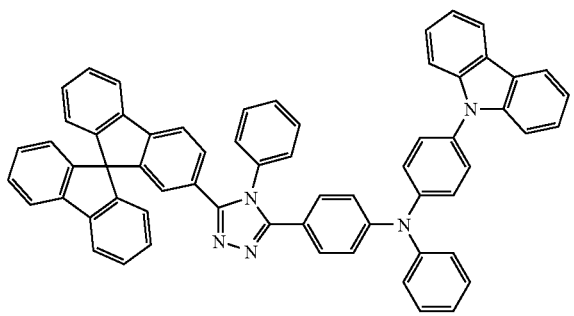
(36)
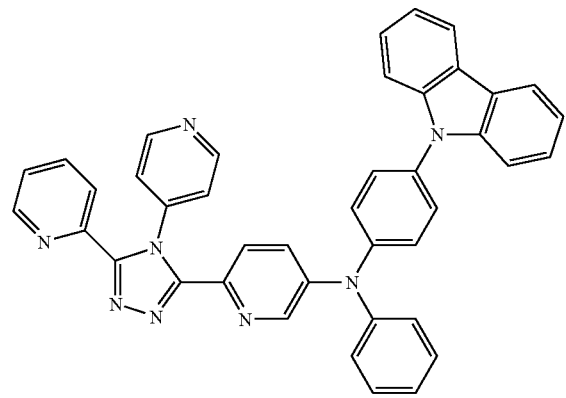
(37)
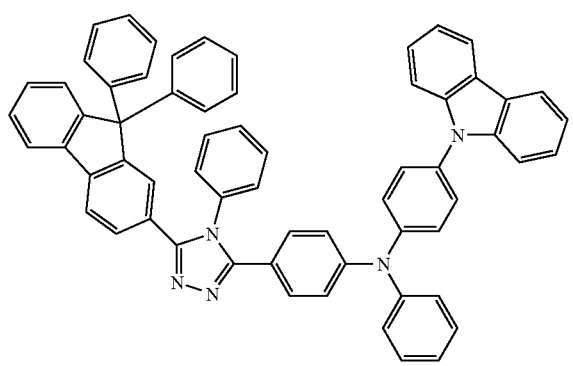
(38)
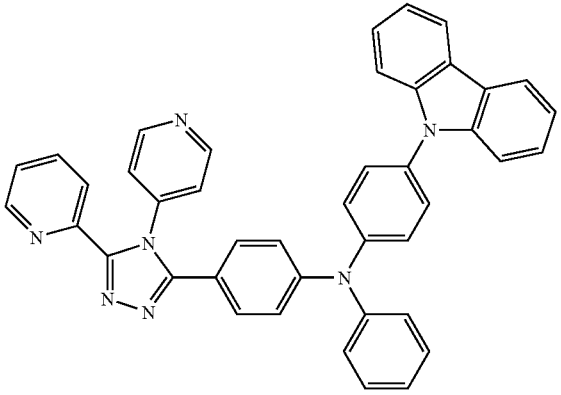
(39)
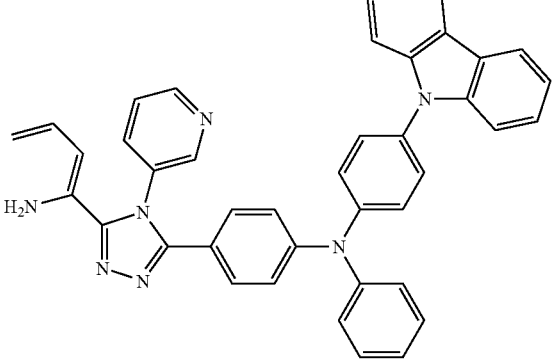
(40)
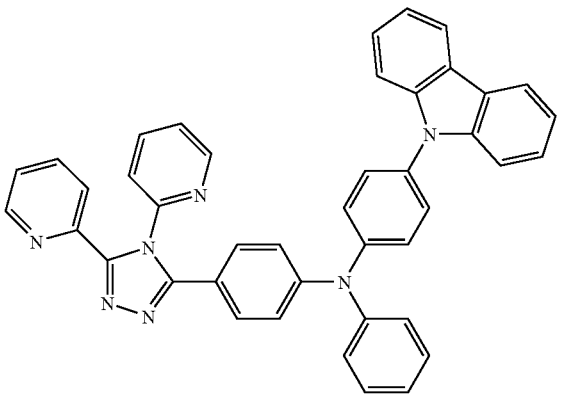
(41)
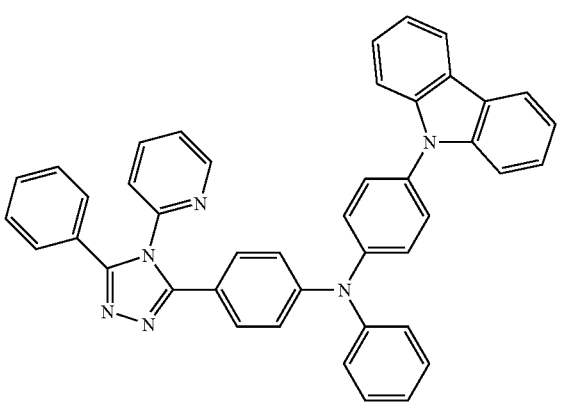

(42) 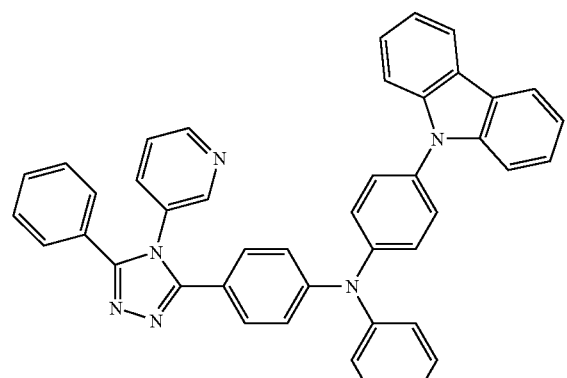
(43) 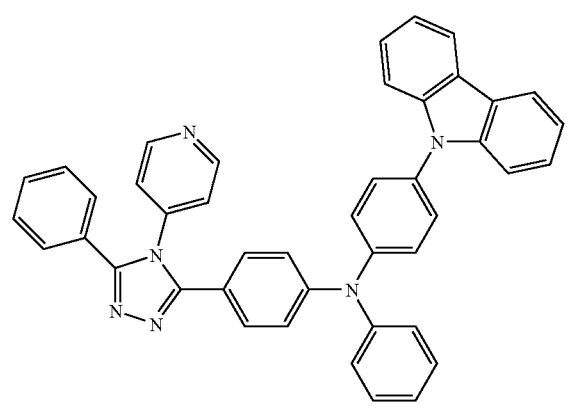
(44) 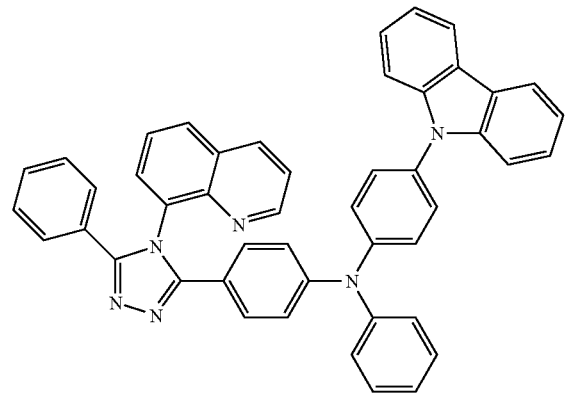
(45) 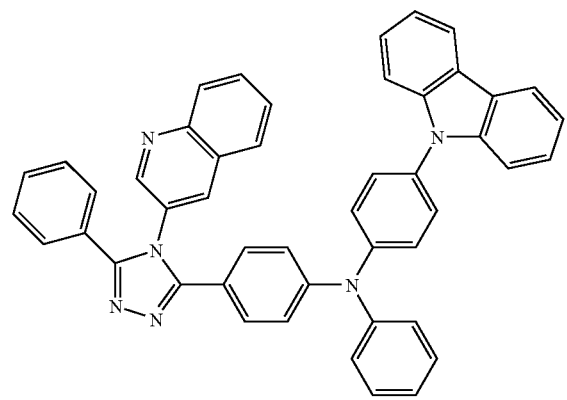
(46) 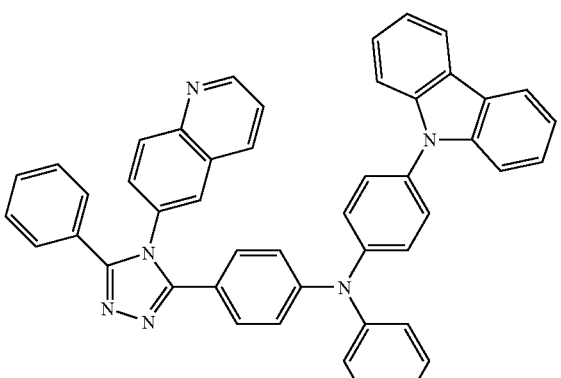
(47) 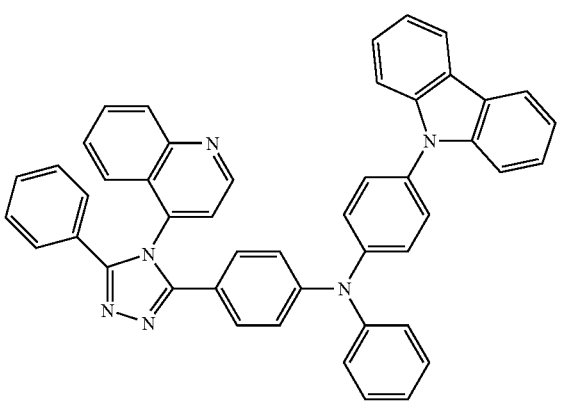
(48) 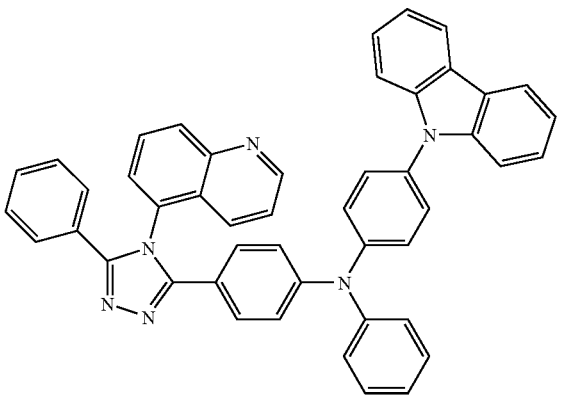
(49) 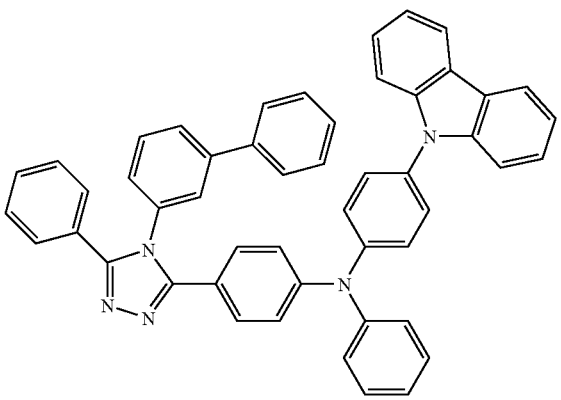

(50)
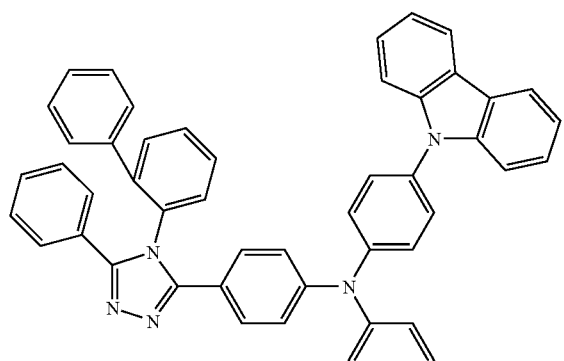
(51)
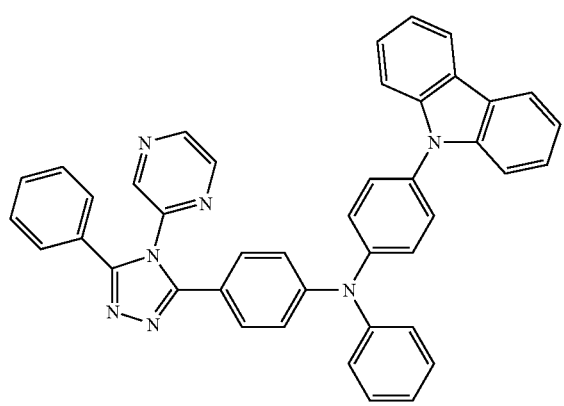
(52)
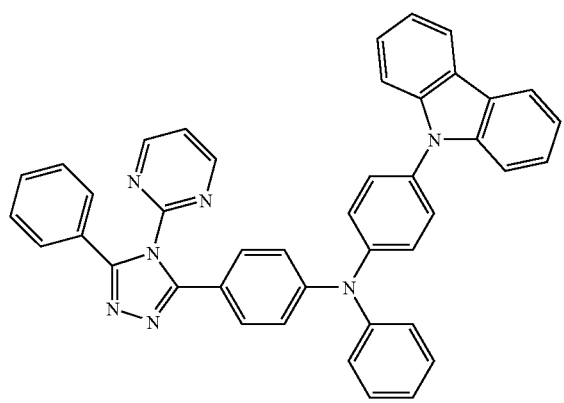
(53)
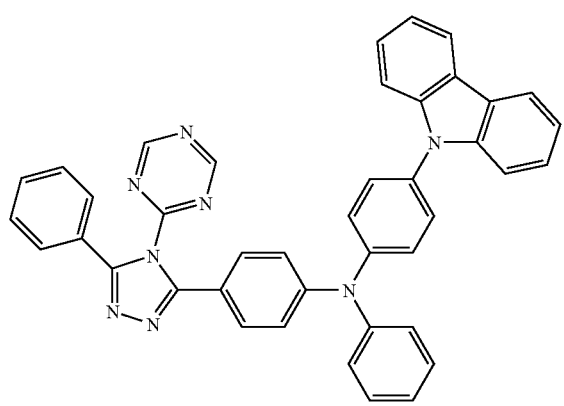
(54)
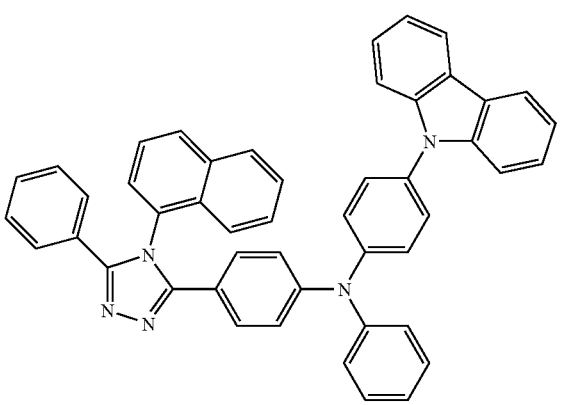
(55)
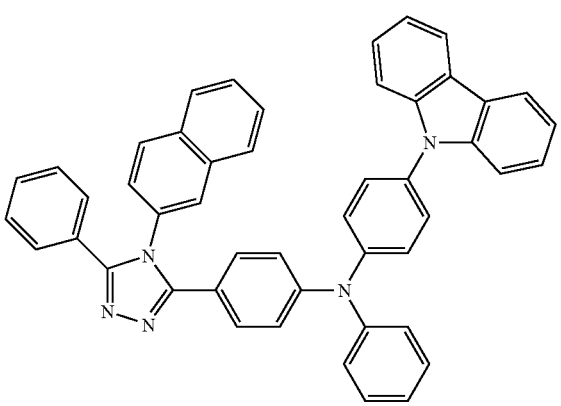
(56)
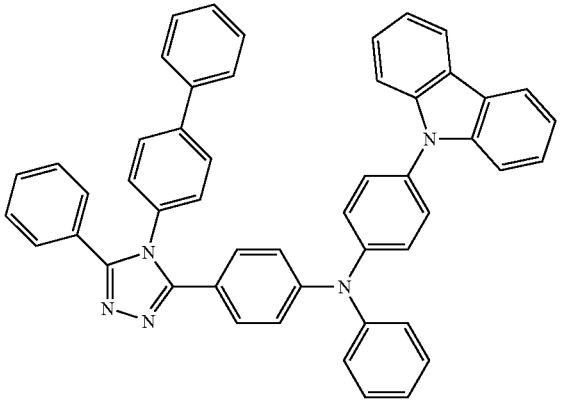

(57)
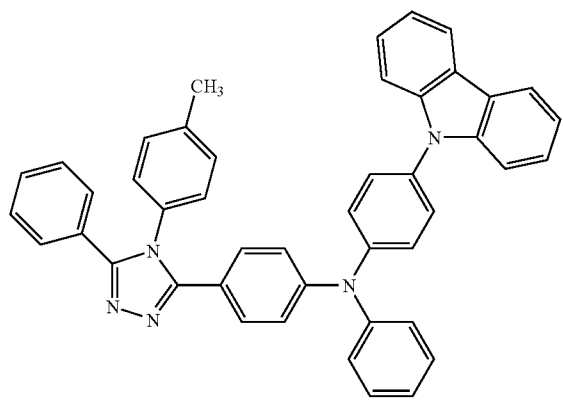
(58)
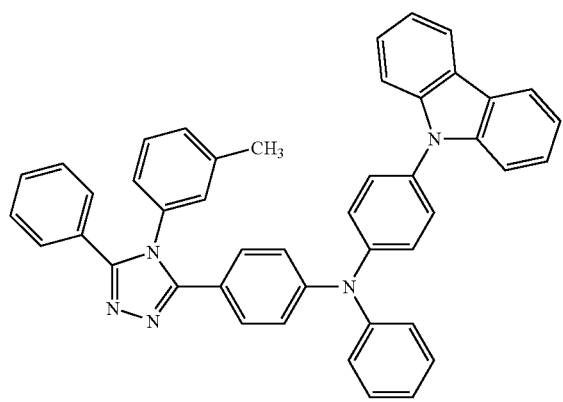
(59)
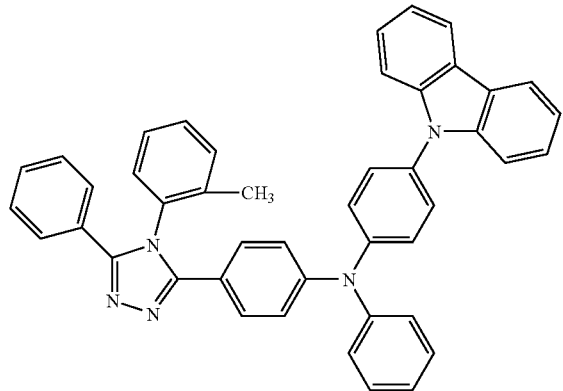
(60)
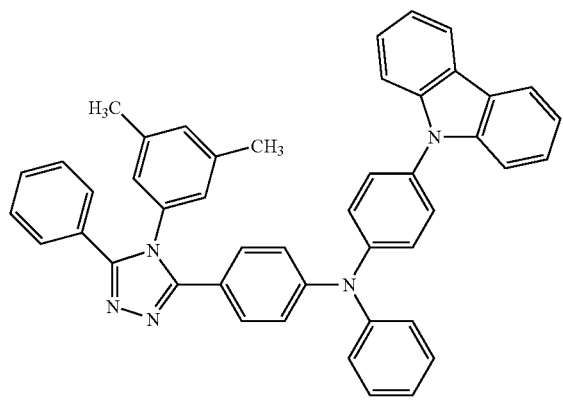
(61)
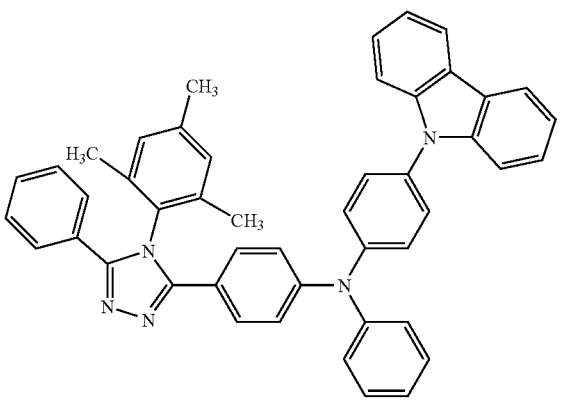
(62)
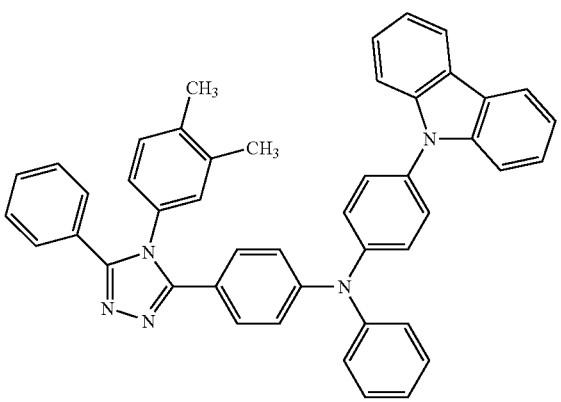
(63)
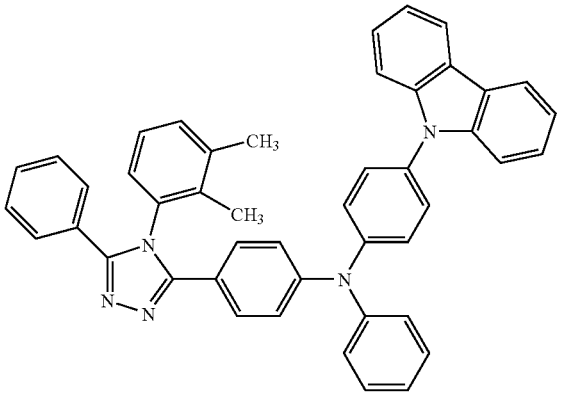
(64)
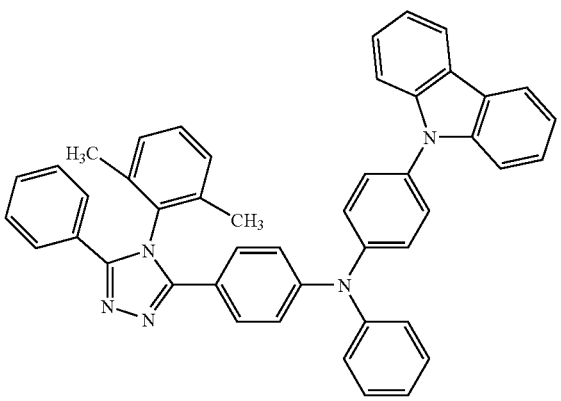

(65)
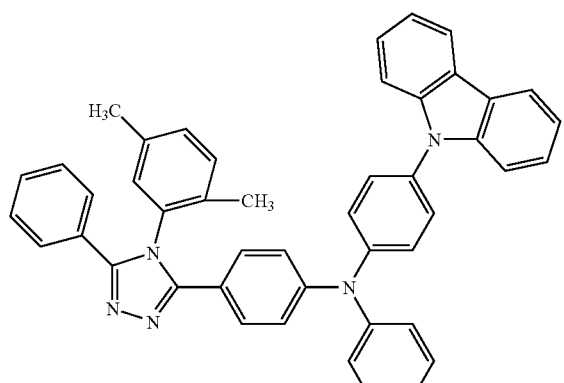
(66)
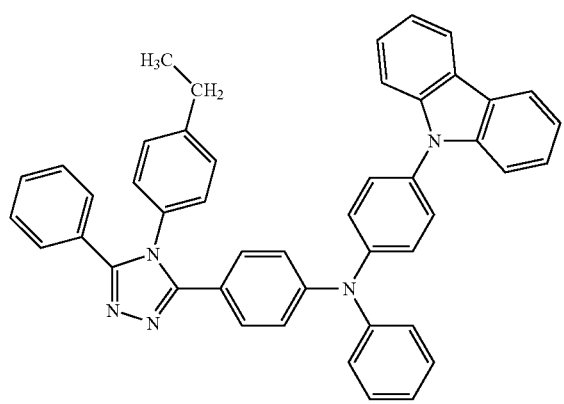
(67)
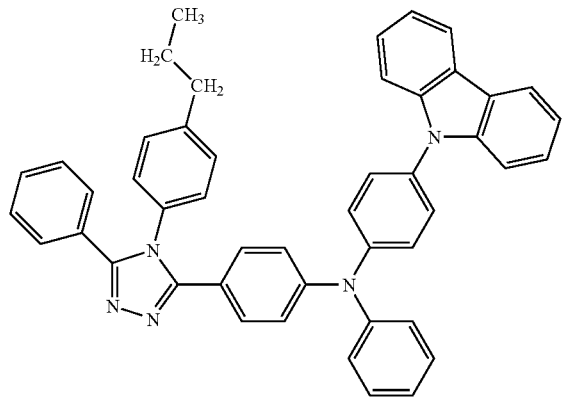
(68)
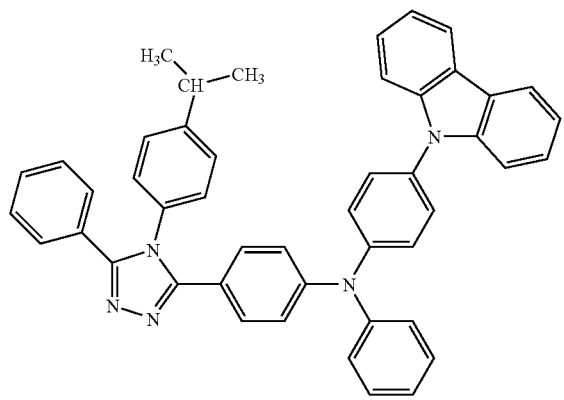
(69)
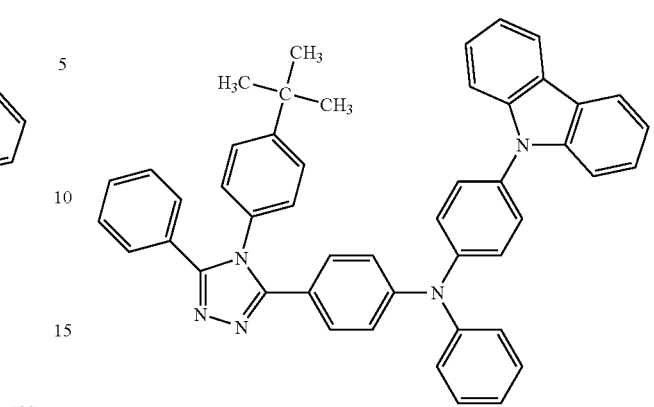
(70)
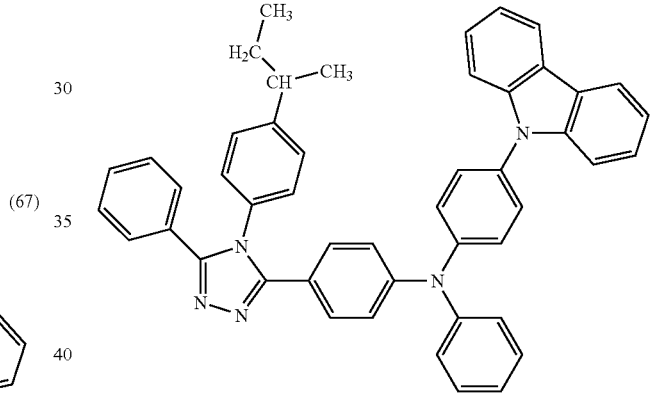
(71)
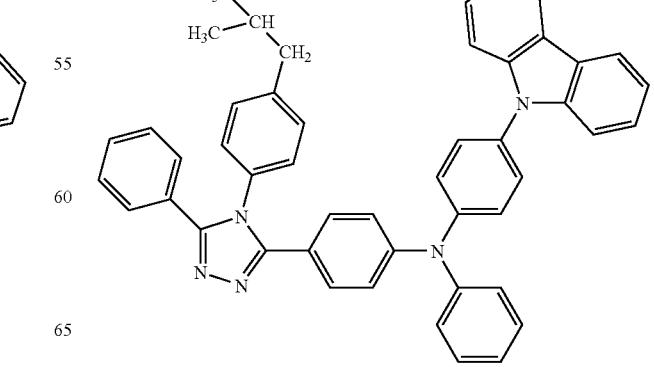

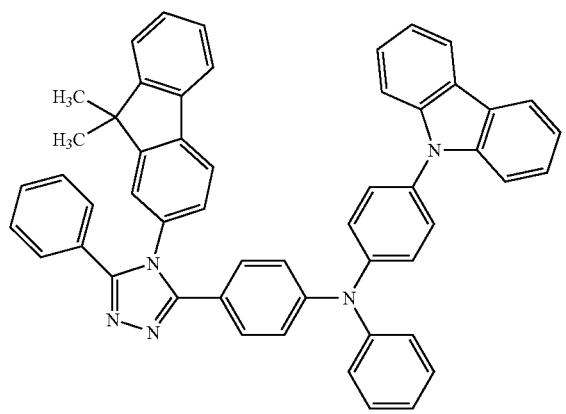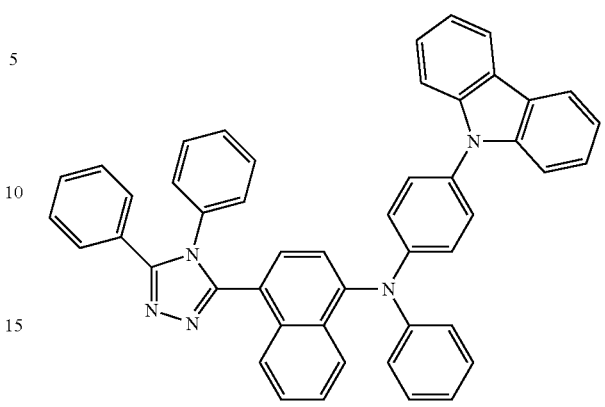

(79)
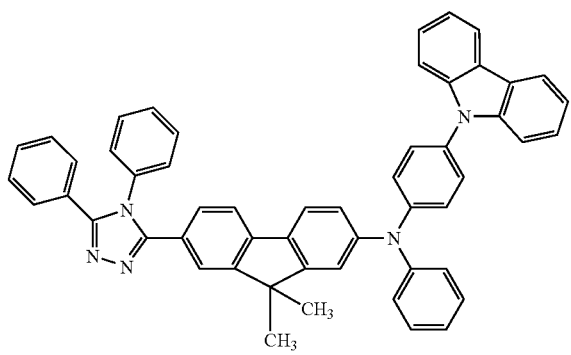
(80)
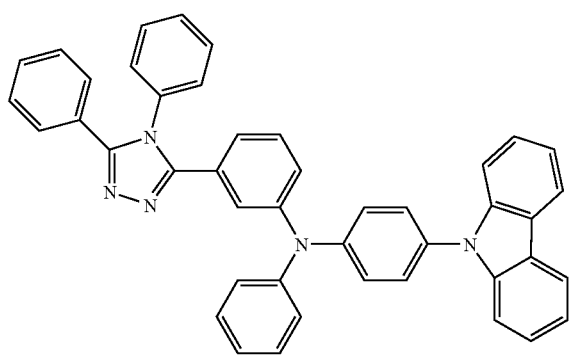
(81)
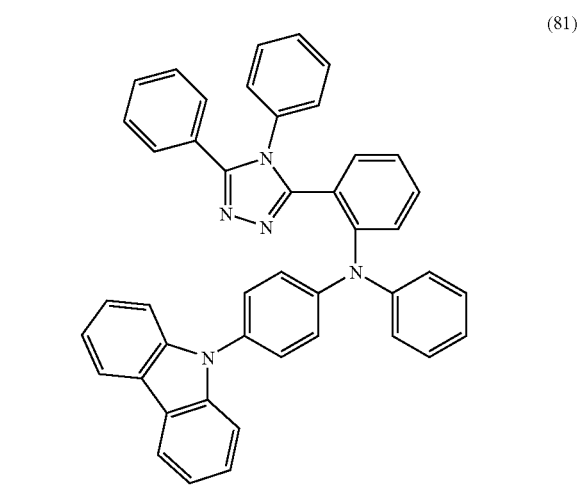
(82)
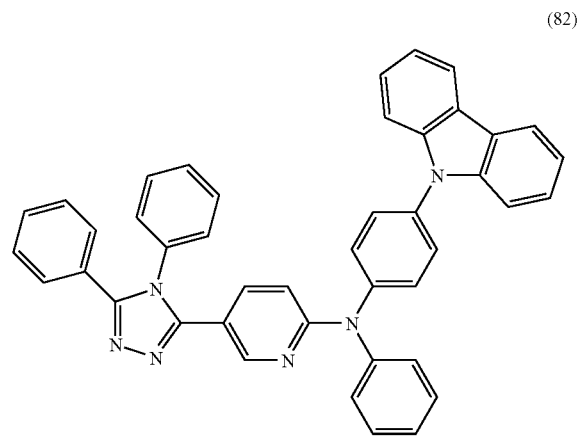
(83)
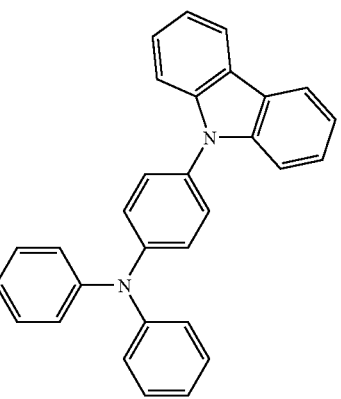
(84)
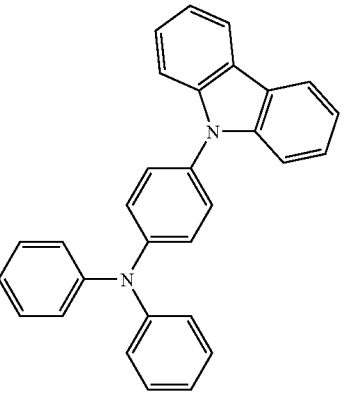
(85)
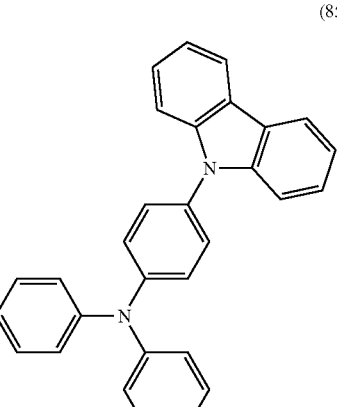
(86)
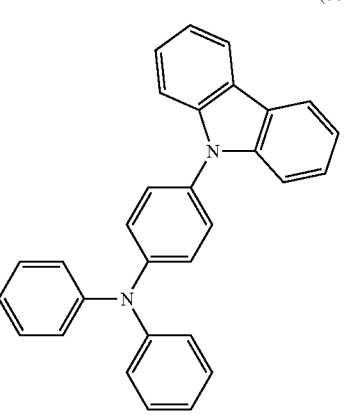

(87) 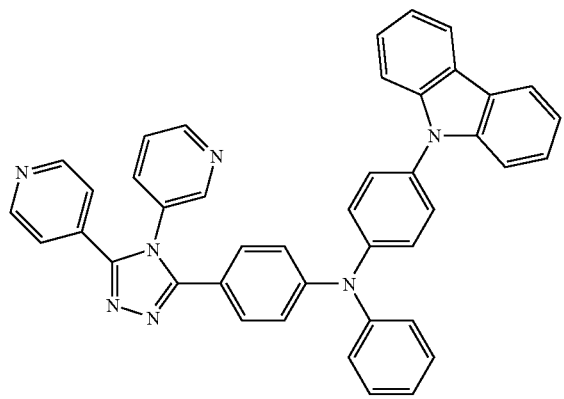
(88) 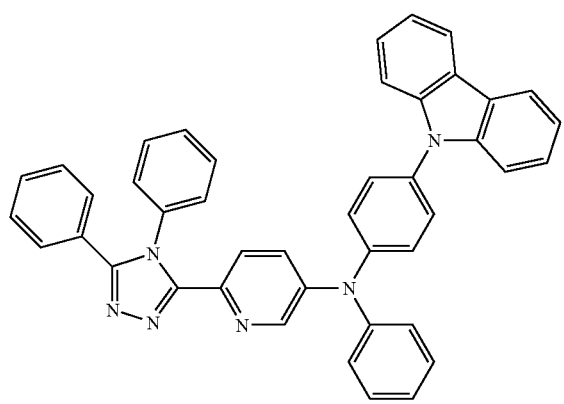
(89) 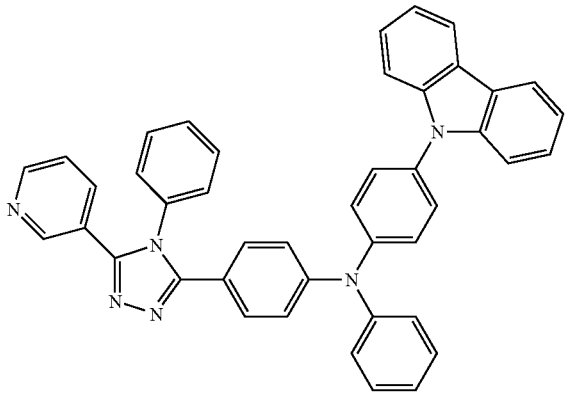
(90) 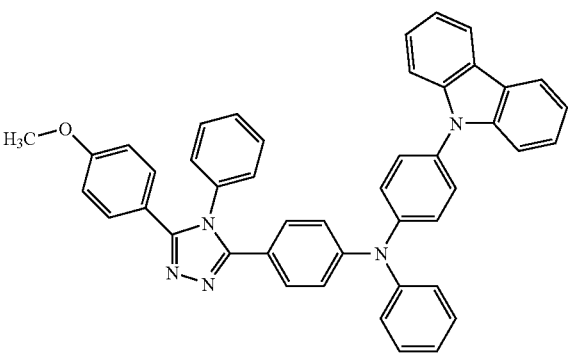
(91) 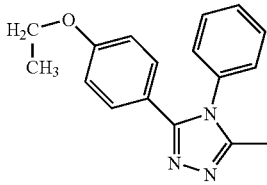 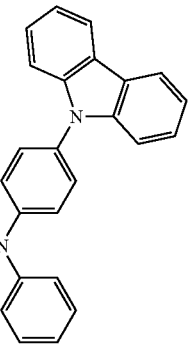
(92) 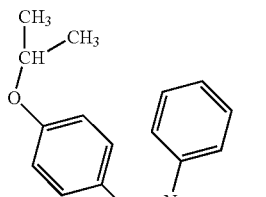 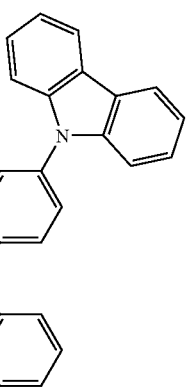
(93) 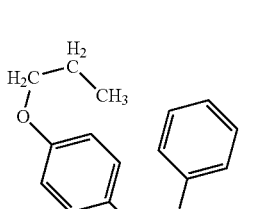 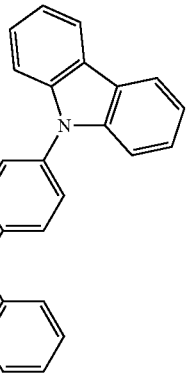
(94)

(95)
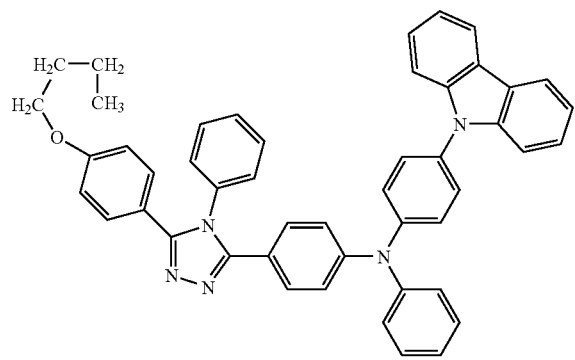
(96)
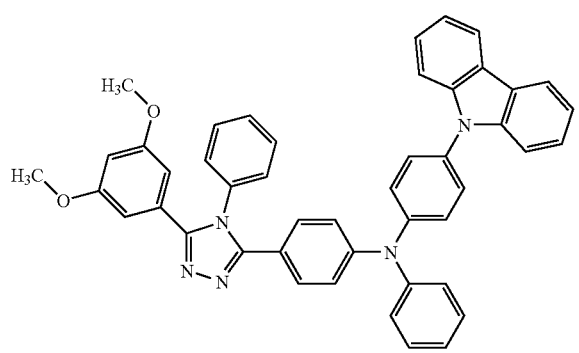
(99)
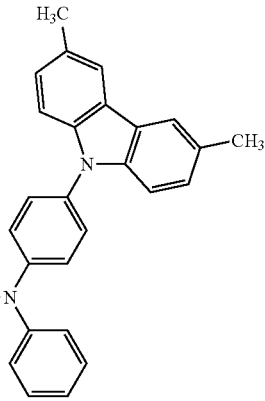
(97)
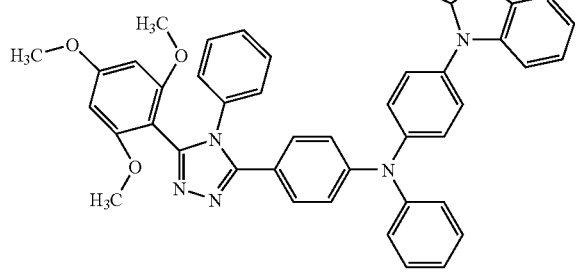
(98)
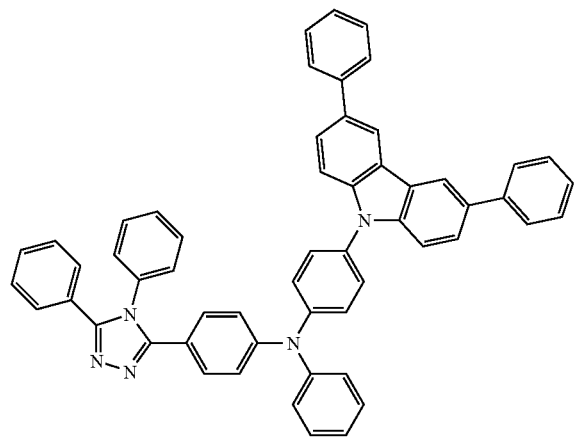
(100)
(101)
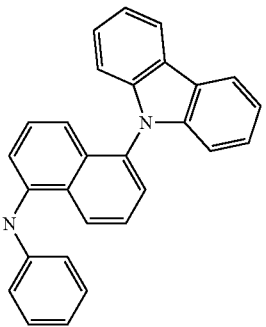

(102)
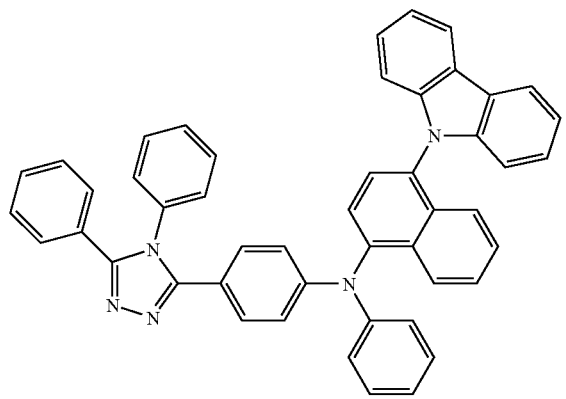
(103)
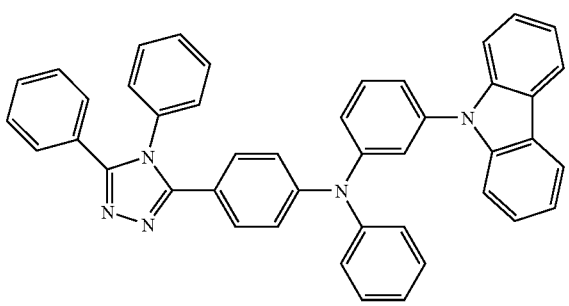
(104)
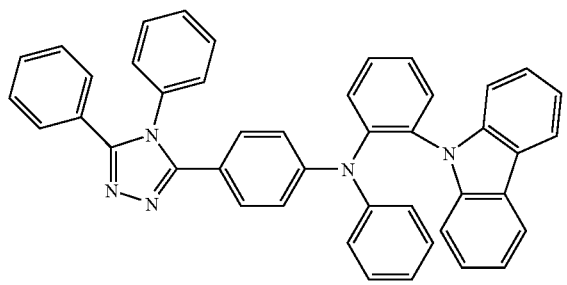
(105)
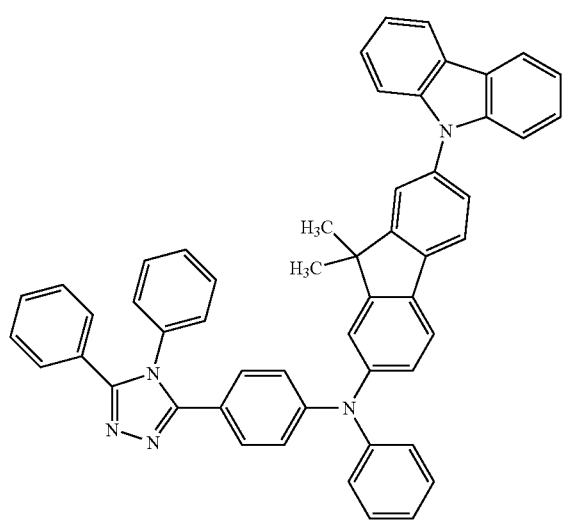
(106)
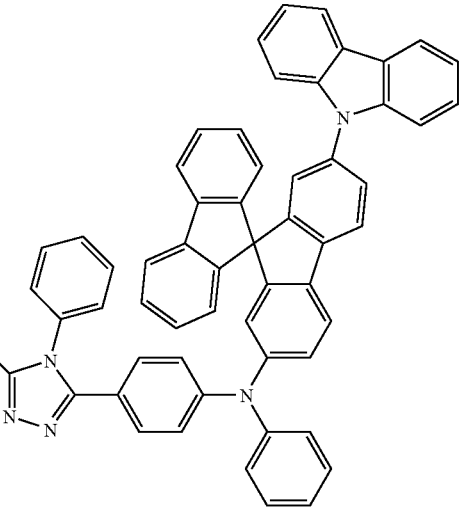
(107)
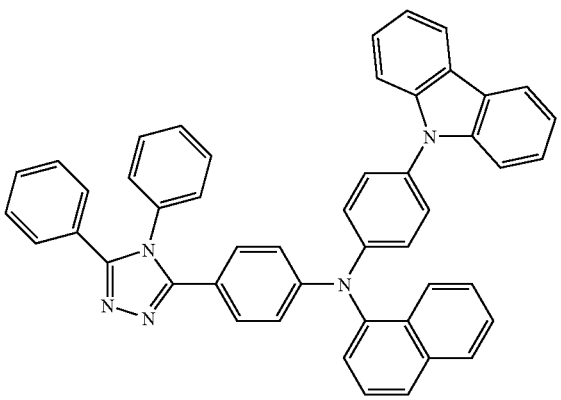
(108)
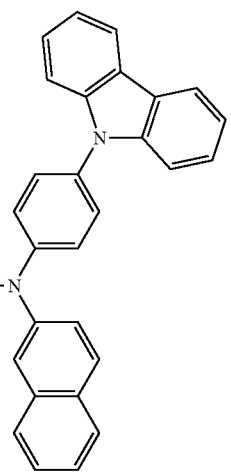

(109)
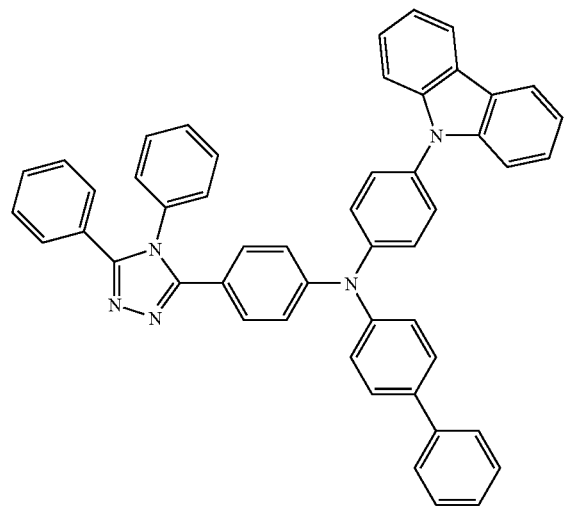
(110)
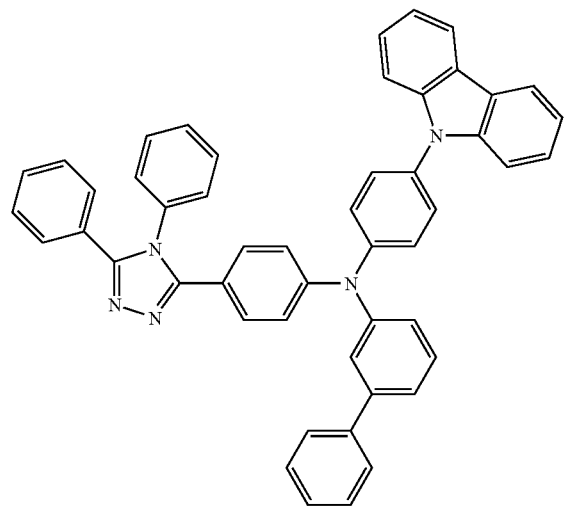
(111)
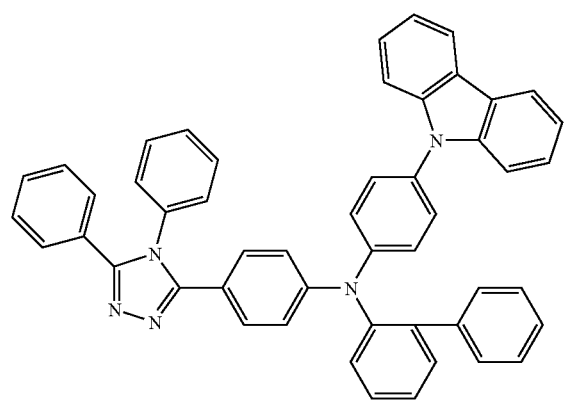
(112)
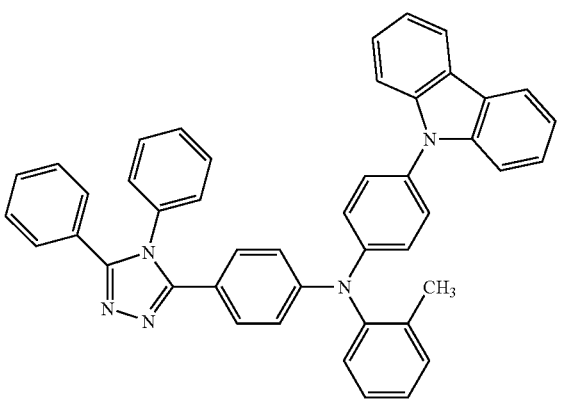
(113)
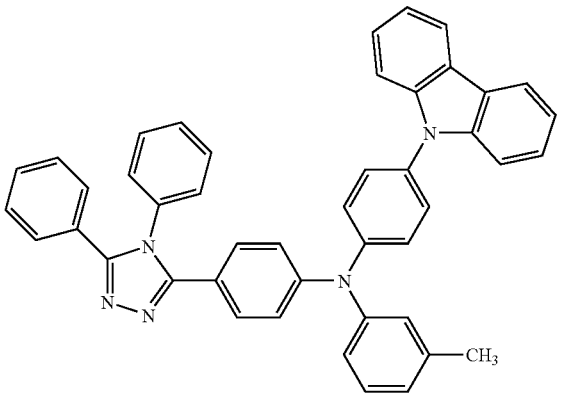
(114)
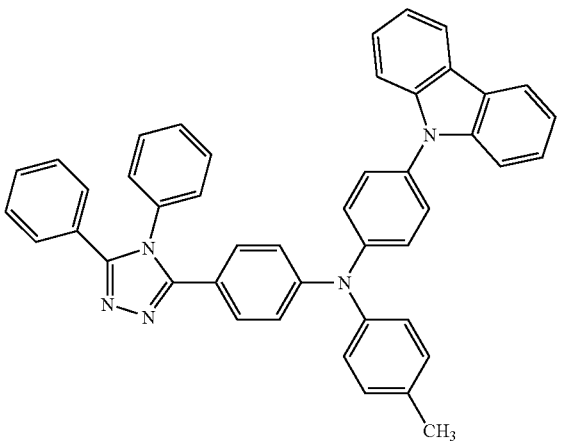

-continued
(115)
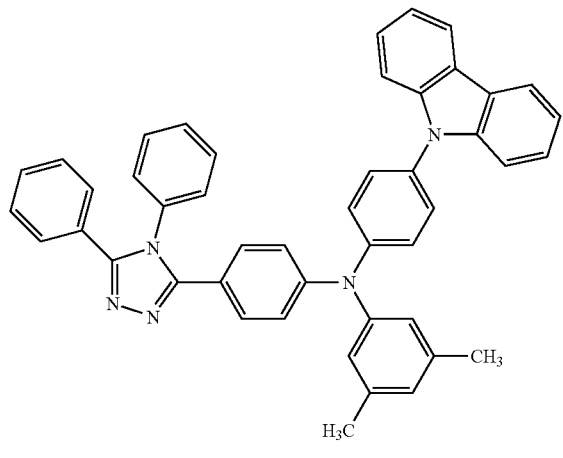
(116)
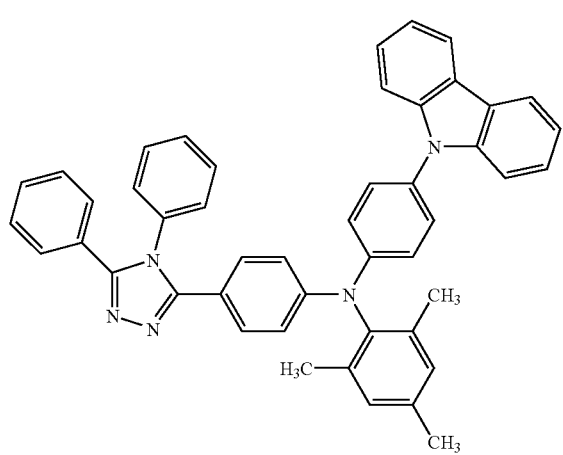
(117)
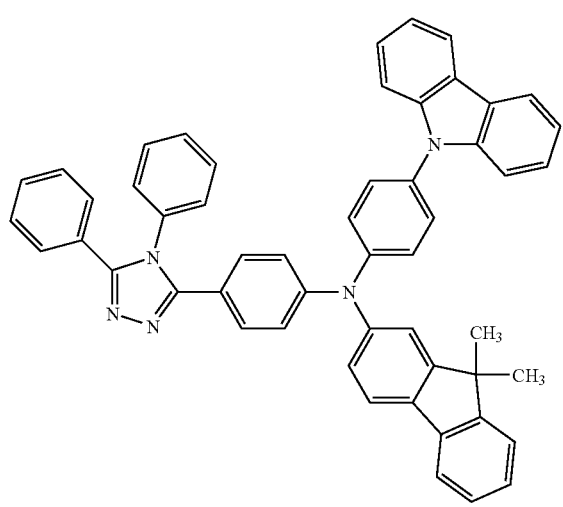
-continued
(118)
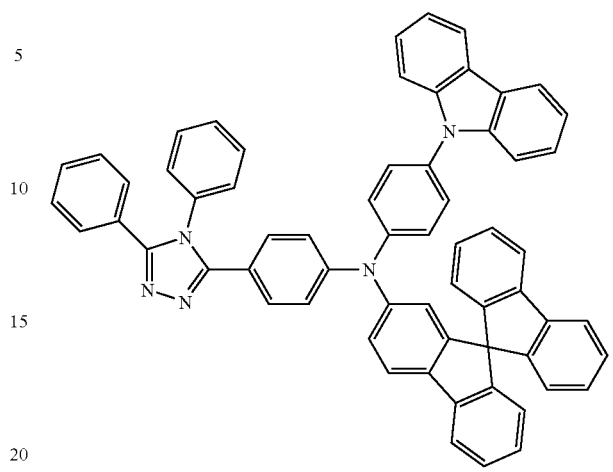
(119)
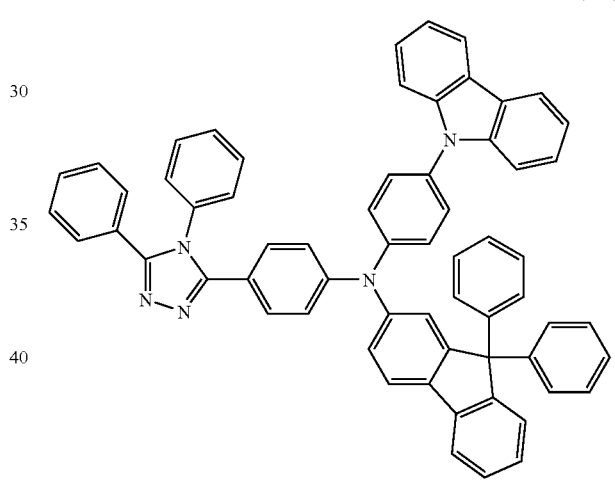
(120)
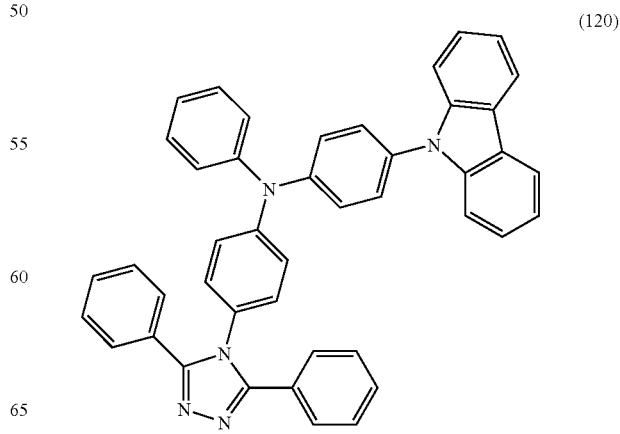

(121)
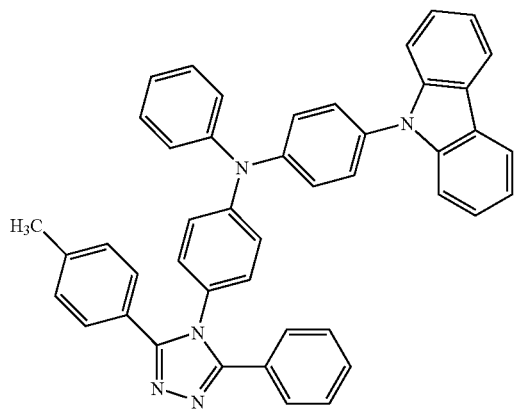
(124)
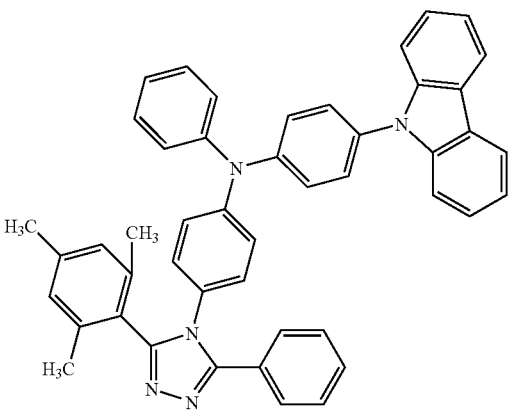
(122)
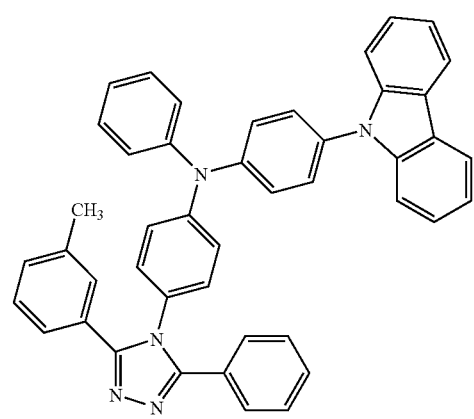
(125)
(123)
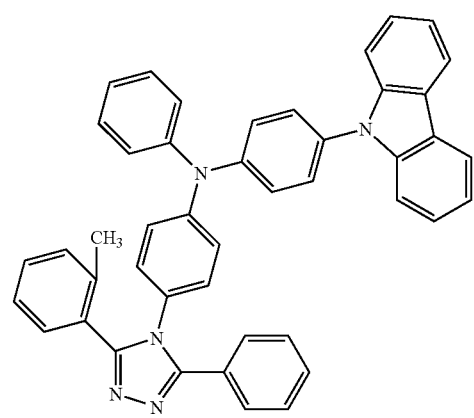
(126)
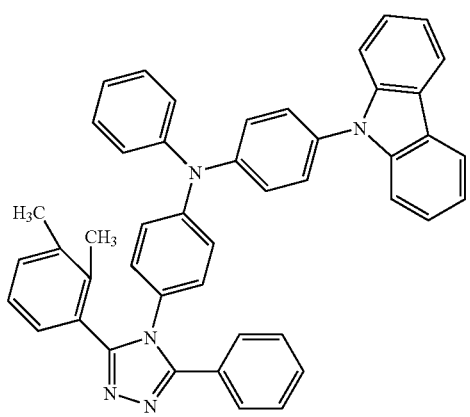

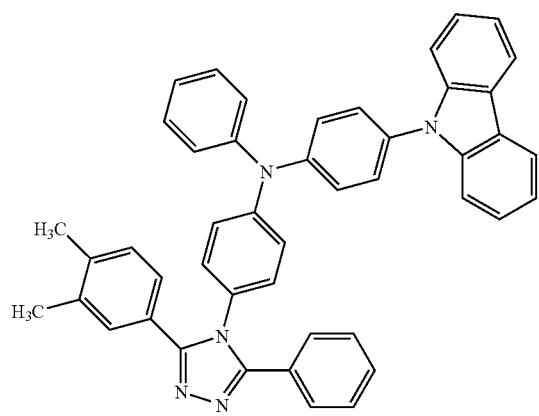
(127)
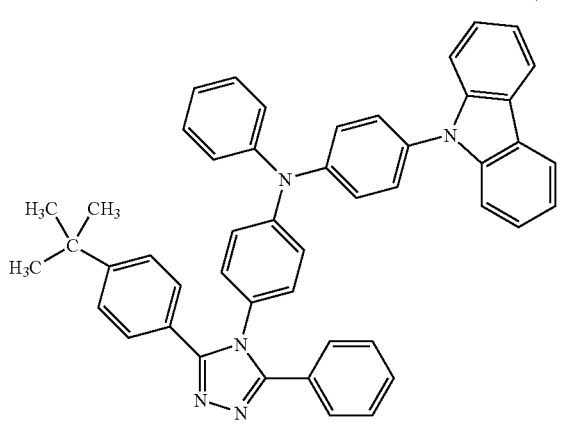
(130)
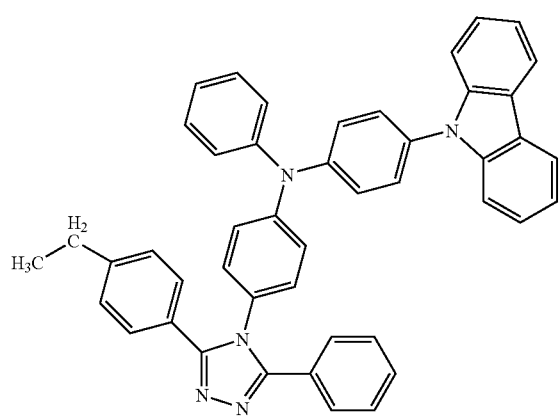
(128)
(131)
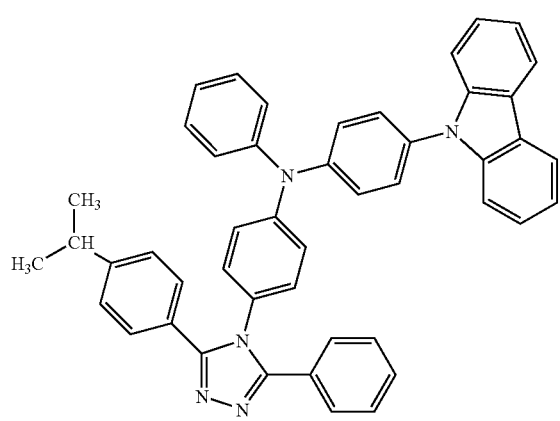
(129)
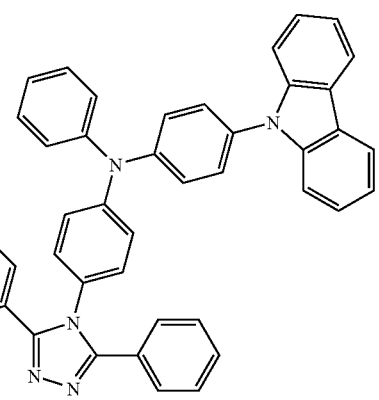
(132)

(133)
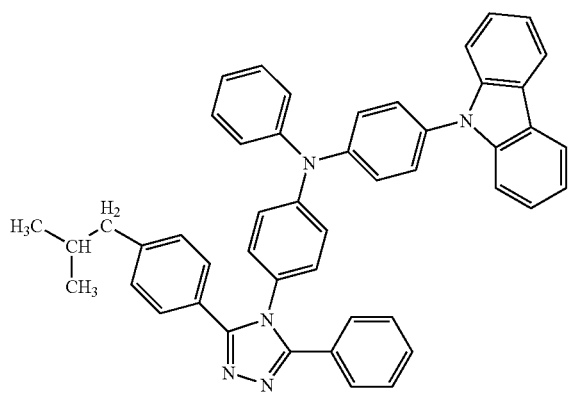
(134)
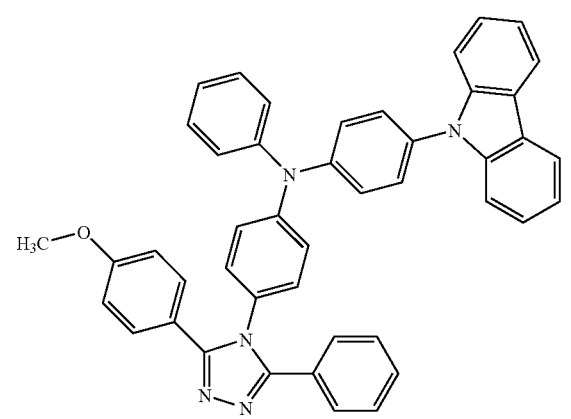
(135)
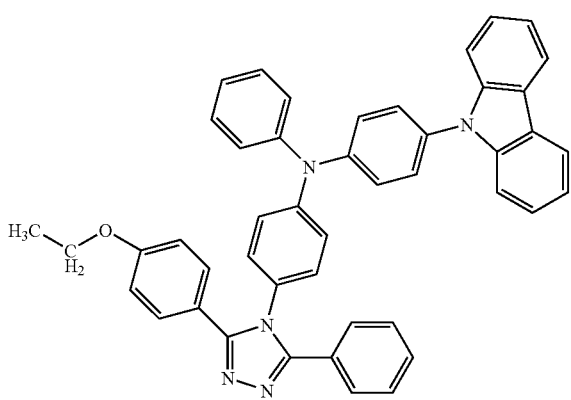
(136)
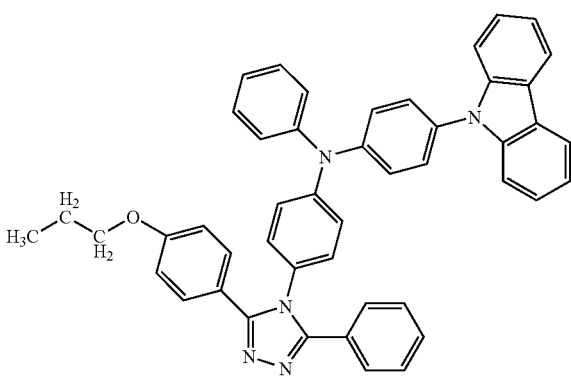
(137)
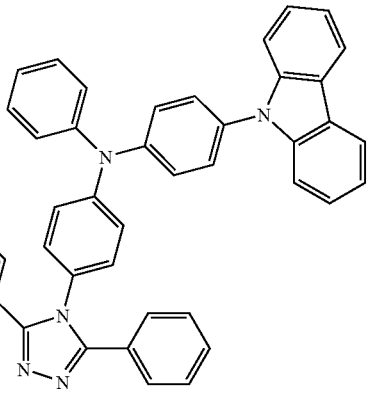
(138)
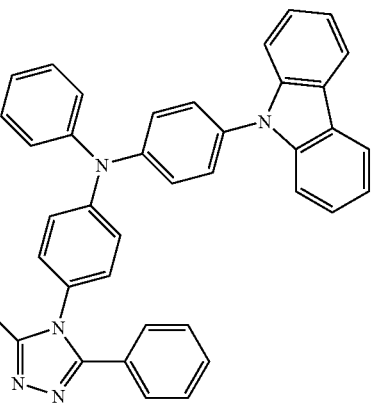
(139)
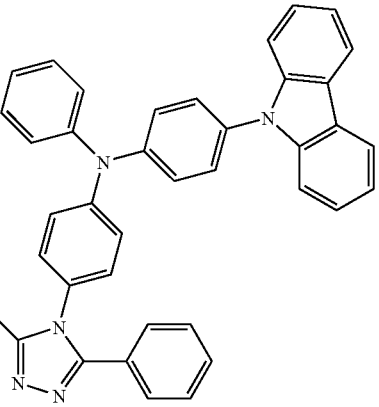
(140)
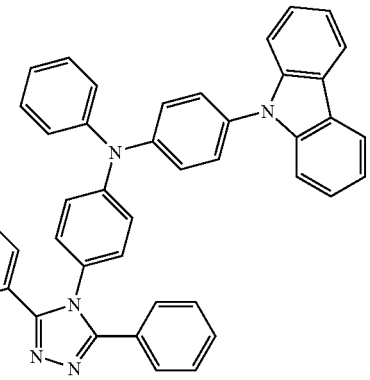

(141)
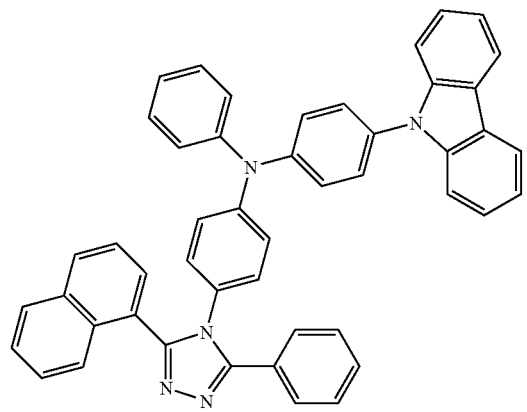
(142)
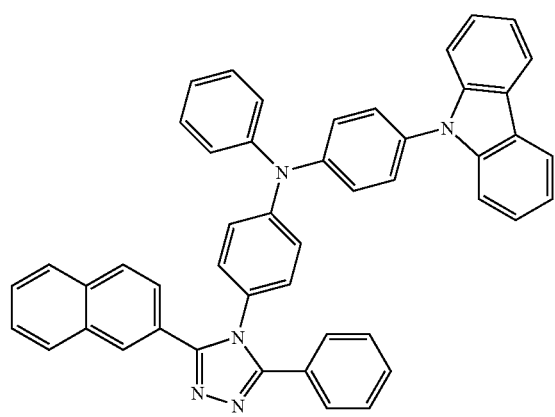
(143)
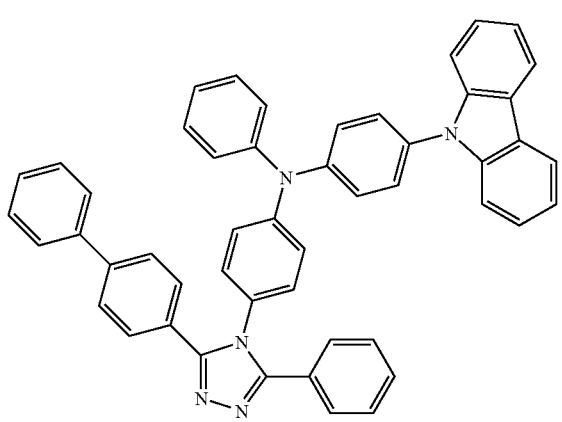
(144)
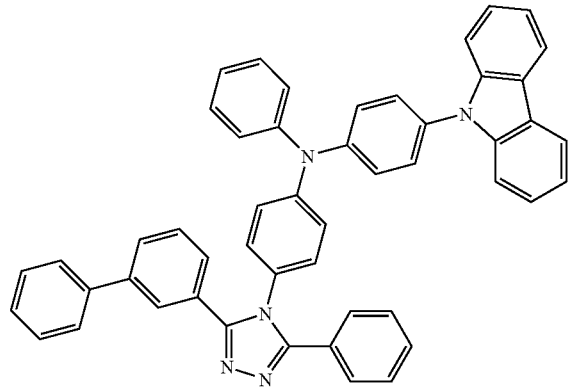
(145)
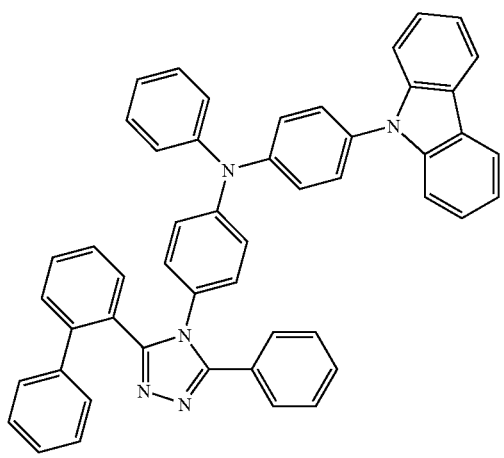
(146)
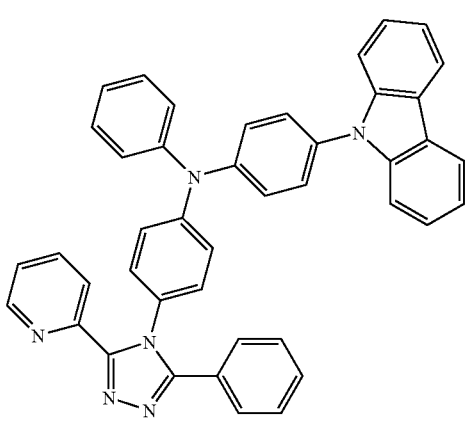

(147) 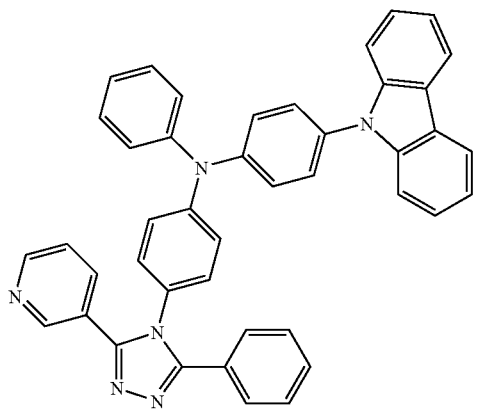
(148) 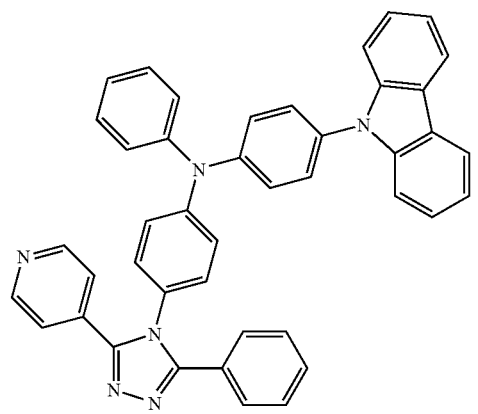
(149) 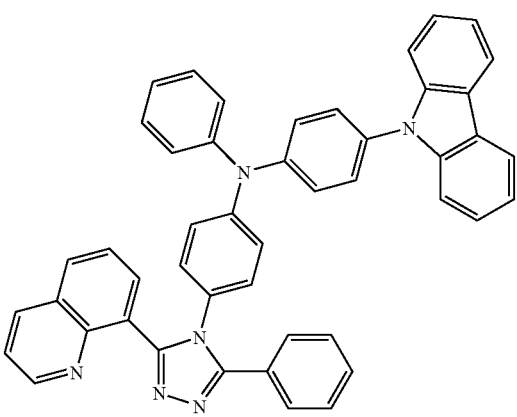
(150) 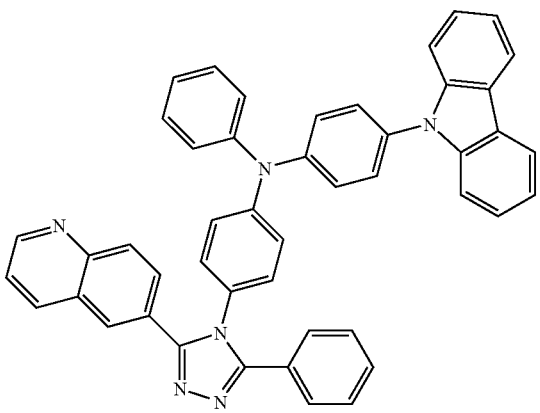
(151) 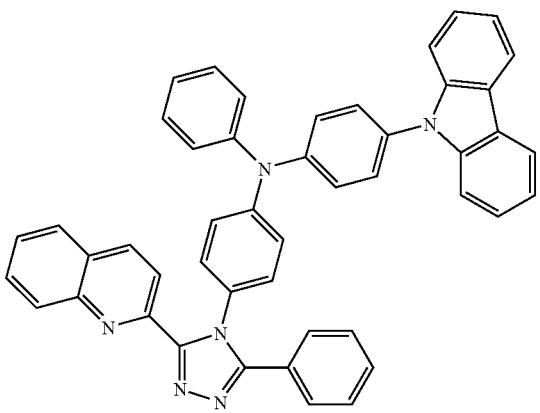
(152) 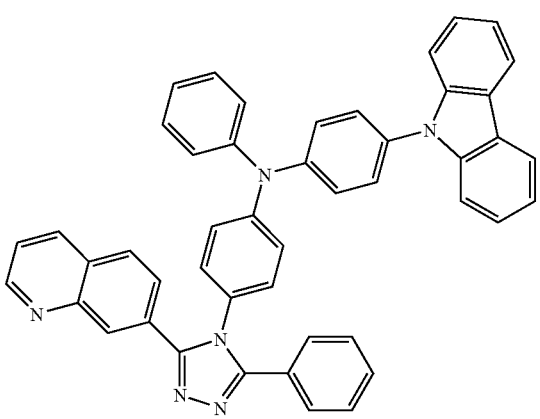

(153)
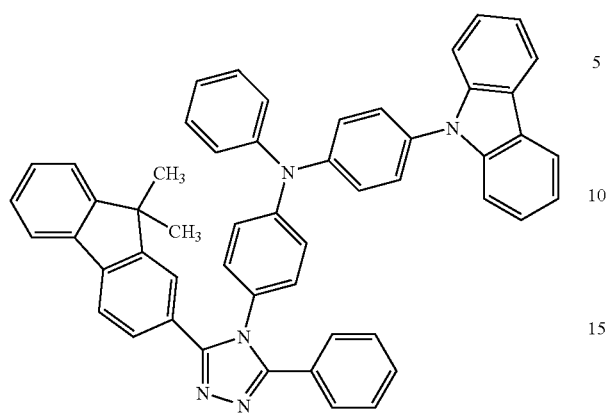
(154)
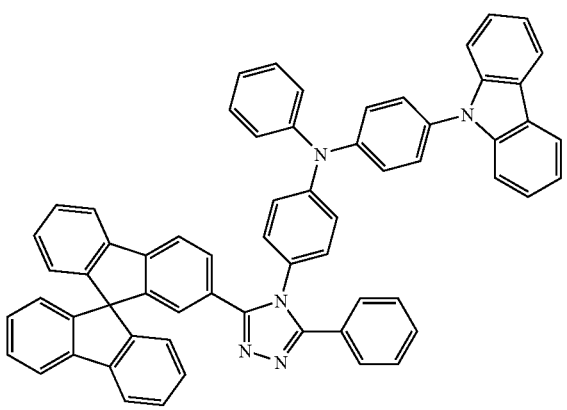
(155)
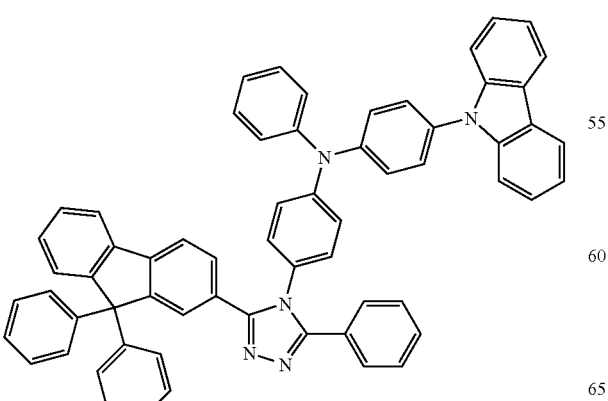
(156)
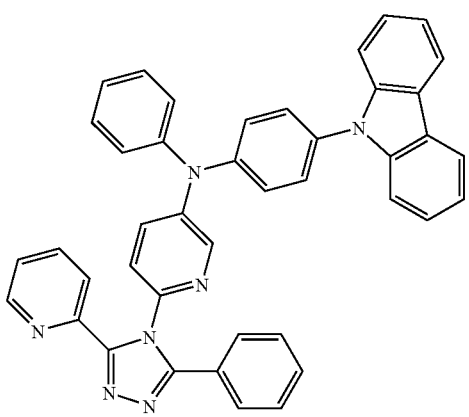
(157)
(158)
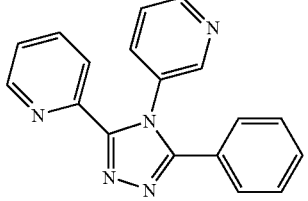
(159)
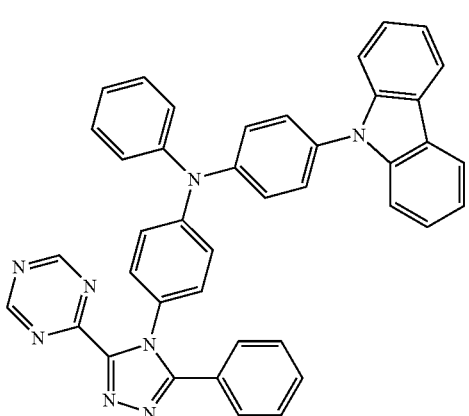

(160)
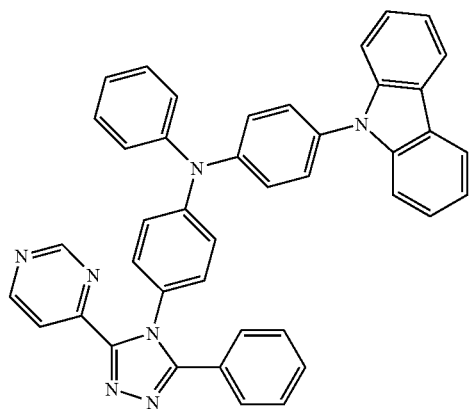
(161)
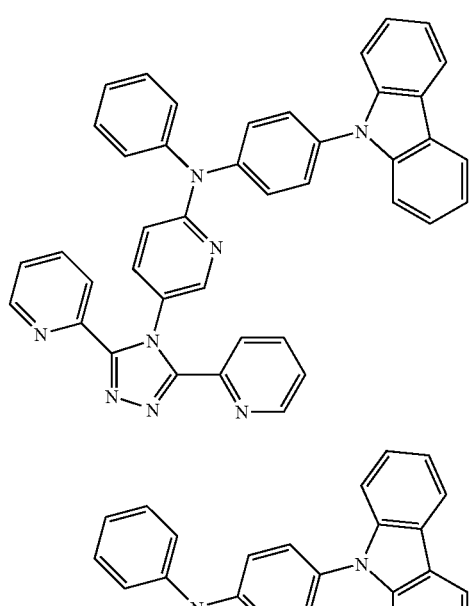
(162)
(163)
(164)
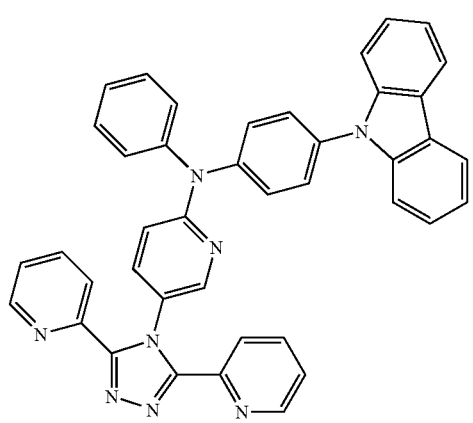
(165)
(166)
(167)
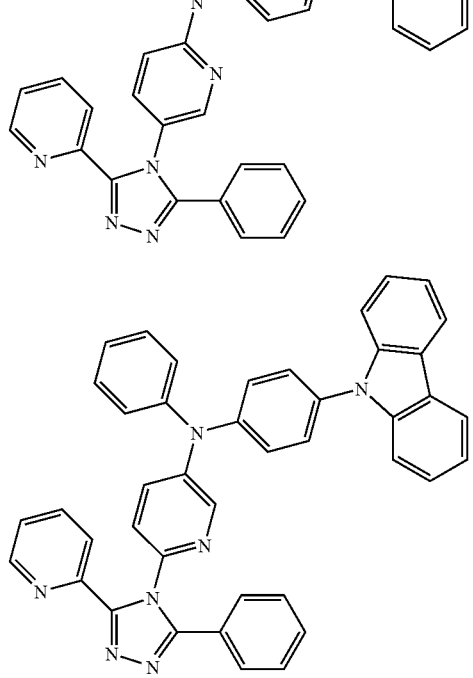

-continued
(168)
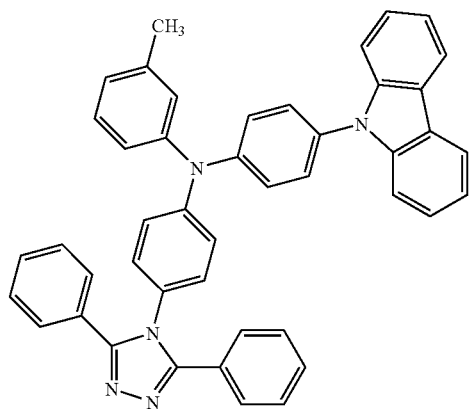
(169)
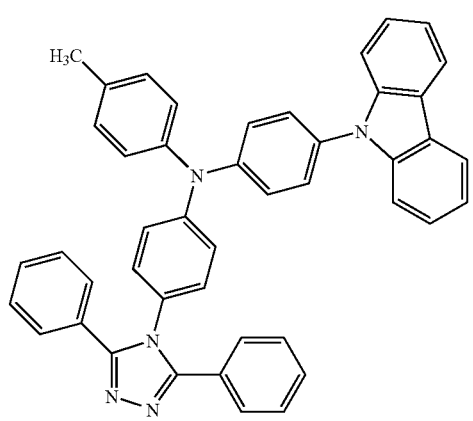
(170)
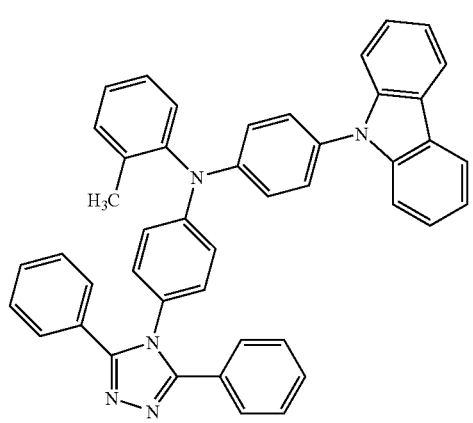
(171)
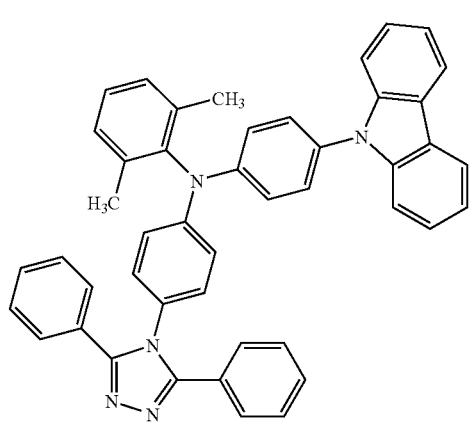
-continued
(172)
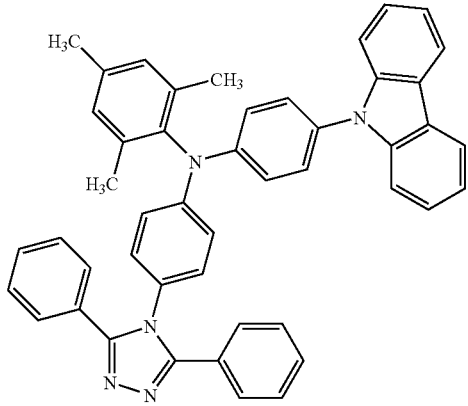
(173)
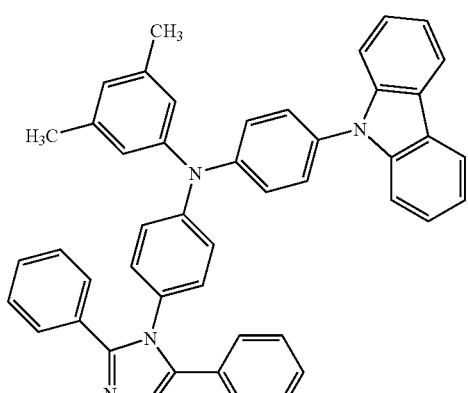
(174)
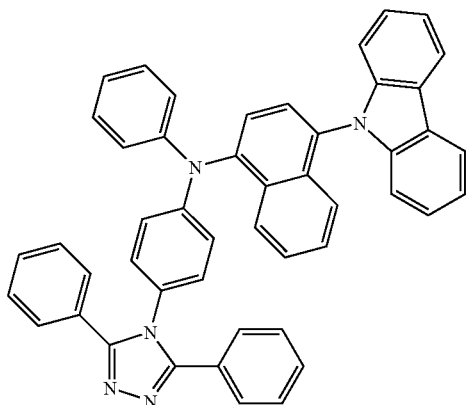
(175)
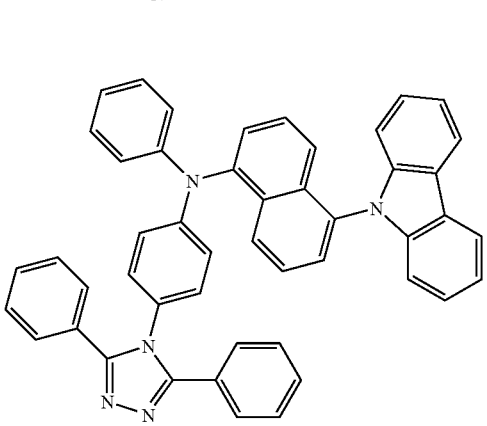

(176)
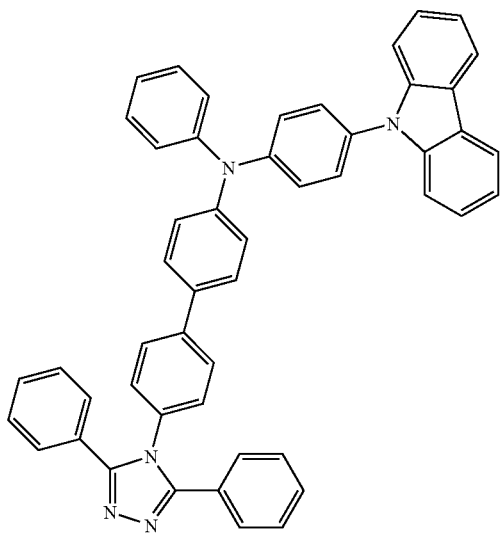
(177)
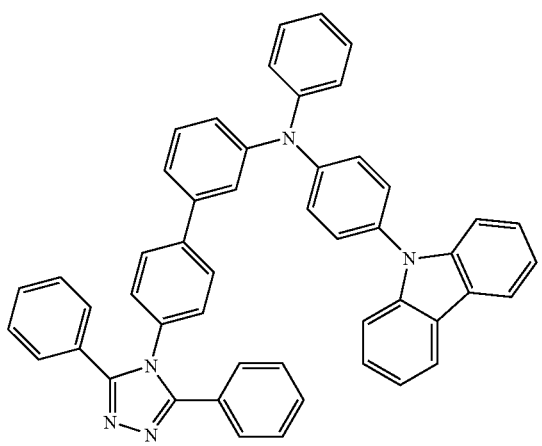
(178)
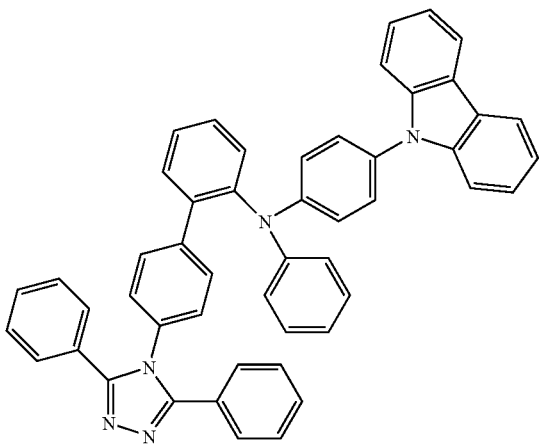
(179)
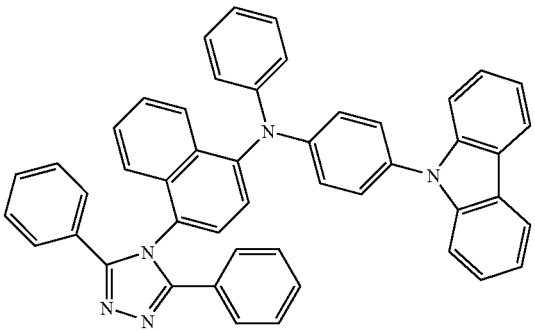
(180)
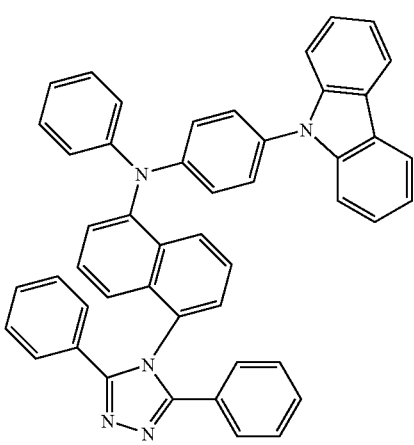
(181)
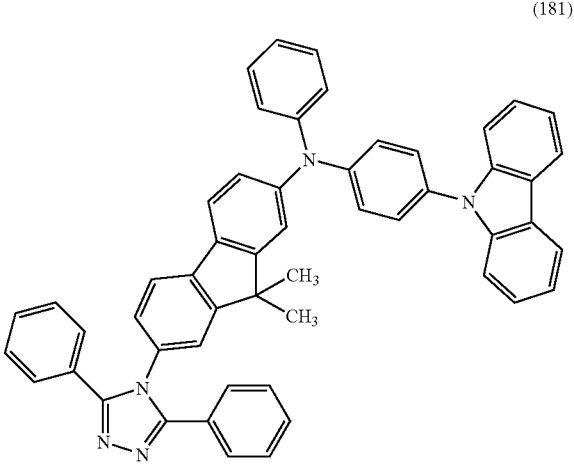

(182)
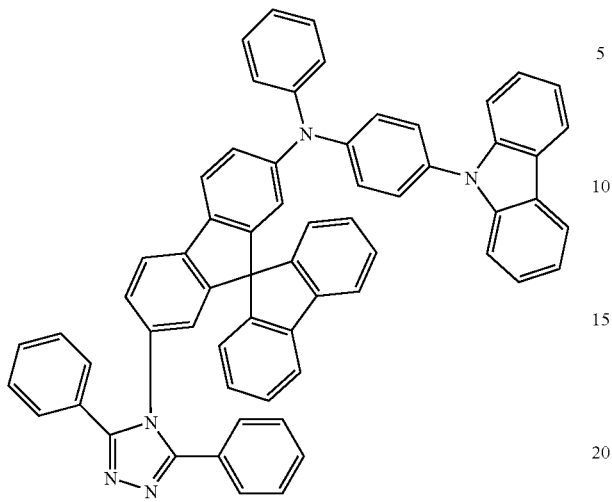
(183)
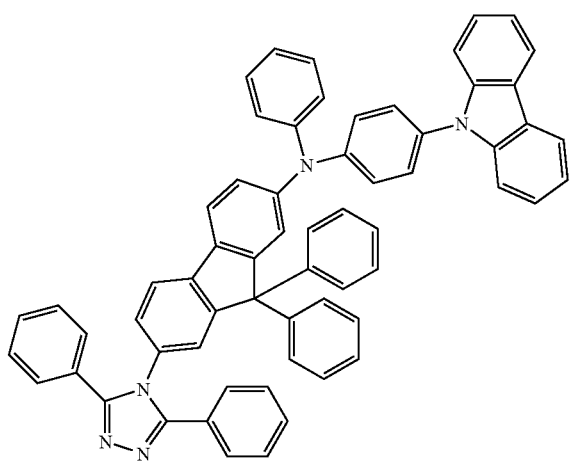
(184)
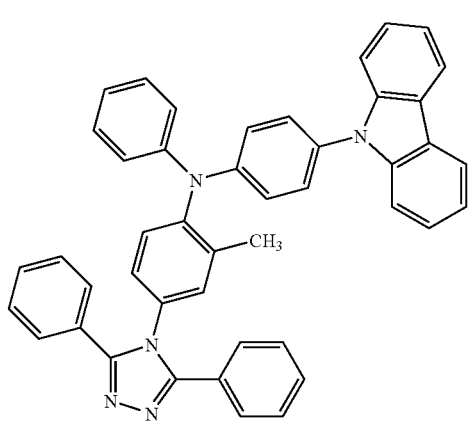
(185)
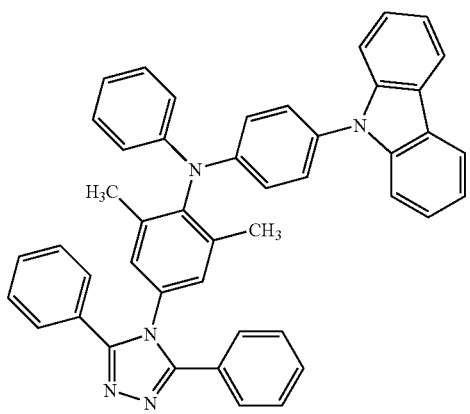
(186)
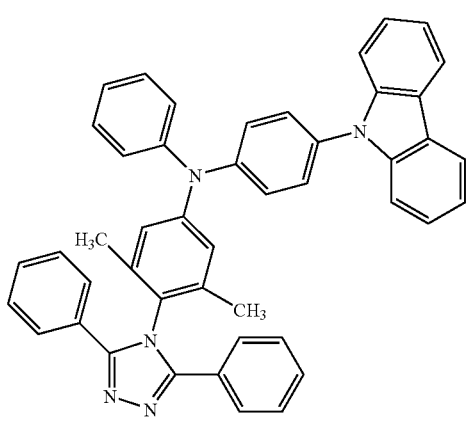
(187)
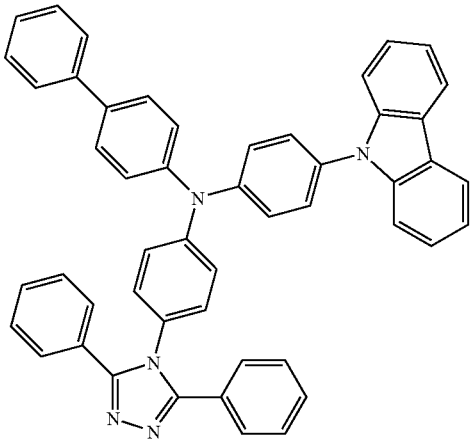

(188)
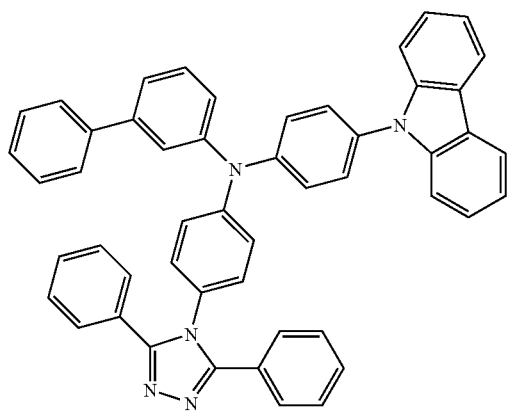
(189)
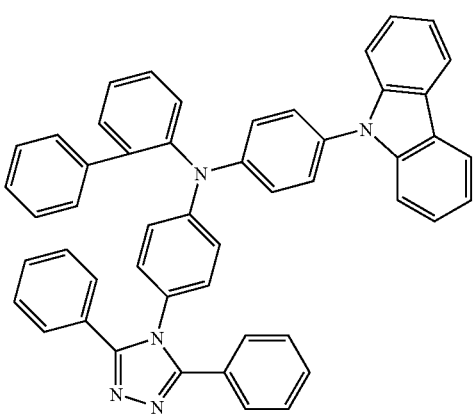
(190)
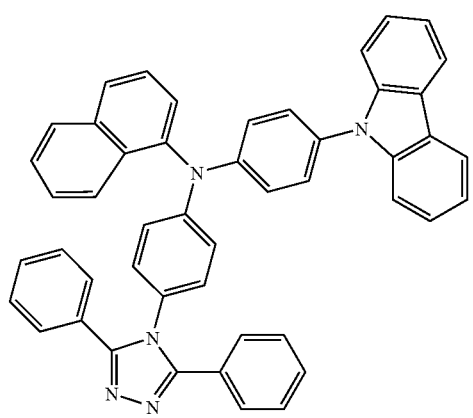
(191)
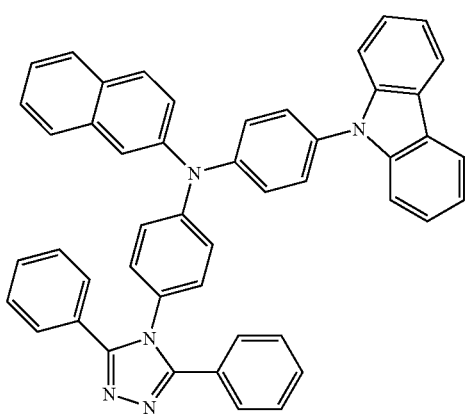
(192)
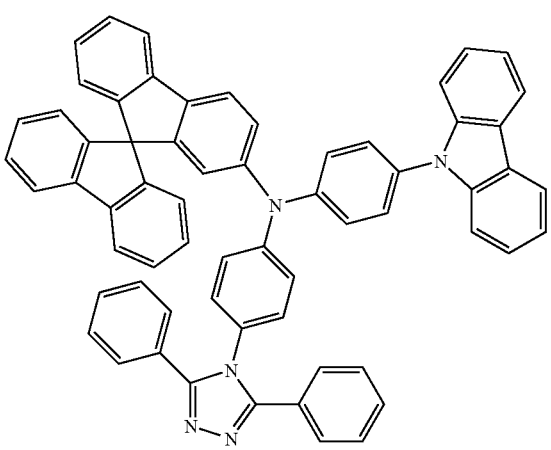
(193)
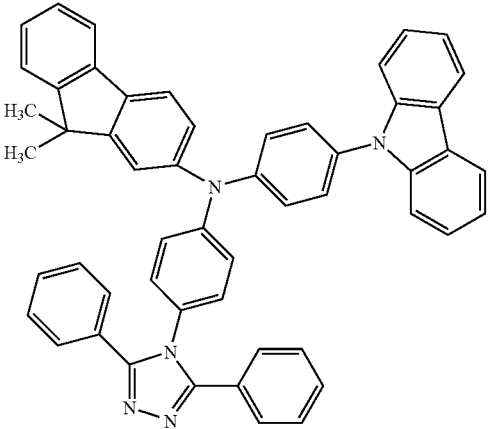

(194)
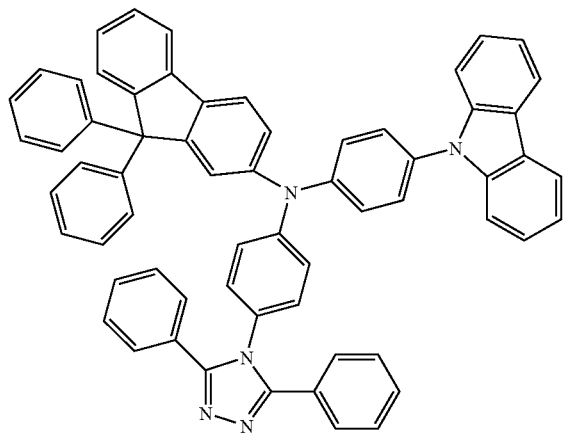

(195)
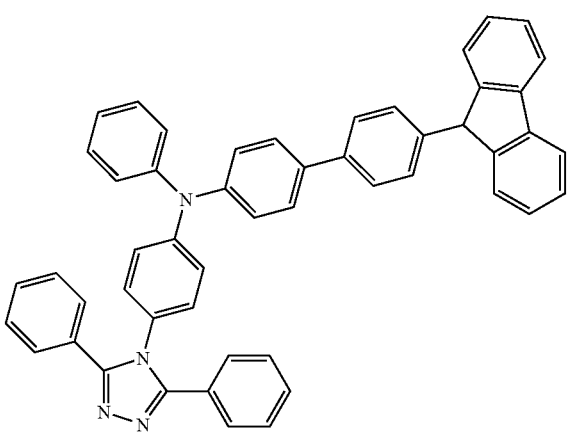

(196)
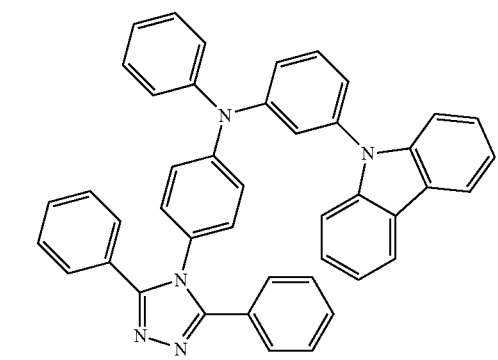

(197)
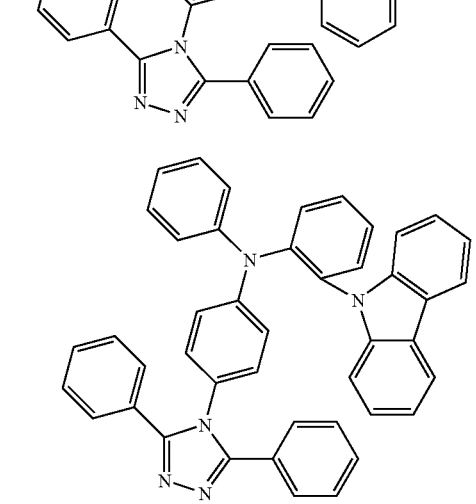

(198)
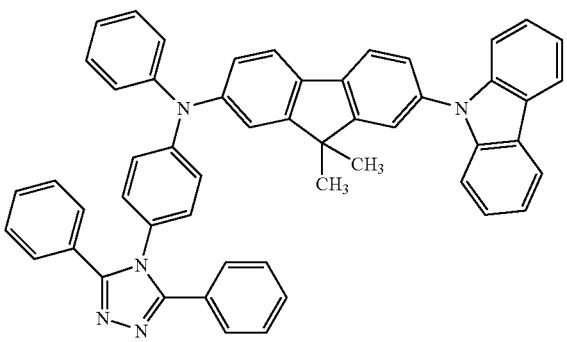

(199)
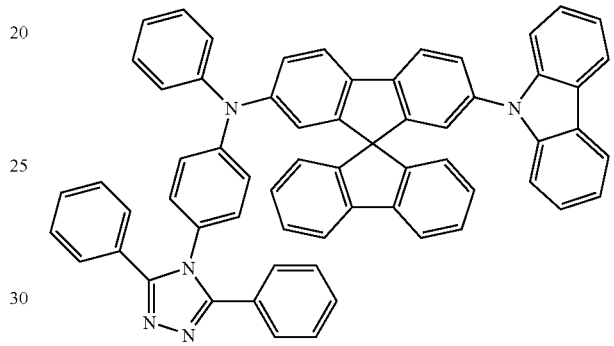

As a synthesis method of the triazole derivative of the present invention, any of a variety of reactions can be applied. For example, by synthesis reactions shown below, the triazole derivative of the present invention can be synthesized. Note that the synthesis method of the triazole derivative of the present invention is not limited to the synthesis methods below.

Synthesis Methods of Halogenated Triazole Derivatives (TAZ-1) and (TAZ-2)

Synthesis Method of Halogenated Triazole Derivative (TAZ-1)

A synthesis scheme of a halogenated triazole derivative (TAZ-1) is illustrated in (A-1).

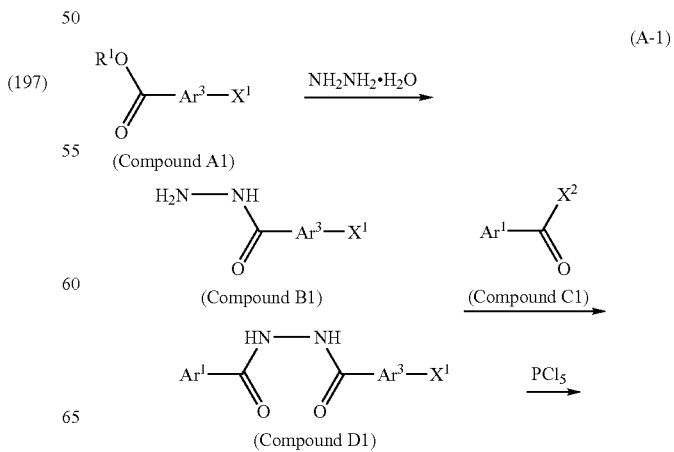

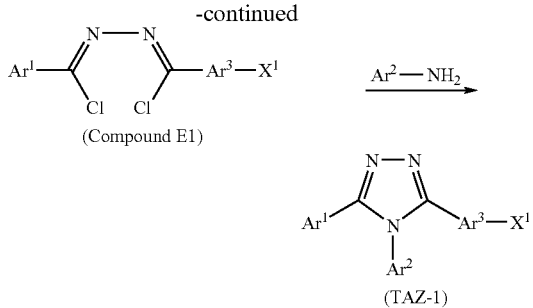

(Compound E1)

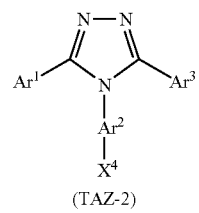

(TAZ-1)

First, by reaction of a compound A1 (halogenated aryl carboxylic acid ester or halogenated heteroaryl carboxylic acid ester) and hydrazine, a compound B1 (halogenated aryl hydrazide or halogenated heteroaryl hydrazide) is synthesized. Next, by reaction of the compound B1 (halogenated aryl hydrazide or halogenated heteroaryl hydrazide) and a compound C1 (aryl carboxylic acid halide or heteroaryl carboxylic acid halide), a compound D1 (a diacylhydrazine derivative) is obtained. Next, by reaction of the compound D1 (a diacylhydrazine derivative) and phosphorus pentachloride, a compound E1 (a hydrazone derivative) is obtained. Furthermore, by reaction of the compound E1 (the hydrazone derivative) and arylamine or heteroaryl, a 1,2,4-triazole ring is formed, so that the halogenated triazole derivative (TAZ-1) can be obtained.

In the synthesis scheme (A-1), $Ar^1$ and $Ar^2$ individually represent an aryl group having 6 to 25 carbon atoms or a heteroaryl group having 3 to 9 carbon atoms, $Ar^3$ represents an arylene group having 6 to 25 carbon atoms or a heteroarylene group having 3 to 9 carbon atoms, $R^1$ represents an alkyl group having 1 or 2 carbon atoms, and $X^1$ and $X^2$ individually represent a halogen group. $X^1$ is preferably a bromo group or an iodine group, and $X^2$ is preferably a chloro group.

Synthesis Method of Halogenated Triazole Derivative (TAZ-2)

A synthesis scheme of a halogenated triazole derivative (TAZ-2) is illustrated in (A-2).

(A-2)

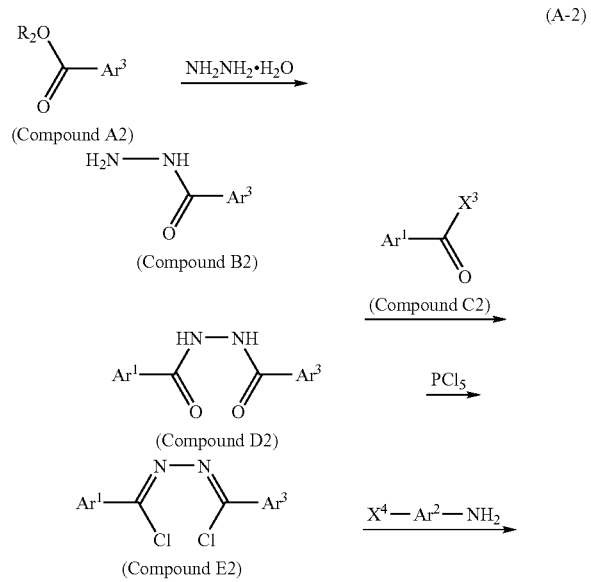

First, by reaction of a compound A2 (aryl carboxylic acid ester or heteroaryl carboxylic acid ester) and hydrazine, a compound B2 (aryl hydrazide or heteroaryl hydrazide) is synthesized. Next, by reaction of the compound B2 (aryl hydrazide or heteroaryl hydrazide) and a compound C2 (aryl carboxylic acid halide or heteroaryl carboxylic acid halide), a compound D2 (a diacylhydrazine derivative) is obtained. Next, by reaction of the compound D2 (the diacylhydrazine derivative) and phosphorus pentachloride, a compound E2 (a hydrazone derivative) is obtained. Furthermore, by reaction of the compound E2 (the hydrazone derivative) and halogenated arylamine or halogenated heteroaryl amine, a 1,2,4-triazole ring is formed, so that the halogenated triazole derivative (TAZ-2) can be obtained.

Note that in the synthesis scheme (A-2), $Ar^1$ and $Ar^3$ individually represent an aryl group or a heteroaryl group, $Ar^2$ represents an arylene group or a heteroarylene group, $R^2$ represents an alkyl group having 1 or 2 carbon atoms, and $X^3$ and $X^4$ individually represent a halogen group. $X^3$ is preferably a bromo group or an iodine group, and $X^4$ is preferably a chloro group.

Synthesis Method of Secondary Amine (Am-1)

The secondary amine represented by the above general formula (G2) can be synthesized by a synthesis scheme (B-1) below. In other words, first, by coupling of dihalogenated arene (a compound A3) with a carbazole derivative (a compound B3) in the presence of a base, using a metal catalyst, a halogenated aryl carbazole derivative (a compound B3) is synthesized. Next, by coupling of the halogenated aryl carbazole derivative (the compound B3) with arylamine (a compound D3) in the presence of a base, using a metal catalyst, the secondary amine (Am-1) can be obtained.

Note that in the synthesis scheme (B-1) below, α represents an arylene group having 6 to 25 carbon atoms, $Ar^4$ represents an aryl group having 6 to 25 carbon atoms, $R^1$ and $R^2$ individually represent hydrogen, an alkyl group having 1 to 4 carbon atoms, or an aryl group having 6 to 25 carbon atoms, and $X^3$ and $X^4$ individually represent a halogen group, preferably, a bromo group or an iodine group.

(B-1)

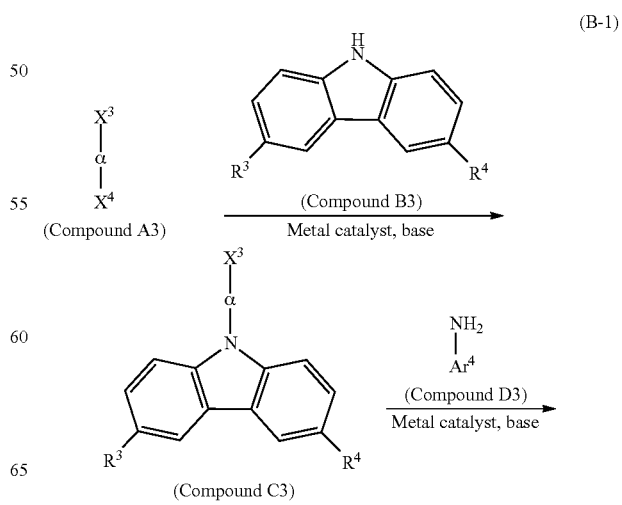

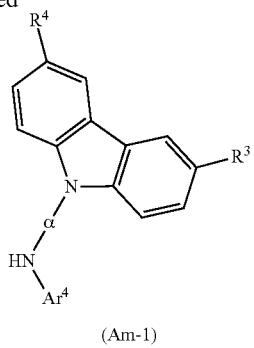

(Am-1)

Note that as the base, an inorganic base such as potassium carbonate or sodium carbonate, or an organic base typified by metal alkoxide such as sodium tert-butoxide can be used. Further, as the metal catalyst, there are a palladium compound, copper, a compound of monovalent copper, and the like. Specifically, there are palladium(II) acetate, bis(dibenzylideneacetone)palladium(0), copper, copper(I) iodide, copper(I) acetate, and the like.

Further, a method of the synthesizing the secondary amine (Am-1) is not limited to the above scheme (B-1), and other various methods can be used.

Synthesis Method of Triazole Derivative of the Present Invention

By coupling of either the halogenated triazole derivative (TAZ-1) obtained by the above synthesis scheme (A-1) or the halogenated triazole derivative (TAZ-2) obtained by the above synthesis scheme (A-2) with the secondary amine (Am-1) in the presence of a base, using a metal catalyst, the triazole derivative of the present invention can be obtained. This is illustrated in synthesis schemes (C-1) and (C-2).

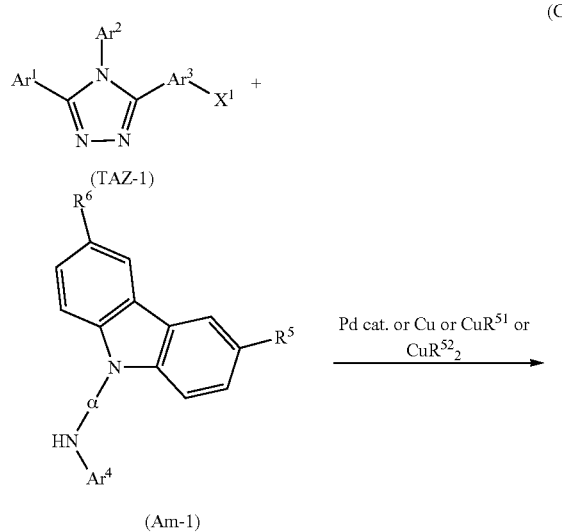

(C-1)

As illustrated in the synthesis scheme (C-1), by coupling of the secondary amine (Am-1) with the halogenated triazole derivative (TAZ-1) by a Hartwig-Buchwald reaction using a palladium catalyst or an Ullman reaction using copper or a copper compound, the triazole derivative of the present invention, which is represented by the general formula (G11), can be obtained.

In the synthesis scheme (C-1), $Ar^1$ and $Ar^2$ individually represent an aryl group having 6 to 25 carbon atoms or a heteroaryl group having 3 to 9 carbon atoms, $Ar^3$ represents an arylene group having 6 to 25 carbon atoms or a heteroarylene group having 3 to 9 carbon atoms, $Ar^4$ represents an aryl group having 6 to 25 carbon atoms, α represents an arylene group having 6 to 25 carbon atoms, $R^5$ and $R^6$ individually represent hydrogen, an aryl group having 6 to 25 carbon atoms, an alkyl group having 1 to 4 carbon atoms, or an alkoxy group having 1 to 4 carbon atoms, and $X^1$ and $X^2$ individually represent a halogen group. $X^1$ is preferably a bromo group or an iodine group, and $X^2$ is preferably a chloro group.

In the synthesis scheme (C-1), when a Hartwig-Buchwald reaction is performed, as the palladium catalyst that can be used, there are bis(dibenzylideneacetone)palladium(0), palladium(II) acetate, and the like, but the palladium catalyst that can be used is not limited thereto. As a ligand in the palladium catalyst that can be used in the synthesis scheme (C-1), there are tri(tert-butyl)phosphine, tri(n-hexyl)phosphine, tricyclohexylphosphine, and the like, but the ligand that can be used is not limited thereto. As a base that can be used in the synthesis scheme (C-1), there are an organic base such as sodium tert-butoxide, an inorganic base such as potassium carbonate, and the like, but the base that can be used is not limited thereto. As a solvent that can be used in the synthesis scheme (C-1), there are toluene, xylene, benzene, tetrahydrofuran, and the like, but the solvent that can be used is not limited thereto.

Further, the case in which an Ullmann reaction is performed in the synthesis scheme (C-1) is described. In the synthesis scheme (C-1), $R^{51}$ and $R^{52}$ individually represent halogen, an acetyl group, or the like. As halogen, there are chlorine, bromine, and iodine. Further, copper(I) iodide when $R^{51}$ is iodine or copper(II) acetate when $R^{52}$ is an acetyl group is preferable. The copper compound used for the reaction is not limited thereto. As an alternative to the copper compound, copper can be used. As the base that can be used in the synthesis scheme (C-1), there is an inorganic base such as potassium carbonate, but the base that can be used is not limited thereto. As the solvent that can be used in the synthesis scheme (C-1), there are 1,3-dimethyl-3,4,5,6-tetrahydro-2(1H)pyrimidinone (DMPU), toluene, xylene, benzene, and the like, but the solvent that can be used is not limited thereto. In an Ullmann reaction, when reaction temperature is 100° C. or more, the object of the synthesis can be obtained in a shorter time at a higher yield; therefore, DMPU or xylene, which has a high boiling point, is preferably used. Since the reaction temperature is further preferably 150° C. or more, DMPU is more preferably used.

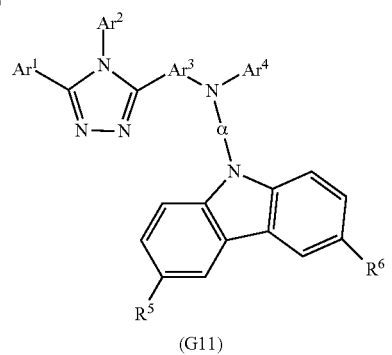

(C-2)

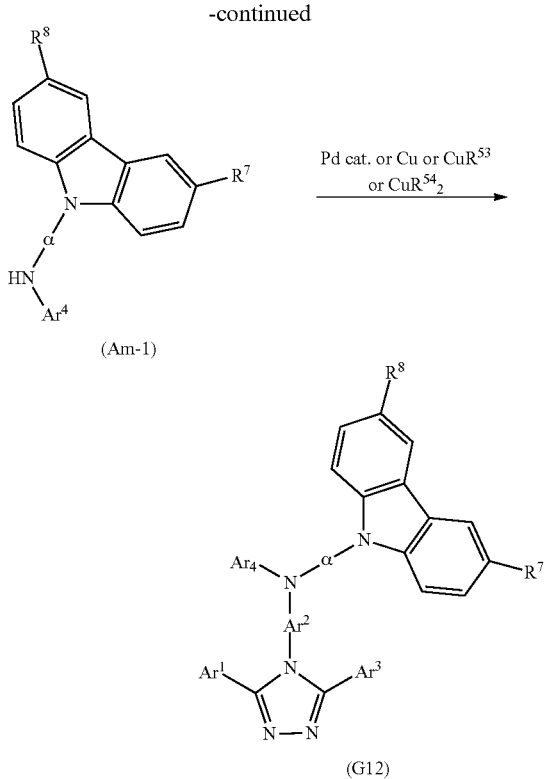

(Am-1)

(G12)

As illustrated in the synthesis scheme (C-2), by coupling of the secondary amine (Am-1) with the halogenated triazole derivative (TAZ-2) by a Hartwig-Buchwald reaction using a palladium catalyst or an Ullman reaction using copper or a copper compound, the triazole derivative of the present invention, which is represented by the general formula (G12), can be obtained.

In the synthesis scheme (C-2), $Ar^1$ and $Ar^3$ individually represent an aryl group having 6 to 25 carbon atoms or a heteroaryl group having 3 to 9 carbon atoms, $Ar^2$ represents an arylene group having 6 to 25 carbon atoms or a heteroarylene group having 3 to 9 carbon atoms, $Ar^4$ represents an aryl group having 6 to 25 carbon atoms, α represents an arylene group having 6 to 25 carbon atoms, $R^7$ and $R^8$ individually represent hydrogen, an aryl group having 6 to 25 carbon atoms, an alkyl group having 1 to 4 carbon atoms, or an alkoxy group having 1 to 4 carbon atoms, and $X^3$ and $X^4$ individually represent a halogen group. $X^3$ is preferably a bromo group or an iodine group, and $X^4$ is preferably a chloro group.

In the synthesis scheme (C-2), when a Hartwig-Buchwald reaction is performed, as the palladium catalyst that can be used, there are bis(dibenzylideneacetone)palladium(0), palladium(II) acetate, and the like, but the palladium catalyst that can be used is not limited thereto. As a ligand in the palladium catalyst that can be used in the synthesis scheme (C-2), there are tri(tert-butyl)phosphine, tri(n-hexyl)phosphine, tricyclohexylphosphine, and the like, but the ligand that can be used is not limited thereto. As a base in the palladium catalyst that can be used in the synthesis scheme (C-2), there are an organic base such as sodium tert-butoxide, an inorganic base such as potassium carbonate, and the like, but the base that can be used is not limited thereto. As a solvent in the palladium catalyst that can be used in the synthesis scheme (C-2), there are toluene, xylene, benzene, tetrahydrofuran, and the like, but the solvent that can be used is not limited thereto.

The case in which an Ullmann reaction is performed in the synthesis scheme (C-2) is described. In the synthesis scheme (C-2), $R^{53}$ and $R^{54}$ individually represent halogen, an acetyl group, or the like. As halogen, there are chlorine, bromine, and iodine. Further, copper(I) iodide when $R^{53}$ is iodine or copper(II) acetate when $R^{54}$ is an acetyl group is preferable. The copper compound used for the reaction is not limited thereto. As an alternative to the copper compound, copper can be used. As a base in the palladium catalyst that can be used in the synthesis scheme (C-2), there is an inorganic base such as potassium carbonate, but the base that can be used is not limited thereto. As a solvent in the palladium catalyst that can be used in the synthesis scheme (C-2), there are 1,3-dimethyl-3,4,5,6-tetrahydro-2(1H)pyrimidinone (DMPU), toluene, xylene, benzene, and the like, but the solvent that can be used is not limited thereto. In an Ullmann reaction, when reaction temperature is 100° C. or more, the object of the synthesis can be obtained in a short time at a high yield; therefore, DMPU or xylene that has a high boiling point is preferably used. Since the reaction temperature is further preferably 150° C. or more, DMPU is more preferably used.

The triazole derivative of the present invention has high triplet excitation energy, and an electron-transporting property and a hole-transporting property. Accordingly, the triazole derivative of the present invention can be preferably used for a light-emitting element. Since the balance between injected electrons and holes is important particularly for a light-emitting layer of a light-emitting element, the triazole derivative of the present invention is more preferably used for a light-emitting layer. Further, having high triplet excitation energy, the triazole derivative of the present invention can be used for a light-emitting layer, along with a substance that emits phosphorescence.

Further, since the singlet excitation energy (an energy difference between a ground state and a singlet excited state) is higher than the triplet excitation energy, a substance having high triplet excitation energy also has high singlet excitation energy. Therefore, the triazole derivative of the present invention having high triplet excitation energy is useful even in the case of being used for a light-emitting layer, along with a substance that emits fluorescence.

Further, the triazole derivative of the present invention can transport carriers, and therefore can be used for a carrier-transporting layer in a light-emitting element. In particular, the triazole derivative of the present invention has high triplet excitation energy; therefore, energy transfer from a light-emitting layer does not easily occur even when the triazole derivative of the present invention is used for a layer in contact with the light-emitting layer. Accordingly, high emission efficiency can be achieved.

Embodiment Mode 2

In Embodiment Mode 2, one mode of a light-emitting element using the triazole derivative of the present invention is described using FIG. 1.

The light-emitting element of the present invention has a plurality of layers between a pair of electrodes. The plurality of layers are a stack of layers each including a substance having a high carrier-injecting property or a substance having a high carrier-transporting property such that a light-emitting region is formed in a region away from the electrodes, i.e., such that carriers recombine in an area away from the electrodes.

In FIG. 1, the light-emitting element of this embodiment mode includes a first electrode 101, a second electrode 102, and a layer 103 containing an organic compound provided between the first electrode 101 and the second electrode 102. Note that in this embodiment mode, hereinafter, it is assumed that the first electrode 101 functions as an anode and the second electrode 102 functions as a cathode. In other words, in the description below, it is assumed that light emission is obtained when a voltage is applied to the first electrode 101 and the second electrode 102 so that the potential of the first electrode 101 is higher than that of the second electrode 102.

A substrate 100 is used as a support of the light-emitting element. For the substrate 100, glass, plastic, or the like may be used, for example. Note that any other material may be used as long as it functions as a support in a manufacturing process.

It is preferable that the first electrode 101 be formed using a metal, an alloy, or a conductive compound, a mixture thereof, or the like having a high work function (specifically greater than or equal to 4.0 eV). Specifically, for example, there are indium oxide-tin oxide (ITO), indium oxide-tin oxide containing silicon or silicon oxide, indium oxide-zinc oxide (IZO), indium oxide containing tungsten oxide and zinc oxide (IWZO), and the like. Such conductive metal oxide films are normally formed by sputtering, but may also be formed by applying a sol-gel method or the like. For example, a film of indium oxide-zinc oxide (IZO) can be formed using a target in which 1 wt % to 20 wt % of zinc oxide is added to indium oxide by a sputtering method. In addition, a film of indium oxide containing tungsten oxide and zinc oxide (IWZO) can be formed using a target in which 0.5 wt % to 5 wt % tungsten oxide and 0.1 wt % to 1 wt % zinc oxide are added to indium oxide by a sputtering method. Further, there are gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), and the like.

There is no particular limitation on the stack structure of the layer 103 containing an organic compound. The layer 103 containing an organic compound may have a structure in which a layer that contains a substance having a high electron-transporting property, a layer that contains a substance having a high hole-transporting property, a layer that contains a substance having a high electron-injecting property, a layer that contains a substance having a high hole-injecting property, a layer containing a bipolar substance (a substance having a high electron-transporting and a high hole-transporting property), or the like is used in combination with the light-emitting layer described in this embodiment mode, as appropriate. For example, a hole-injecting layer, a hole-transporting layer, a light-emitting layer, an electron-transporting layer, an electron-injecting layer, or the like can be used in combination as appropriate. Materials for forming the layers are specifically given below.

A hole-injecting layer 111 is a layer that contains a substance having a high hole-injecting property. Molybdenum oxide, vanadium oxide, ruthenium oxide, tungsten oxide, manganese oxide, or the like can be used. Alternatively, the hole-injecting layer can be formed of a phthalocyanine compound such as phthalocyanine ($H_2Pc$) or copper phthalocyanine (CuPc), a high molecular substance such as poly(3,4-ethylenedioxythiophene)/poly(styrenesulfonic acid) (PEDOT/PSS), or the like.

Alternatively, the hole-injecting layer can be formed of a composite material in which an acceptor substance is mixed into a substance having a high hole-transporting property. Note that by using the composite material in which an acceptor substance is mixed into a substance having a high hole-transporting property, a material for forming the electrode can be selected regardless of the electrode. That is, not only a high-work function material, but also a low-work function material can be used for the first electrode 101. As the acceptor substance, there are 7,7,8,8-tetracyano-2,3,5,6-tetrafluoroquinodimethane (abbreviation: $F_4$-TCNQ), chloranil, and the like. Further, there are transition metal oxides. Furthermore, there are oxides of metals that belong to Group 4 to Group 8 of the periodic table. Specifically, any of vanadium oxide, niobium oxide, tantalum oxide, chromium oxide, molybdenum oxide, tungsten oxide, manganese oxide, or rhenium oxide is preferably used because of their high electron accepting property. In particular, molybdenum oxide is more preferable because of its stability in the atmosphere, low hygroscopic property, and easiness of handling.

Note that in this specification, being composite refers not only to a state in which two materials are simply mixed but also to a state in which charges can be transferred between a plurality of materials by mixture of the materials.

As the substance having a high hole-transporting property, which is used for the composite material, any of a variety of compounds such as aromatic amine compounds, carbazole derivatives, aromatic hydrocarbons, or high molecular compounds (e.g., oligomers, dendrimers, or polymers) can be used. Note that a substance having a hole mobility of $10^{-6}$ $cm^2/Vs$ or more is preferably used as the substance having a high hole-transporting property, which is used for the composite material. However, any other substance may also be used as long as it is a substance in which the hole-transporting property is higher than the electron-transporting property. Hereinafter, organic compounds that can be used for the composite material are specifically given.

For example, as an aromatic amine compound that can be used for the composite material, there are N,N'-bis(4-methylphenyl)(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), and the like.

As a carbazole derivative that can be used for the composite material, specifically, there are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphtyl)-N-(9-phenylcarbazol-3-yl)amino]-9-phenylcarbazole (abbreviation: PCzPCN1), and the like.

Further, as a carbazole derivative that can be used for the composite material, there are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Further, as an aromatic hydrocarbon that can be used for the composite material, for example, there are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butyl-anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'- bis[(2,3,4,5,6-pentaphenyl)phenyl]-9,9'-bianthryl, anthracene, tetracene, rubrene, perylene, 2,5,8,11-tetra(tert-butyl)perylene, and the like. Alternatively, pentacene, coronene, or the like can be used. As described above, an aromatic hydrocarbon that has a hole mobility of $1\times10^{-6}$ cm$^2$/Vs or more and 14 to 42 carbon atoms is more preferably used.

Note that an aromatic hydrocarbon that can be used for the composite material may have a vinyl skeleton. As an aromatic hydrocarbon having a vinyl skeleton, for example, there are 4,4'-bis(2,2-diphenylvinyl)biphenyl (abbreviation: DPVBi) 9,10-bis[4-(2,2-diphenylvinyl)phenyl]anthracene (abbreviation: DPVPA), and the like.

Alternatively, for the hole-injecting layer 111, any of high molecular compounds (e.g., oligomers, dendrimers, or polymers) can be used. For example, there are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl) benzidine] (abbreviation: Poly-TPD). Alternatively, a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS) can be used.

Alternatively, the composite material may be formed using the above-described high molecular compound, such as PVK, PVTPA, PTPDMA, or Poly-TPD, and the above-described acceptor substance to be used for the hole-injecting layer 111.

A hole-transporting layer 112 is a layer that contains a substance having a high hole-transporting property. As the substance having a high hole-transporting property, it is possible to use, for example, an aromatic amine compound such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), or 4,4'-bis[N-(spiro-9,9'-bifluoren-2-yl)-N-phenylamino]biphenyl (abbreviation: BSPB), or the like. The substances given here are mainly substances each having a hole mobility of $10^{-6}$ cm$^2$/Vs or more. Note that any other substance may also be used as long as it is a substance in which the hole-transporting property is higher than the electron-transporting property. Note that the layer that contains a substance having a high hole-transporting property is not limited to a single layer, and may be a stack of two or more layers each containing any of the above-described substances.

Alternatively, for the hole-transporting layer 112, a high molecular compound such as PVK, PVTPA, PTPDMA, or Poly-TPD can be used.

Note that for the hole-transporting layer in contact with the light-emitting layer, a substance having excitation energy higher than that of a light-emitting substance of the light-emitting layer is preferably used. Specifically, when the light-emitting substance is a fluorescent compound, a substance having singlet excitation energy higher than that of the fluorescent compound is preferably used for the hole-transporting layer. Alternatively, when the light-emitting substance is a phosphorescent compound, a substance having triplet excitation energy higher than that of the phosphorescent compound is preferably used for the hole-transporting layer. With such structures, energy transfer from the light-emitting layer to the hole-transporting layer can be suppressed, and high emission efficiency can be achieved. As a substance having high triplet excitation energy, in which the hole-transporting property is higher than the electron-transporting property, there are 4,4',4''-tri(N-carbazolyl)triphenylamine (abbreviation: TCTA), 1,1-bis[4-(diphenylamino)phenyl]cyclohexane (abbreviation: TPAC), 9,9-bis[4-(diphenylamino)phenyl]fluorene (abbreviation: TPAF), 4,4'-di(N-carbazolyl)biphenyl (abbreviation: CBP), and the like.

A light-emitting layer 113 is a layer that contains a substance having a high light-emitting property. The light-emitting layer 113 can be formed using the triazole derivative described in Embodiment Mode 1. Emitting purple light, the triazole derivative described in Embodiment Mode 1 can be used for the light-emitting layer, as the substance having a high light-emitting property.

Alternatively, a structure can be employed in which the substance having a high light-emitting property is dispersed in the triazole derivative described in Embodiment Mode 1. Since the triazole derivative described in Embodiment Mode 1 has high triplet excitation energy and high singlet excitation energy, it is particularly preferable to employ the structure in which the substance having a high light-emitting property is dispersed in the triazole derivative described in Embodiment Mode 1.

As the substance having a high light-emitting property, which is dispersed in the triazole derivative described in Embodiment Mode 1, a substance that emits fluorescence or a substance that emits phosphorescence can be used.

When a substance that emits phosphorescence (a phosphorescent compound) is used, a substance having triplet excitation energy lower than that of the triazole derivative described in Embodiment Mode 1 is preferably used. Since the triazole derivative described in Embodiment Mode 1 has high triplet excitation energy, the selection range of the phosphorescent compound used for the light-emitting layer is extended. In particular, high emission efficiency can be achieved even in the case where the triazole derivative described in Embodiment Mode 1 is used for the light-emitting layer, along with a substance that emits phosphorescence exhibiting light emission (blue light emission) at a short wavelength greater than or equal to 400 nm and less than or equal to 500 nm.

As the substance that emits phosphorescence, which can be used for the light-emitting layer along with the triazole derivative described in Embodiment Mode 1, any of the materials below can be used. For example, as a blue light-emitting material, there are bis[2-(4',6'-difluorophenyl)pyridinato-N, C$^{2'}$]iridium(III)tetrakis(1-pyrazolyl)borate (abbreviation: FIr6), bis[2-(4',6'-difluorophenyl)pyridinato-N,C$^{2'}$]iridium(III)picolinate (abbreviation: FIrpic), bis[2-(3',5'-bistrifluoromethyl)pyridinato-N,C]$^{2'}$}iridium(III)picolinate (abbreviation: Ir(CF$_3$ ppy)$_2$(pic)), bis[2-(4',6'-difluorophenyl) pyridinato-N,C$^{2'}$]iridium(III)acetylacetonate (abbreviation: FIr(acac)), and the like. Further, as a green light-emitting material, there are tris(2-phenylpyridinato-N,C$^{2'}$)iridium(III) (abbreviation: Ir(Ppy)$_3$), bis(2-phenylpyridinato-N,C$^{2'}$)iridium(III)acetylacetonate (abbreviation: Ir(Ppy)$_2$(acac)), bis (1,2-diphenyl-1H-benzimidazolato)iridium(III)acetylacetonate (abbreviation: Ir(pbi)$_2$(acac)), bis(benzo[h]quinolinato) iridium(III)acetylacetonate (abbreviation: Ir(bzq)$_2$(acac)), and the like. Further, as a yellow light-emitting material, there are bis(2,4-diphenyl-1,3-oxazolato-N,C$^{2'}$)iridium(III)acetylacetonate (abbreviation: Ir(dpo)$_2$(acac)), bis[2-(4'-perfluorophenylphenyl)pyridinato]iridium(III)acetylacetonate (abbreviation: Ir(p-PF-ph)$_2$(acac)), bis(2-phenylbenzothiazolato-N,C$^{2'}$)iridium(III)acetylacetonate (abbreviation: Ir(bt)$_2$(acac)), and the like. Further, as an orange light-emitting material, there are tris(2-phenylquinolinato-N,C$^{2'}$)iridium(III) (abbreviation: Ir(pq)$_3$), bis(2-phenylquinolinato-N,C$^{2'}$)iridium(III)acetylacetonate (abbreviation: Ir(pq)$_2$(acac)), and the like. Further, as a red light-emitting material, there are organometallic complexes such as bis[2-(2'-benzo[4,5-α]thienyl)pyridinato-N,C)$^{3'}$)iridium (III)acetylacetonate (abbreviation: Ir(btp)$_2$(acac)), bis(1-phenylisoquinolinato-N,C$^{2'}$)iridium(III)acetylacetonate (abbreviation: Ir(piq)$_2$(acac)), and (acetylacetonato)bis[2,3-bis(4-fluorophenyl)quinoxalinato]iridium(III) (abbreviation: Ir(Fdpq)$_2$(acac)), and (2,3,7,8,12,13,17,18-octaethyl-21H,23H-porphyrine)platinum(II) (abbreviation: PtOEP). In addition, a rare-earth metal complex such as tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), or tris[1-(2-thenoyl)-3,3,3-trifluoroacetonato](monophenanthroline)europium(III) (abbreviation: Eu(TTA)$_3$(Phen)) performs light emission (electron transition between different multiplets) from a rare-earth metal ion; therefore, such a rare-earth metal complex can be used as a phosphorescent compound.

When a substance that emits fluorescence is used, a substance having singlet excitation energy lower than that of the triazole derivative described in Embodiment Mode 1 is preferably used. Since the triazole derivative described in Embodiment Mode 1 has high singlet excitation energy, the selection range of the fluorescent compound used for the light-emitting layer is extended.

As a fluorescent compound that can be used for the light-emitting layer, along with the triazole derivative described in Embodiment Mode 1, any of the materials below can be used. For example, as a blue light-emitting material, there are N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and the like. Further, as a green light-emitting material, there are N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Further, as a yellow light-emitting material, there are rubrene, 5,12-bis(1,1'-biphenyl-4-yl)-6,11-diphenyltetracene (abbreviation: BPT), and the like. Further, as a red light-emitting material, there are N,N,N',N'-tetrakis(4-methylphenyl)tetracene-5,11-diamine (abbreviation: p-mPhTD), 7,13-diphenyl-N,N,N',N'-tetrakis(4-methylphenyl)acenaphtho[1,2-a]fluoranthene-3,10-diamine (abbreviation: p-mPhAFD), and the like.

An electron-transporting layer 114 is a layer that contains a substance having a high electron-transporting property. For example, a metal complex or the like having a quinoline or benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq) can be used. Alternatively, a metal complex or the like having an oxazole-based or thiazole-based ligand, such as bis[2-(2'-hydroxyphenyl)benzoxazolato]zinc (abbreviation: Zn(BOX)$_2$) or bis[2-(2'-hydroxyphenyl)benzothiazolato]zinc (abbreviation: Zn(BTZ)$_2$) can be used. As an alternative to the metal complex, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), bathophenanthroline (abbreviation: BPhen), bathocuproine (abbreviation: BCP), or the like can be used. The substances given here are mainly substances each having an electron mobility of $10^{-6}$ cm$^2$/Vs or more. However, any other substance may also be used as long as it is a substance in which the electron-transporting property is higher than the hole-transporting property. Furthermore, the electron-transporting layer is not limited to a single layer, and may be a stack of two or more layers each containing any of the above-described substances.

Alternatively, for the electron-transporting layer 114, a high molecular compound can be used. For example, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy), or the like can be used.

Note that for the electron-transporting layer in contact with the light-emitting layer, a substance having excitation energy higher than that of the light-emitting substance of the light-emitting layer is preferably used. Specifically, when the light-emitting substance is a fluorescent compound, a substance having singlet excitation energy higher than that of the fluorescent compound is preferably used for the electron-transporting layer. Alternatively, when the light-emitting substance is a phosphorescent compound, a substance having triplet excitation energy higher than that of the phosphorescent compound is preferably used for the electron-transporting layer. With such structures, energy transfer from the light-emitting layer to the electron-transporting layer can be suppressed, and high emission efficiency can be achieved. As a substance having high triplet excitation energy, in which the electron-transporting property is higher than the hole-transporting property, there are 3-(4-biphenylyl)-4-phenyl-5-(4-tert-butylphenyl)-1,2,4-triazole (abbreviation: TAZ01), 2,2',2"-(1,3,5-benzenetriyl)tris(1-phenyl-1H-benzimidazole) (abbreviation: TPBI), 3-(4'-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), 9,9',9"-[1,3,5-triazine-2,4,6-triyl]tricarbazole (abbreviation: TCzTRZ), and the like.

Further, an electron-injecting layer 115 may be provided. The electron-injecting layer 115 can be formed using an alkali metal compound or an alkaline earth metal compound such as lithium fluoride (LiF), cesium fluoride (CsF), or calcium fluoride (CaF$_2$). Furthermore, a layer in which a substance having an electron-transporting property is combined with an alkali metal or an alkaline earth metal can be employed. For example, it is possible to use a layer in which magnesium (Mg) is contained in Alq. It is more preferable to use the layer in which a substance having an electron-transporting property is combined with an alkali metal or an alkaline earth metal as the electron-injecting layer, because electrons are efficiently injected from the second electrode 102.

As a substance forming the second electrode 102, a metal, an alloy, or a conductive compound, a mixture of them, or the like having a low work function (specifically less than or equal to 3.8 eV) can be used. As specific examples of such cathode materials, there are elements belonging to Group 1 and Group 2 of the periodic table, that is, alkali metals such as lithium (Li) or cesium (Cs), alkaline earth metals such as magnesium (Mg), calcium (Ca), or strontium (Sr), or alloys thereof (e.g., MgAg or AlLi), rare earth metals such as europium (Eu) or ytterbium (Yb), or alloys thereof, and the like. Films containing an alkali metal, an alkaline earth metal, or an alloy thereof can be formed by a vacuum evaporation method. Alternatively, films containing an alkali metal, an alkaline earth metal, or an alloy thereof can be formed by a sputtering method. Further alternatively, a film can be formed of a silver paste by an inkjet method or the like.

Further, by providing the electron-injecting layer 115 between the second electrode 102 and the electron-transporting layer 114, any of a variety of conductive materials such as Al, Ag, ITO, or indium oxide-tin oxide containing silicon or silicon oxide can be used for the second electrode 102 regardless of the work function. These conductive materials can be formed by a sputtering method, an inkjet method, a spin coating method, or the like.

Further, any of a variety of methods can be employed for forming the layer 103 containing an organic compound regardless of a dry process or a wet process. For example, a vacuum evaporation method, an inkjet method, a spin-coating method, or the like may be used. Further, formation methods, which are different for each electrode or each layer, may be used.

The electrodes may also be formed by a wet process using a sol-gel method or by a wet process using a metal paste. Alternatively, the electrodes may be formed by a dry process such as a sputtering method or a vacuum evaporation method.

Hereinafter, specific methods of forming the light-emitting element are described. For example, when the light-emitting element of the present invention is applied to a display device and manufactured using a large substrate, the light-emitting layer is preferably formed by a wet process. By forming the light-emitting layers by an inkjet method, the light-emitting layers are easy to form separately for each color even when a large substrate is used.

For example, the structure described in this embodiment mode may be formed as follows: the first electrode is formed by a sputtering method which is a dry process, the hole-injecting layer is formed by an inkjet method or a spin coating method which is a wet process, the hole-transporting layer is formed by a vacuum evaporation method which is a dry process, the light-emitting layer is formed by an inkjet method which is a wet process, the electron-injecting layer is formed by a vacuum evaporation method which is a dry process, and the second electrode is formed by an inkjet method or a spin coating method which is a wet process. Alternatively, the structure may be formed as follows: the first electrode is formed by an inkjet method which is a wet process, the hole-injecting layer is formed by a vacuum evaporation method which is a dry process, the hole-transporting layer is formed by an inkjet method or a spin coating method which is a wet process, the light-emitting layer is formed by an inkjet method which is a wet process, the electron-injecting layer is formed by an inkjet method or a spin coating method which is a wet process, and the second electrode is formed by an inkjet method or a spin coating method which is a wet process. Note that there is no limitation on the method of forming the light-emitting element and that a wet process and a dry process may be used in combination as appropriate.

Alternatively, for example, the light-emitting element can be formed as follows: the first electrode is formed by a sputtering method which is a dry process, the hole-injecting layer and the hole-transporting layer are individually formed by an inkjet method or a spin coating method which is a wet process, the light-emitting layer is formed by an inkjet method which is a wet process, the electron-injecting layer is formed by a vacuum evaporation method which is a dry process, and the second electrode is formed by a vacuum evaporation method which is a dry process. That is, over the substrate provided with the first electrode that has already been formed to have a desired shape, the layers from the hole-injecting layer to the light-emitting layer can be formed by a wet process, and the layers from the electron-transporting layer to the second electrode thereover can be formed by a dry process. This allows the layers from the hole-injecting layer to the light-emitting layer to be formed at atmospheric pressure and makes it easy to form the light-emitting layers separately for each color. Further, the layers from the electron-injecting layer to the second electrode can be formed in vacuum consistently. Therefore, a process can be simplified, and productivity can be improved.

The light-emitting element of the present invention, which has the above-described structure, emits light when a current flows due to the potential difference generated between the first electrode 101 and the second electrode 102 and then holes and electrons recombine in the light-emitting layer 113, which is the layer that contains the substance having a high light-emitting property. That is, the light-emitting element of the present invention has a structure in which the light-emitting region is formed in the light-emitting layer 113.

Having a bipolar property, that is, an electron-transporting property and a hole-transporting property, the triazole derivative described in Embodiment Mode 1 can be preferably used for the light-emitting layer. Further, since the triazole derivative has a bipolar property, the light-emitting region is not concentrated in an interface between the light-emitting layer and the hole-transporting layer or an interface between the light-emitting layer and the electron-transporting layer. Accordingly, concentration quenching of the light-emitting substance or quenching due to triplet-triplet annihilation (T-T annihilation) can be suppressed, whereby high emission efficiency can be achieved.

Further, since the triazole derivative described in Embodiment Mode 1 has a bipolar property, driving voltage of the light-emitting element can be reduced. Thus, power consumption of the light-emitting element can be reduced.

Furthermore, having high triplet excitation energy, the triazole derivative of the present invention can be used for the light-emitting layer, along with a phosphorescent compound. In particular, the triazole derivative of the present invention can be used for a full-color display or the like, because it can be used for the light-emitting layer, along with a phosphorescent compound that exhibits blue light emission at a wavelength greater than or equal to 400 nm and less than or equal to 500 nm. Accordingly, a full-color display utilizing the feature of the phosphorescent compound, which is high emission efficiency, can be achieved.

Note that this embodiment mode can be combined with any other embodiment mode as appropriate.

Embodiment Mode 3

In Embodiment Mode 3, a light-emitting element having a structure different from that of the light-emitting element described in Embodiment Mode 2 is described.

Having both an electron-transporting property and a hole-transporting property, the triazole derivative described in Embodiment Mode 1 can be used for the carrier-transporting layer. Specifically, the triazole derivative described in Embodiment Mode 1 can be used for the hole-transporting layer or the electron-transporting layer. In particular, since the triazole derivative described in Embodiment Mode 1 has high triplet excitation energy and high singlet excitation energy, energy transfer from the light-emitting layer does not easily occur in the case where the triazole derivative described in Embodiment Mode 1 is used for the layer in contact with the light-emitting layer. Accordingly, high emission efficiency can be achieved.

Note that this embodiment mode can be combined with any other embodiment mode as appropriate.

Embodiment Mode 4

In this embodiment mode, a mode of a light-emitting element according to the present invention, in which a plurality of light-emitting units are stacked (hereinafter referred to as a stacked-type element), is described with reference to FIG. 2. This light-emitting element is a stacked-type light-emitting element including a plurality of light-emitting units between a first electrode and a second electrode. For each light-emitting unit, a structure similar to the structure described in Embodiment Mode 2 or Embodiment Mode 3 can be used. That is, the light-emitting element described in Embodiment Mode 2 is a light-emitting element including one light-emitting unit. In this embodiment mode, the light-emitting element including the plurality of light-emitting units is described.

Figure 2:
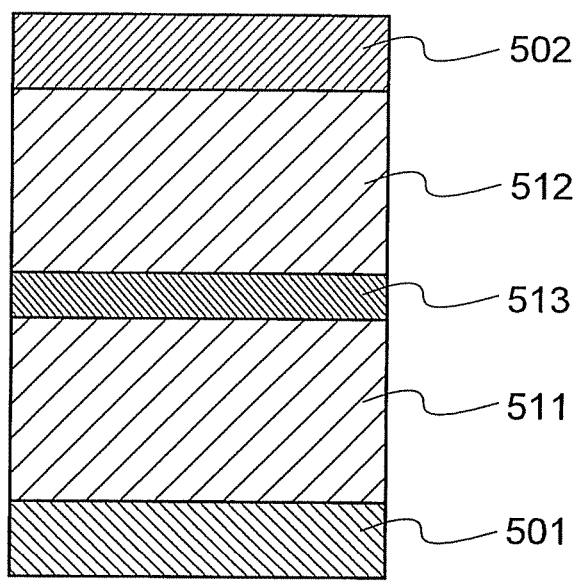
FIG. 2 illustrates a light-emitting element according to an aspect of the present invention.

In FIG. 2, a first light-emitting unit 511 and a second light-emitting unit 512 are stacked between a first electrode 501 and a second electrode 502. Electrodes similar to those described in Embodiment Mode 2 can be applied to the first electrode 501 and the second electrode 502. Alternatively, the structures of the first light-emitting unit 511 and the second light-emitting unit 512 may be the same or different from each other, and can be similar to the structure described in Embodiment Mode 2 or Embodiment Mode 3.

A charge generation layer 513 contains a composite material of an organic compound and metal oxide. This composite material of an organic compound and metal oxide is the composite material described in Embodiment Mode 2, and contains an organic compound and metal oxide such as vanadium oxide, molybdenum oxide, or tungsten oxide. As the organic compound, any of a variety of compounds such as aromatic amine compounds, carbazole derivatives, aromatic hydrocarbon, or high molecular compounds (e.g., oligomers, dendrimers, or polymers) can be used. Note that as the organic compound, an organic compound having a hole-transporting property, which has a hole mobility of $10^{-6}$ cm$^2$/Vs or more, is preferably used. However, any other substance may also be used as long as it is a substance in which the hole-transporting property is higher than the electron-transporting property. The composite material of the organic compound and the metal oxide has superior carrier-injecting property and superior carrier-transporting property, whereby low-voltage driving and low-current driving can be achieved.

Note that the charge generation layer 513 may be formed by combining the composite material of the organic compound and the metal oxide with another material. For example, the charge generation layer 513 may be formed by combining the layer containing the composite material of the organic compound and the metal oxide with a layer containing one compound selected from electron donating substances and a compound having a high electron-transporting property. Alternatively, the charge generation layer 513 may be formed by combining a transparent conductive film with a layer containing the composite material of the organic compound and the metal oxide.

In any case, the charge generation layer 513 interposed between the first light-emitting unit 511 and the second light-emitting unit 512 may have any structure as long as electrons can be injected into the light-emitting unit on one side and holes can be injected into the light-emitting unit on the other side when a voltage is applied between the first electrode 501 and the second electrode 502. For example, any structure is acceptable as long as the charge generation layer 513 injects electrons into the first light-emitting unit 511 and injects holes into the second light-emitting unit 512 when a voltage is applied so that the potential of the first electrode is higher than that of the second electrode.

Although the light-emitting element including two light-emitting units is described in this embodiment mode, in a similar manner to the light-emitting element including two light-emitting units, the present invention can be applied to a light-emitting element including three or more stacked light-emitting units. As in the light-emitting element according to this embodiment mode, by arranging a plurality of light-emitting units between a pair of electrodes so that the plurality of light-emitting units is partitioned by a charge generation layer, light emission in a high luminance region can be achieved with current density kept low; thus, a light-emitting element having long life can be realized. Further, when the light-emitting element is applied to a lighting apparatus, voltage drop due to resistance of the electrode materials can be suppressed; thus, uniform light emission in a large area can be achieved. Furthermore, a light-emitting device capable of low-voltage driving with less power consumption can be realized.

Having a bipolar property, that is, an electron-transporting property and a hole-transporting property, the triazole derivative described in Embodiment Mode 1 can be preferably used for the light-emitting layer. In addition, since the triazole derivative described in Embodiment Mode 1 has a bipolar property, the light-emitting region is not concentrated in the interface between the light-emitting layer and the hole-transporting layer or the interface between the light-emitting layer and the electron-transporting layer. Accordingly, concentration quenching of the light-emitting substance or quenching due to triplet-triplet annihilation (T-T annihilation) can be suppressed, whereby high emission efficiency can be achieved. Further, since the triazole derivative described in Embodiment Mode 1 has a bipolar property, driving voltage of the light-emitting element can be reduced. Thus, power consumption of the light-emitting element can be reduced.

Further, having both an electron-transporting property and a hole-transporting property, the triazole derivative described in Embodiment Mode 1 can be used for the carrier-transporting layer. Specifically, the triazole derivative described in Embodiment Mode 1 can be used as the hole-transporting layer or the electron-transporting layer. In particular, since the triazole derivative described in Embodiment Mode 1 has high triplet excitation energy and high singlet excitation energy, energy transfer from the light-emitting layer does not easily occur in the case where the triazole derivative described in Embodiment Mode 1 is used for the layer in contact with the light-emitting layer. Accordingly, high emission efficiency can be achieved.

Further, having a bipolar property, the triazole derivative described in Embodiment Mode 1 can be used as a carrier-transporting layer. Energy transfer from the light-emitting layer does not easily occur particularly when the triazole derivative described in Embodiment Mode 1 is used for the layer in contact with the light-emitting layer. Accordingly, high emission efficiency can be achieved.

Note that this embodiment mode can be combined with any other embodiment mode as appropriate.

Embodiment Mode 5

In this embodiment mode, a light-emitting device manufactured using the triazole derivative of the present invention is described.

In this embodiment mode, the light-emitting device manufactured using the triazole derivative of the present invention is described with reference to FIGS. 3A and 3B. Note that FIG. 3A is a top view of the light-emitting device, and FIG. 3B is a cross-sectional view taken along a line A-A' in FIG. 3A. This light-emitting device includes a driver circuit portion (a source-side driver circuit) 401, a pixel portion 402, and a driver circuit portion (a gate-side driver circuit) 403, which are shown with dotted lines, so as to control light emission from a light-emitting element. Further, reference numerals 404 and 405 denote a sealing substrate and a sealing material, respectively, and there is a space 407 surrounded by the sealing material 405.

Note that a lead wiring 408 is a wiring for transmitting signals input to the source-side driver circuit 401 and the gate-side driver circuit 403, and receives a video signal, a clock signal, a start signal, a reset signal, or the like from a flexible printed circuit (an FPC) 409 serving as an external input terminal. Note that although only the FPC is illustrated here, this FPC may be provided with a printed wiring board (a PWB). The category of the light-emitting device in this specification includes not only a light-emitting device itself but also a light-emitting device to which an FPC or a PWB is attached.

Next, a cross-sectional structure is described using FIG. 3B. The driver circuit portions and the pixel portion are formed over an element substrate 410. Here, the source-side driver circuit 401, which is the driver circuit portion, and one pixel in the pixel portion 402 are illustrated.

Note that as the source-side driver circuit 401, a CMOS circuit formed by combining an n-channel TFT 423 and a p-channel TFT 424 is formed. Further, the driver circuit may be formed of various types of circuits, such as CMOS circuits, PMOS circuits, or NMOS circuits. Furthermore, although a driver-integration type device, in which the driver circuit is formed over the same substrate as the pixel portion, is illustrated in this embodiment mode, the driver circuit is not necessarily formed over the same substrate as the pixel portion and can be formed outside the substrate.

Further, the pixel portion 402 is formed of a plurality of pixels, each of which includes a switching TFT 411, a current-controlling TFT 412, and a first electrode 413, which is electrically connected to a drain of the current-controlling TFT 412. Note that an insulator 414 is formed so as to cover an end portion of the first electrode 413. Here, a positive photosensitive acrylic resin film is used for the insulator 414.

Further, in order to obtain favorable coverage, the insulator 414 is formed so as to have a curved surface having curvature at an upper end portion or a lower end portion of the insulator 414. For example, in the case of using a positive photosensitive acrylic resin as a material for the insulator 414, the insulator 414 is preferably formed so as to have a curved surface with a curvature radius (0.2 μm to 3 μm) only at the upper end portion thereof. Further, for the insulator 414, either a negative photoresist that becomes insoluble in an etchant by light irradiation or a positive photoresist that becomes soluble in an etchant by light irradiation can be used.

Over the first electrode 413, a layer 416 containing an organic compound and a second electrode 417 are formed. Here, it is preferable to use a material having a high work function as a material for forming the first electrode 413 which functions as an anode. For example, any of the following materials can be used: a single-layer film such as an ITO film, an indium tin oxide film containing silicon, an indium oxide film containing zinc oxide of 2 wt % to 20 wt %, a titanium nitride film, a chromium film, a tungsten film, a Zn film, or a Pt film; a layered film of a titanium nitride film and a film containing aluminum as the main component; a three-layer structure film of a titanium nitride film, a film containing aluminum as the main component, and a titanium nitride film; or the like. Note that in the case of employing a layered film, resistance as a wiring is low, a good ohmic contact is formed, and further, the first electrode 413 can be made to function as an anode.

Further, the layer 416 containing an organic compound is formed by various methods such as an evaporation method using an evaporation mask, an inkjet method, or a spin coating method. The layer 416 containing an organic compound contains the triazole derivative described in Embodiment Mode 1. In addition, another material included in the layer 416 containing an organic compound may be any of low molecular compounds or high molecular compounds (the category includes oligomers and dendrimers).

Furthermore, as a material used for the second electrode 417 which is formed over the layer 416 containing an organic compound and functions as a cathode, it is preferable to use a material having a low work function (e.g., Al, Mg, Li, Ca, or an alloy or a compound thereof such as MgAg, MgIn, AlLi, LiF, or $CaF_2$). Note that when light generated in the layer 416 containing an organic compound is transmitted through the second electrode 417, the second electrode 417 is preferably formed of a layered film of a thin metal film with a reduced thickness and a transparent conductive film (e.g., ITO, indium oxide containing zinc oxide of 2 wt % to 20 wt %, indium oxide-tin oxide containing silicon or silicon oxide, or zinc oxide (ZnO)).

Furthermore, the sealing substrate 404 is attached to the element substrate 410 by using the sealing material 405. Accordingly, a light-emitting element 418 is provided in the space 407 surrounded by the element substrate 410, the sealing substrate 404, and the sealing material 405. Note that the space 407 is filled with a filler which may be an inert gas (e.g., nitrogen or argon) or may be the sealing material 405.

Note that an epoxy resin is preferably used for the sealing material 405. Further, such a material preferably allows as little moisture and oxygen as possible to penetrate. Furthermore, as a material used for the sealing substrate 404, a glass substrate, a quartz substrate, a plastic substrate made of fiberglass-reinforced plastics (FRP), polyvinyl fluoride (PVF), polyester, acrylic, or the like can be used.

As described above, the light-emitting device manufactured using the triazole derivative of the present invention can be obtained.

Since the triazole derivative described in Embodiment Mode 1 is used for the light-emitting device of the present invention, a light-emitting device having favorable characteristics can be obtained. In specific, the light-emitting device having high emission efficiency can be obtained.

Further, by using the triazole derivative of the present invention, a light-emitting device with less power consumption can be obtained Further, having high triplet excitation energy, the triazole derivative of the present invention can be used for the light-emitting layer, along with a phosphorescent compound. In particular, the triazole derivative of the present invention can be used for the light-emitting layer, along with a phosphorescent compound that exhibits blue light emission at a wavelength greater than or equal to 400 nM and less than or equal to 500 nm, and therefore can be used for a full-color display. Thus, a full-color display utilizing the feature of the phosphorescent compound, which is high emission efficiency, can be achieved.

Figure 4A:
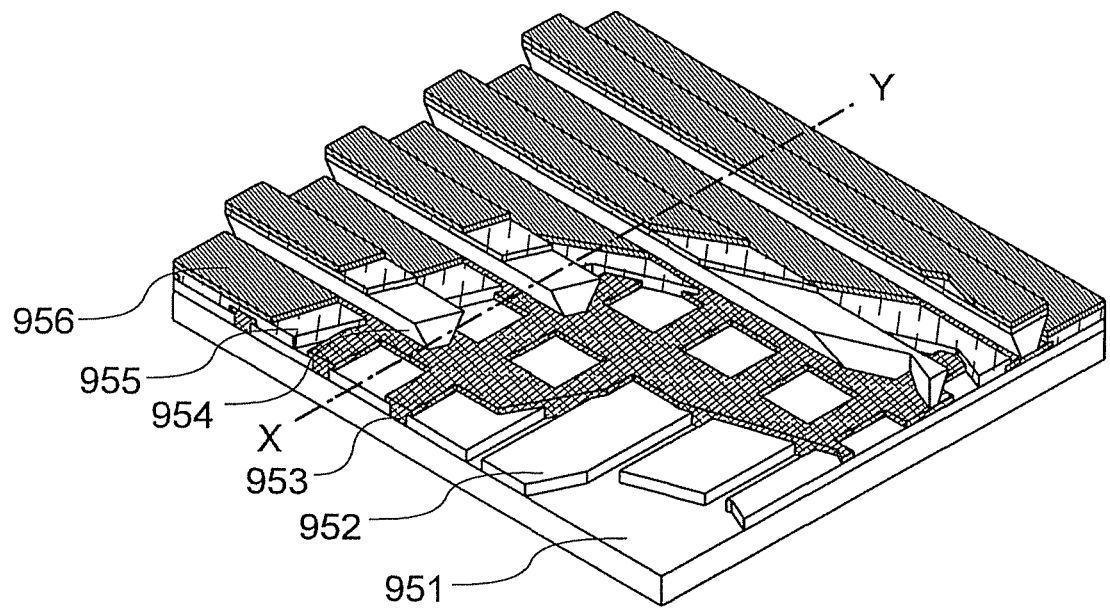
FIGS. 4A and 4B illustrate a light-emitting device according to an aspect of the present invention.
Figure 4B:
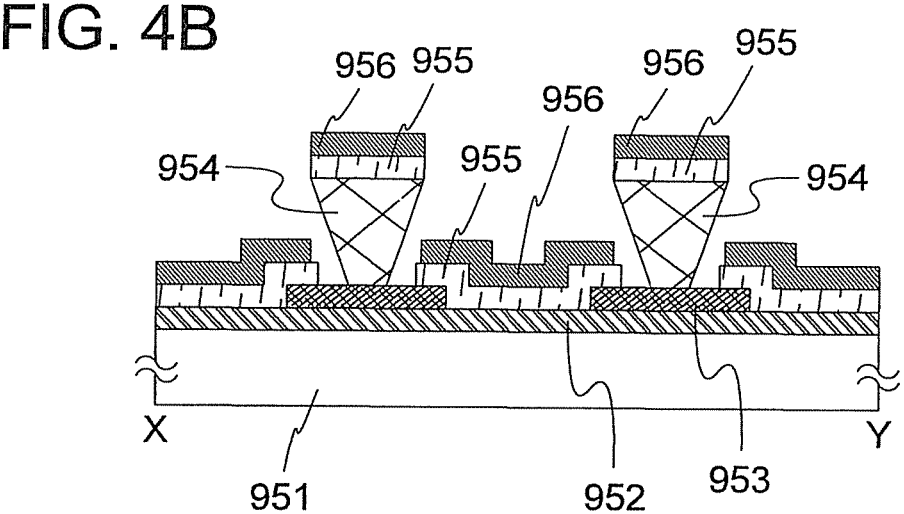

As described above, an active matrix light-emitting device in which driving of the light-emitting element is controlled by transistors is described in this embodiment mode. Alternatively, a passive matrix light-emitting device may be employed. FIGS. 4A and 4B illustrate a passive matrix light-emitting device manufactured by application of the present invention. Note that FIG. 4A is a perspective view of the light-emitting device, and FIG. 4B is a cross-sectional view taken along a line X-Y in FIG. 4A. In FIGS. 4A and 4B, an EL layer 955 is provided between an electrode 952 and an electrode 956 over a substrate 951. End portions of the electrode 952 are covered with an insulating layer 953. Then, a partition layer 954 is provided over the insulating layer 953. A side wall of the partition layer 954 slopes so that a distance between one side wall and the other side wall becomes narrow toward the substrate surface. In other words, a cross section taken along the direction of a shorter side of the partition layer 954 is trapezoidal, and the base of the cross-section (a side that faces in the same direction as a plane direction of the insulating layer 953 and is in contact with the insulating layer 953) is shorter than the upper side thereof (a side that faces in the same direction as the plane direction of the insulating layer 953 and is not in contact with the insulating layer 953). By providing the partition layer 954 in this manner, defects of the light-emitting element due to static electricity or the like can be prevented. Also in the passive matrix light-emitting device, a light-emitting element having high emission efficiency can be obtained by including the light-emitting element of the present invention. Further, a light-emitting device with less power consumption can be obtained.

Embodiment Mode 6

In this embodiment mode, electronic devices of the present invention, each of which includes the light-emitting device described in Embodiment Mode 5, are described. The electronic devices of the present invention each have a display portion which includes the triazole derivative described in Embodiment Mode 1 and have high emission efficiency. In addition, the power consumption of each display portion is reduced.

As examples of the electronic devices including the light-emitting element manufactured using the triazole derivative of the present invention, there are televisions, cameras such as video cameras and digital cameras, goggle type displays (head-mounted displays), navigation systems, audio replay devices (e.g., car audio systems and audio systems), computers, game machines, portable information terminals (e.g., mobile computers, cellular phones, portable game machines, and electronic book readers), image replay devices in which a recording medium is provided (devices that are capable of replaying recording media such as digital versatile discs (DVDs) and equipped with a display device that can display an image), and the like. Specific examples of these electronic devices are illustrated in FIGS. 5A to 5D.

Figure 5A:
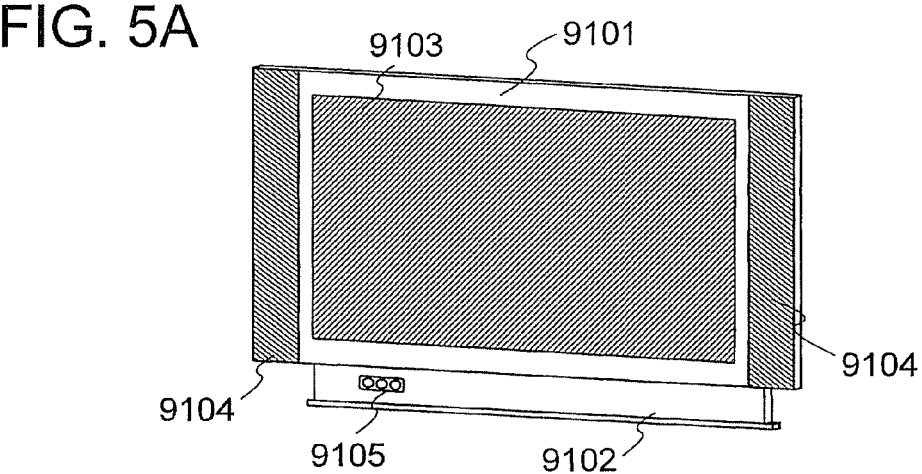
FIGS. 5A to 5D illustrate electronic devices according to an aspect of the present invention.

FIG. 5A illustrates a television set according to the present invention, which includes a chassis 9101, a supporting base 9102, a display portion 9103, a speaker portion 9104, a video input terminal 9105, and the like. In this television set, the display portion 9103 includes light-emitting elements similar to those described in Embodiment Mode 2 or Embodiment Mode 3, which are arranged in matrix. The light-emitting elements have a feature of high emission efficiency. Since the display portion 9103 includes the light-emitting elements having a similar feature, the power consumption of this television set is reduced. Due to such a feature, power supply circuits in the television set can be dramatically reduced or downsized, whereby the chassis 9101 and the supporting base 9102 can be reduced in size and weight. In the television set according to the present invention, low power consumption, high image quality, and reduced size and weight are achieved; therefore, a product suitable for living environments can be provided.

Figure 5B:
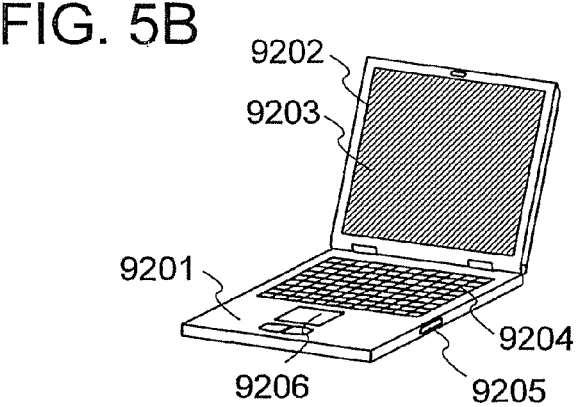

FIG. 5B illustrates a computer according to the present invention, which includes a main body 9201, a chassis 9202, a display portion 9203, a keyboard 9204, an external connection port 9205, a pointing device 9206, and the like. In this computer, the display portion 9203 includes light-emitting elements similar to those described in Embodiment Mode 2 or Embodiment Mode 3, which are arranged in matrix. The light-emitting elements have a feature of high emission efficiency. Since the display portion 9203 includes the light-emitting elements having a similar feature, the power consumption of this computer is reduced. Due to such a feature, power supply circuits in the computer can be dramatically reduced or downsized, whereby the main body 9201 and the chassis 9202 can be reduced in size and weight. In the computer according to the present invention, low power consumption, high image quality, and reduced size and weight are achieved; therefore, a product suitable for the environments can be provided.

Figure 5C:
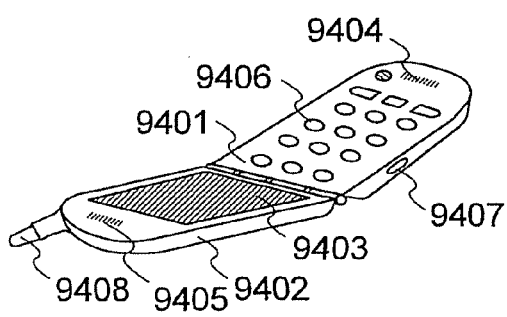

FIG. 5C illustrates a cellular phone according to the present invention, which includes a main body 9401, a chassis 9402, a display portion 9403, an audio input portion 9404, an audio output portion 9405, operation keys 9406, an external connection port 9407, an antenna 9408, and the like. In this cellular phone, the display portion 9403 includes light-emitting elements similar to those described in Embodiment Mode 2 or Embodiment Mode 3, which are arranged in matrix. The light-emitting elements have a feature of high emission efficiency. Since the display portion 9403 includes the light-emitting elements having a similar feature, the power consumption of this cellular phone is reduced. Due to such a feature, power supply circuits in the cellular phone can be dramatically reduced or downsized, whereby the main body 9401 and the chassis 9402 can be reduced in size and weight. In the cellular phone according to the present invention, low power consumption, high image quality, and a small size and light weight are achieved; therefore, a product suitable for carrying can be provided.

Figure 5D:
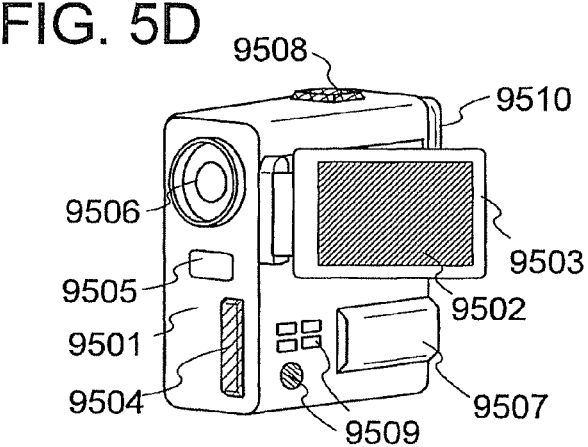

FIG. 5D illustrates a camera according to the present invention, which includes a main body 9501, a display portion 9502, a chassis 9503, an external connection port 9504, a remote control receiving portion 9505, an image receiving portion 9506, a battery 9507, an audio input portion 9508, operation keys 9509, an eye piece portion 9510, and the like. In this camera, the display portion 9502 includes light-emitting elements similar to those described in Embodiment Mode 2 or Embodiment Mode 3, which are arranged in matrix. The light-emitting elements have a feature of high emission efficiency. Since the display portion 9502 includes the light-emitting elements having a similar feature, the power consumption of this camera is reduced. Due to such a feature, power supply circuits in the camera can be dramatically reduced or downsized, whereby the main body 9501 can be reduced in size and weight. In the camera according to the present invention, low power consumption, high image quality, and reduced size and weight are achieved; therefore, a product suitable for carrying can be provided.

As described above, the applicable range of the light-emitting device of the present invention is wide so that the light-emitting device can be applied to electronic devices of a variety of fields. By using the triazole derivative of the present invention, an electronic device having a display portion with high emission efficiency can be provided. Furthermore, the electronic device of the present invention having the display portion with less power consumption can be obtained.

The light-emitting device of the present invention can also be used as a lighting apparatus. One mode in which the light-emitting device of the present invention is used as a lighting apparatus is described using FIG. 6.

Figure 6:
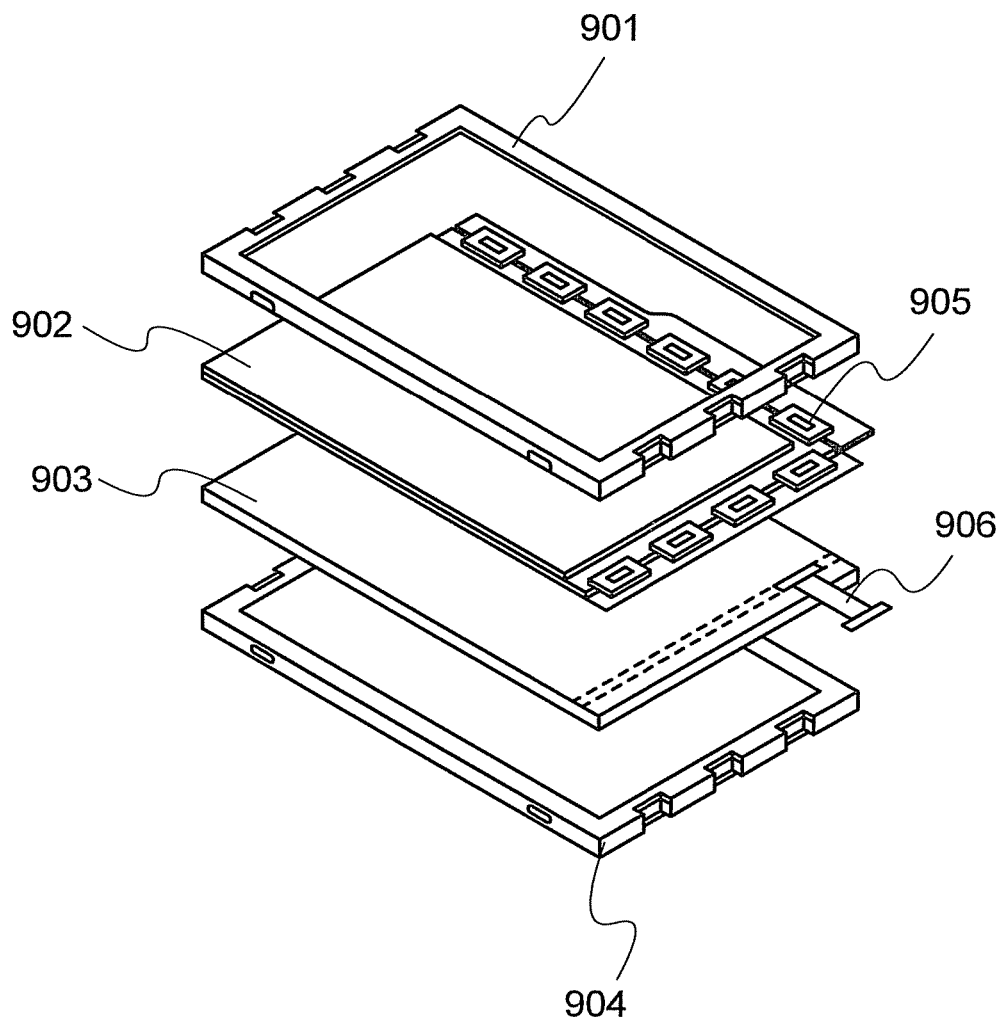
FIG. 6 illustrates an electronic device according to an aspect of the present invention.

FIG. 6 illustrates an example of a liquid crystal display device in which the light-emitting device of the present invention is used as a backlight. The liquid crystal display device illustrated in FIG. 6 includes a chassis 901, a liquid crystal layer 902, a backlight 903, and a chassis 904. The liquid crystal layer 902 is connected to a driver IC 905. Further, as the backlight 903, the light-emitting device of the present invention is used and a current is supplied through a terminal 906.

When the light-emitting device of the present invention is used as the backlight of the liquid crystal display device, a backlight having high emission efficiency and reduced power consumption can be obtained. Further, the light-emitting device of the present invention is a plane emission lighting apparatus and can also have a large area; accordingly, it is possible that the backlight have a larger area and the liquid crystal display device have a larger display area. Furthermore, the light-emitting device of the present invention has a thin shape and low power consumption; thus, a display device can also be reduced in thickness and power consumption.

Figure 7:
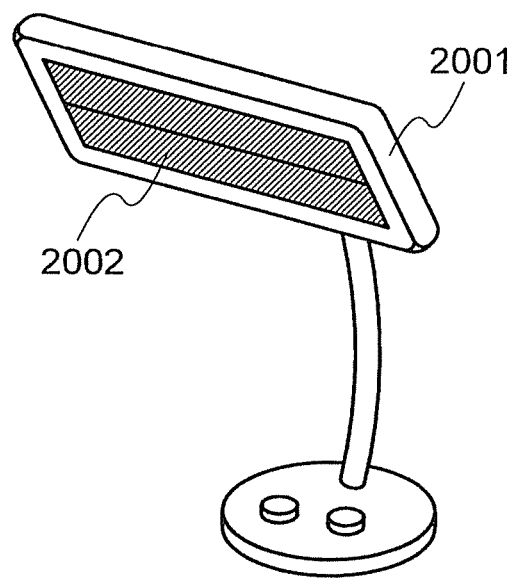
FIG. 7 illustrates a lighting apparatus according to an aspect of the present invention.

FIG. 7 illustrates an example in which the light-emitting device to which the present invention is applied is used as a desk lamp which is a lighting apparatus. A desk lamp illustrated in FIG. 7 has a chassis 2001 and a light source 2002, and the light-emitting device of the present invention is used as the light source 2002. Since the light-emitting device of the present invention has high emission efficiency and low power consumption, the desk lamp also has high emission efficiency and low power consumption.

Figure 8:
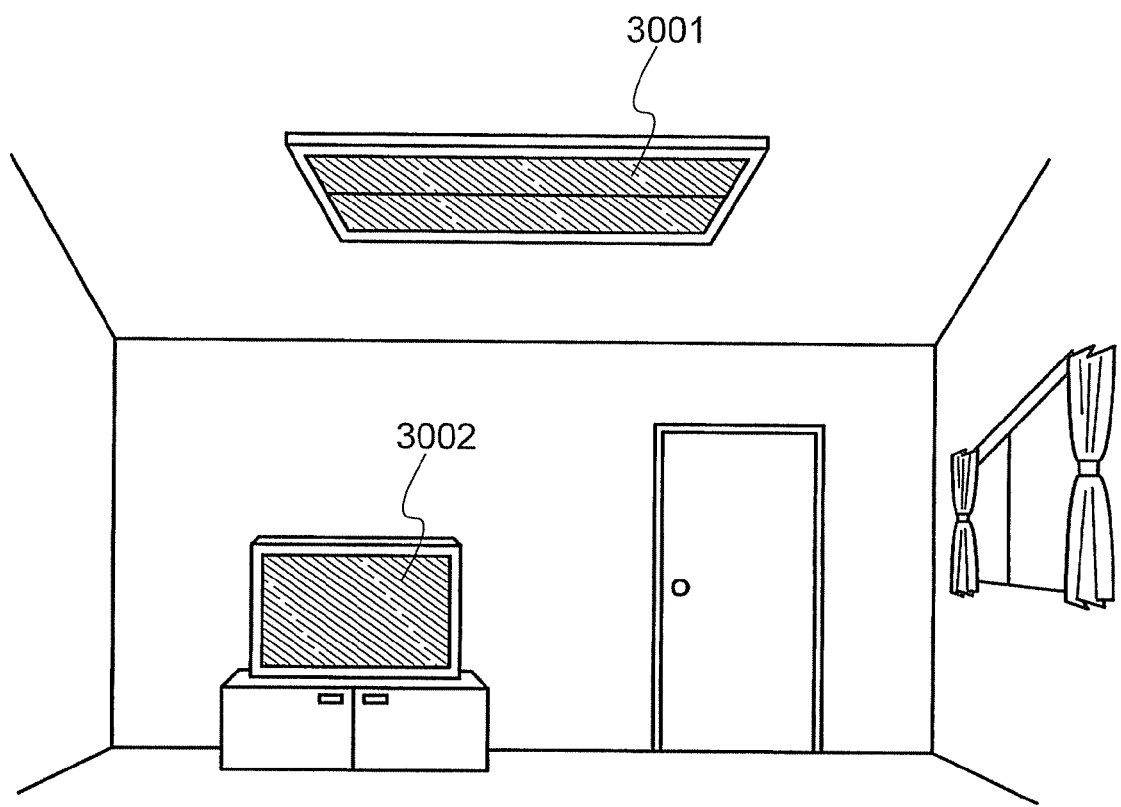
FIG. 8 illustrates a lighting apparatus according to an aspect of the present invention.

FIG. 8 illustrates an example in which the light-emitting device to which the present invention is applied is used as an indoor lighting apparatus 3001. Since the area of the light-emitting device of the present invention can be large, the light-emitting device of the present invention can be used as a lighting apparatus having a large area. Further, having a thin shape and low power consumption, the light-emitting device of the present invention can be used as a lighting apparatus having a thinner shape and less power consumption. In a room where the light-emitting device to which the present invention is thus applied is used as the indoor lighting apparatus 3001, a television set 3002 according to the present invention, as described in FIG. 5A, is placed; then, public broadcasting and movies can be watched. In such a case, since both of the devices consume low power, a powerful image can be enjoyed in a bright room without concern about electricity charges.

Example 1

Synthesis Example 1

In this example, a synthesis method of 4-(9H-carbazol-9-yl)-4'-(4,5-diphenyl-4H-1,2,4-triazol-3-yl)triphenylamine (abbreviation: YGATAZ1) represented by a structural formula (200) is described.

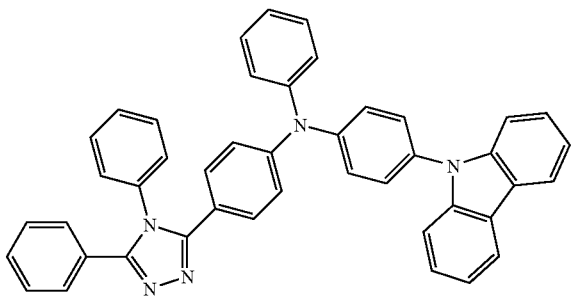

(200)

Step 1: Synthesis of
3-(4-Bromophenyl)-4,5-diphenyl-4H-1,2,4-triazole (1) Synthesis of 4-Bromobenzoylhydrazine Into a 200 mL three-neck flask was put 25 g (0.19 mol) of ethyl-4-bromobenzoate, 50 mL of ethanol was added thereto, and the mixture was stirred. After that, 20 mL of hydrazine monohydrate was added to the mixture, and then the mixture was stirred while being heated at 78° C. for 5 hours to be reacted. After the reaction, water was added to the reaction mixture, and a precipitated solid was collected by suction filtration. The obtained solid was washed with water and collected by suction filtration, whereby 24 g of a white solid of 4-bromobenzoylhydrazine, which was the object of the synthesis, was obtained in a yield of 96% (synthesis scheme (a-1)).

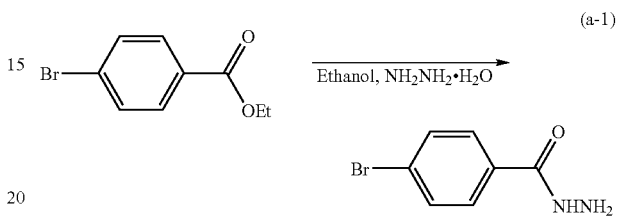

(a-1)

(2) Synthesis of
N'-benzoyl-4-bromo-benzohydrazide

Into a 300 mL three-neck flask was put 2.0 g (13.9 mmol) of 4-bromobenzoylhydrazine obtained by the above Step 1 (1), 7 mL of N-methyl-2-pyrrolidone was added thereto, and the mixture was stirred at room temperature. A mixed solution of 5.0 mL of N-methyl-2-pyrrolidone and 2.5 mL (21.5 mmol) of benzoyl chloride was dripped into this solution through a 50 mL dropping funnel. This mixture was stirred at 80° C. for 3 hours. After the reaction, the reaction mixture was added to about 200 mL of water, whereby a solid was precipitated. The precipitated solid was collected by suction filtration. The collected solid was washed with water, a saturated aqueous sodium hydrogen carbonate solution, and a saturated saline solution in that order to give a solid. The obtained solid was recrystallized with a mixed solvent of acetone and hexane, whereby 3.6 g of a white solid of N'-benzoyl-4-bromo-benzohydrazide, which was the object of the synthesis, was obtained in a yield of 80% (synthesis scheme (a-2)).

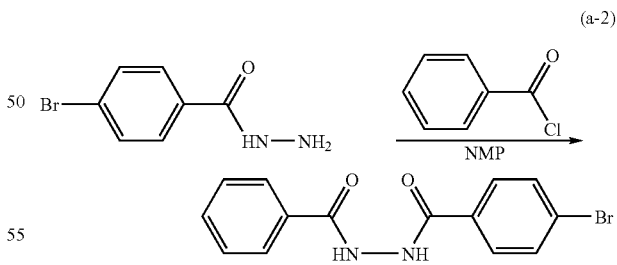

(a-2)

(3) Synthesis of 1-[(4-Bromophenyl)chloromethylidene]-2-[chloro(phenyl)methylidene]hydrazone Into a 200 mL three-neck flask were put 5.0 g (16 mmol) of N'-benzoyl-4-bromo-benzohydrazide obtained by the above Step 1 (2) and 7.2 g (34 mmol) of phosphorus pentachloride. To this mixture was added 100 mL of toluene. This mixture was stirred at 120° C. for 3 hours to be reacted. After the reaction, the reaction solution was added to about 100 mL of water, and the mixture was stirred. An organic layer was separated from an aqueous layer, and washed with a saturated aqueous sodium carbonate solution and a saturated saline solution. Magnesium sulfate was added to the organic layer, so that the organic layer was dried. This mixture was suction filtered, so that the magnesium sulfate was removed, whereby a filtrate was obtained. The obtained filtrate was concentrated to give a solid. The solid was washed with methanol, whereby 4.8 g of a powdery light-yellow solid of 1-[(4-bromophenyl)chloromethylidene]-2-[chloro(phenyl)methylidene]hydrazone, which was the object of the synthesis, was obtained in a yield of 86% (synthesis scheme (a-3)).

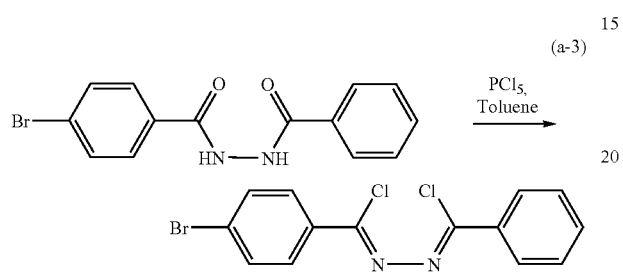

(a-3)

(4) Synthesis of 3-(4-Bromophenyl)-4,5-diphenyl-4H-1,2,4-triazole

Into a 100 mL three-neck flask were put 4.5 g (16 mmol) of 1-[(4-bromophenyl)chloromethylidene]-2-[chloro(phenyl)methylidene]hydrazone obtained by the above Step 1 (3), 2.0 g (16 mmol) of aniline, and 30 mL of N,N-dimethylaniline. Then, the atmosphere in the flask was replaced with nitrogen. This mixture was stirred while being heated at 135° C. for 5 hours. After the reaction, the reaction solution was added to about 100 mL of 1 M diluted hydrochloric acid, and the mixture was stirred for 30 minutes, whereby a solid was precipitated. The precipitated solid was suction filtered, whereby a solid was obtained. The obtained solid was dissolved in toluene, and the mixture was washed with water and a saturated aqueous sodium carbonate solution. Magnesium sulfate was added to an organic layer, so that the organic layer was dried. This mixture was suction filtered, so that the magnesium sulfate was removed, whereby a filtrate was obtained. The obtained filtrate was concentrated to give a solid. The obtained solid was recrystallized with a mixed solvent of ethanol and hexane, whereby 3.3 g of a powdery light-yellow solid of 3-(4-bromophenyl)-4,5-diphenyl-4H-1,2,4-triazole, which was the object of the synthesis, was obtained in a yield of 69% (synthesis scheme (a-4)).

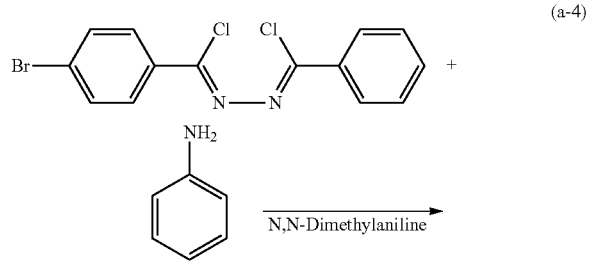

(a-4)

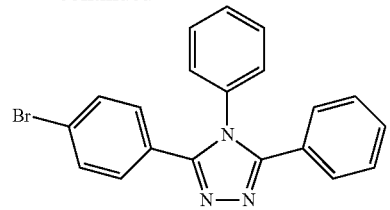

Step 2: Synthesis of 4-(9H-carbazol-9-yl)diphenylamine (abbreviation: YGA)

(1) Synthesis of 9-(4-Bromophenyl)-9H-carbazole

Into a 300 mL three-neck flask were put 56 g (240 mmol) of p-dibromobenzene, 31 g (180 mmol) of 9H-carbazole, 4.6 g (24 mmol) of copper(I) iodide, 66 g (480 mmol) of potassium carbonate, and 2.1 g (8 mmol) of 18-crown-6-ether. Then, the atmosphere in the flask was replaced with nitrogen. Then, 8 mL of N,N'-dimethylpropyleneurea (abbreviation: DMPU) was added to the mixture, and the mixture was stirred at 180° C. for 6 hours. After the reaction mixture was cooled to room temperature, a precipitate was removed by suction filtration. The filtrate was washed with dilute hydrochloric acid, a saturated aqueous sodium hydrogen carbonate solution, and a saturated saline solution in that order, and dried with magnesium sulfate. After being dried, the mixture was gravity filtered and then concentrated to give an oily substance. The obtained oily substance was purified by silica gel column chromatography (hexane:ethyl acetate=9:1) and recrystallized with chloroform and hexane, whereby 21 g of light-brown plate-shaped crystals of 9-(4-bromophenyl)-9H-carbazole which was the object of the synthesis was obtained in a yield of 35% (synthesis scheme (a-5)).

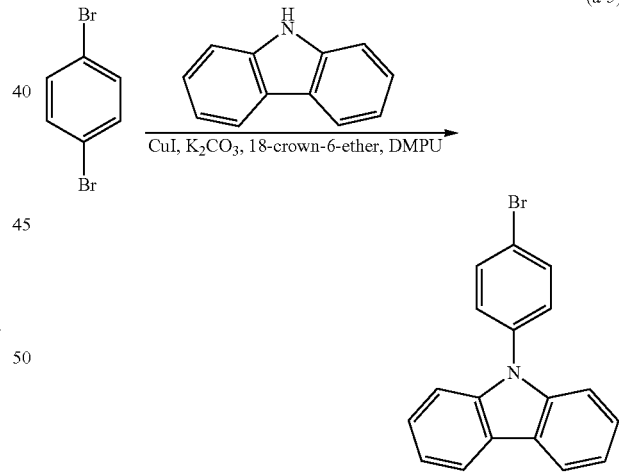

(a-5)

(2) Synthesis of 4-(9H-carbazol-9-yl)diphenylamine (abbreviation: YGA)

Into a 200 mL three-neck flask were put 5.4 g (17 mmol) of 9-(4-bromophenyl)carbazole-9H-carbazole obtained by the above Step 2 (1), 1.8 mL (20 mmol) of aniline, 0.1 g (0.2 mmol) of bis(dibenzylideneacetone)palladium(0), and 3.9 g (40 mmol) of sodium-tert-butoxide. The atmosphere in the flask was replaced with nitrogen. Then, 0.1 mL of a 10% hexane solution of tri(tert-butyl)phosphine and 50 mL of toluene were added to the mixture, and the mixture was stirred at 80° C. for 6 hours. The reaction mixture was filtered through Florisil (produced by Wako Pure Chemical Industries, Ltd., Catalog No. 540-00135), Celite (produced by Wako Pure Chemical Industries, Ltd., Catalog No. 531-16855), and alumina. The filtrate was washed with water and a saturated saline solution, and then dried with magnesium. After being dried, the mixture was gravity filtered, and the obtained filtrate was concentrated to give an oily substance. The obtained oily substance was purified by silica gel column chromatography (hexane:ethyl acetate=9:1), whereby 4.1 g of 4-(9H-carbazol-9-yl)diphenylamine (abbreviation: YGA), which was the object of Step 2, in a yield of 73% (synthesis scheme (a-6)).

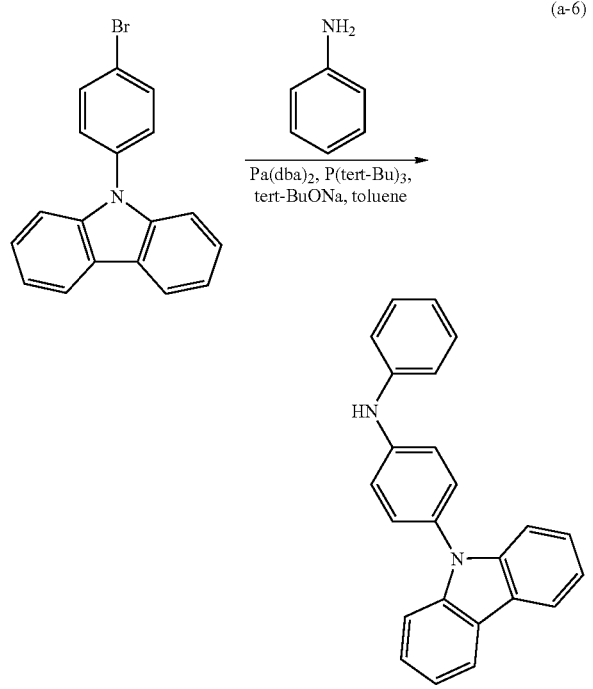

(a-6)

Step 3: Synthesis of 4-(9H-carbazol-9-yl)-4'-(4,5-diphenyl-4H-1,2,4-triazol-3-yl)triphenylamine (abbreviation: YGATAZ1)

Into a 100 mL three-neck flask were put 1.5 g (4.0 mmol) of 3-(4-bromophenyl)-4,5-diphenyl-4H-1,2,4-triazole obtained by the above Steps 1 (1) to 1 (4), 1.3 g (4.0 mmol) of 4-(9H-carbazol-9-yl)diphenylamine (abbreviation: YGA) obtained by the above Steps 2 (1) and 2 (2), 1.0 g (11 mmol) of sodium-tert-butoxide, and 0.1 g (0.2 mmol) of bis(dibenzylideneacetone)palladium(0). The atmosphere in the flask was replaced with nitrogen. To this mixture were added 30 mL of toluene and 0.1 mL of a 10% hexane solution of tri(tert-butyl)phosphine. This mixture was stirred while being heated at 80° C. for 5 hours to be reacted. After the reaction, toluene was added to the reaction mixture, and the mixture was heated. This suspension was suction filtered through Celite (produced by Wako Pure Chemical Industries, Ltd., Catalog No. 531-16855). The filtrate was washed with water, a saturated aqueous sodium hydrogen carbonate solution, and a saturated saline solution in that order. Then, an organic layer was separated from an aqueous layer. To the organic layer was added magnesium sulfate, so that the organic layer was dried. This mixture was suction filtered, so that the magnesium sulfate was removed, whereby a filtrate was obtained. The filtrate was concentrated to give a solid. The obtained solid was dissolved in toluene, and the solution was purified by silica gel column chromatography. In the column chromatography, as developing solvents, toluene was used first and a mixed solvent (toluene:ethyl acetate=1:4) was used next. An obtained fraction was concentrated to give a solid. The obtained solid was recrystallized with a mixed solvent of chloroform and hexane, whereby 1.8 g of a white solid of 4-(9H-carbazol-9-yl)-4'-(4,5-diphenyl-4H-1,2,4-triazol-3-yl)triphenylamine (abbreviation: YGATAZ1), which was the object of the synthesis, was obtained in a yield of 72% (synthesis scheme (a-7)).

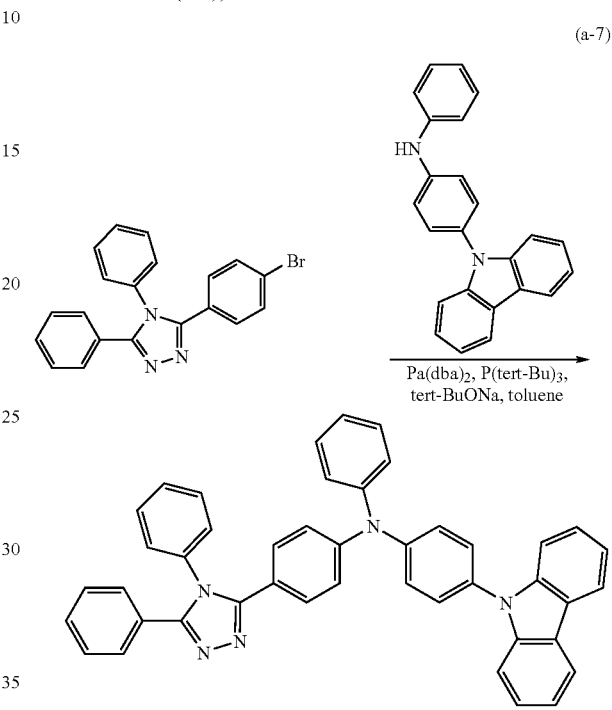

(a-7)

Sublimation purification of 1.8 g of the obtained white solid was performed by a train sublimation method. In the sublimation purification, with a reduced pressure of 7.0 Pa and an argon flow rate of 3 mL/min, the white powder was heated at 310° C. for 15 hours, whereby 1.2 g of a resulting substance was obtained in a yield of 67%.

Figure 9A:
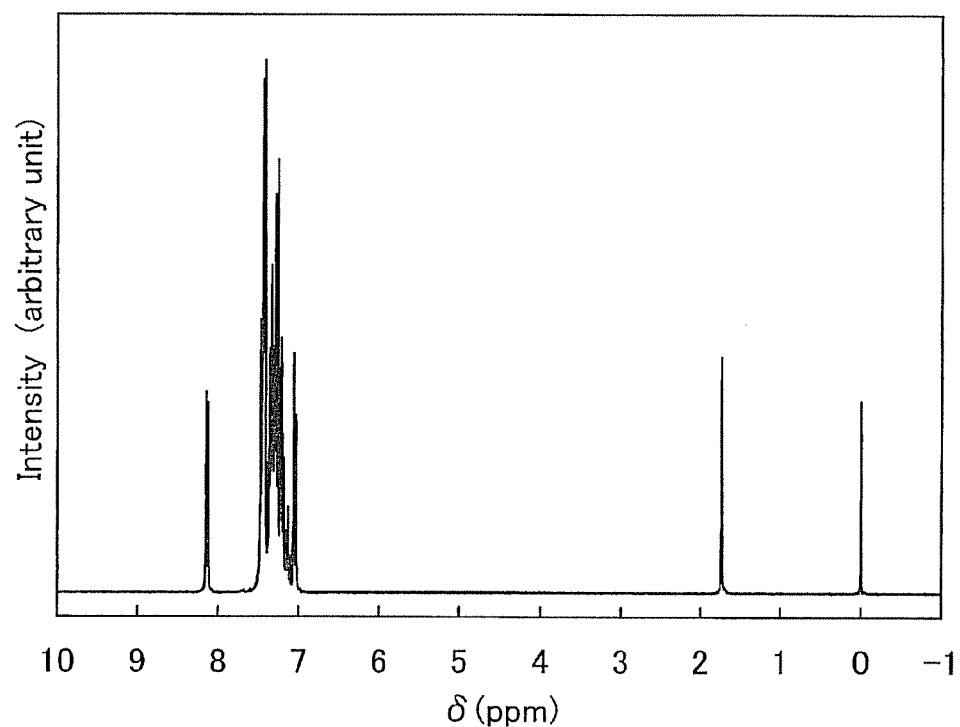
FIGS. 9A and 9B show $^1$H NMR charts of YGATAZ1.
Figure 9B:
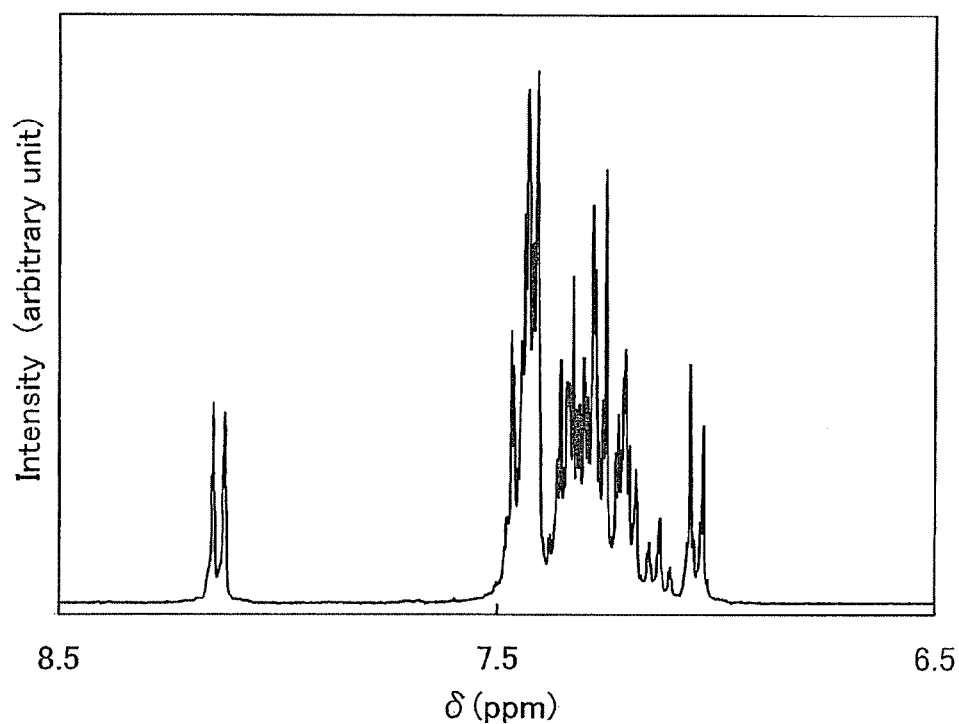

Note that the solid obtained by the above Step 2 was measured by $^1$H NMR. The measurement data are given below. In addition, FIGS. 9A and 9B show $^1$H NMR charts. Note that FIG. 9B is a chart showing an enlarged view of the range of 6.5 ppm to 8.5 ppm in FIG. 9A.

$^1$H NMR (CDCl$_3$, 300 MHz): δ=7.05 (d, J=8.8 Hz, 2H), 7.09-7.51 (m, 27H), 8.14 (d, J=7.8 Hz, 2H).

Figure 10A:
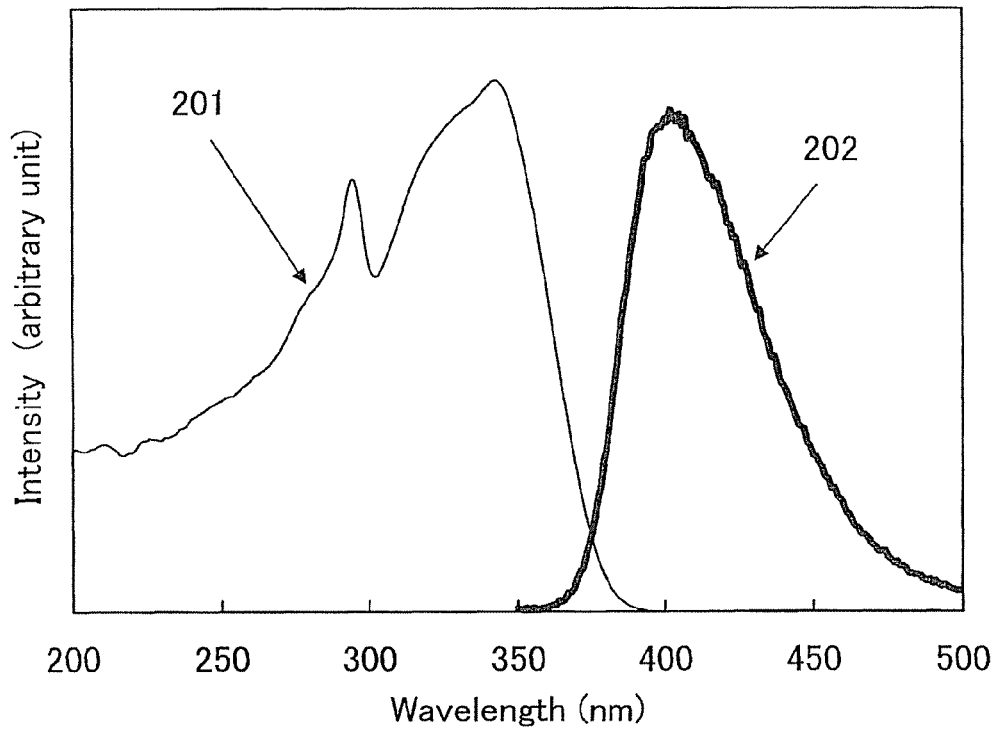
FIGS. 10A and 10B show the absorption spectrum and emission spectrum of YGATAZ1.
Figure 10B:
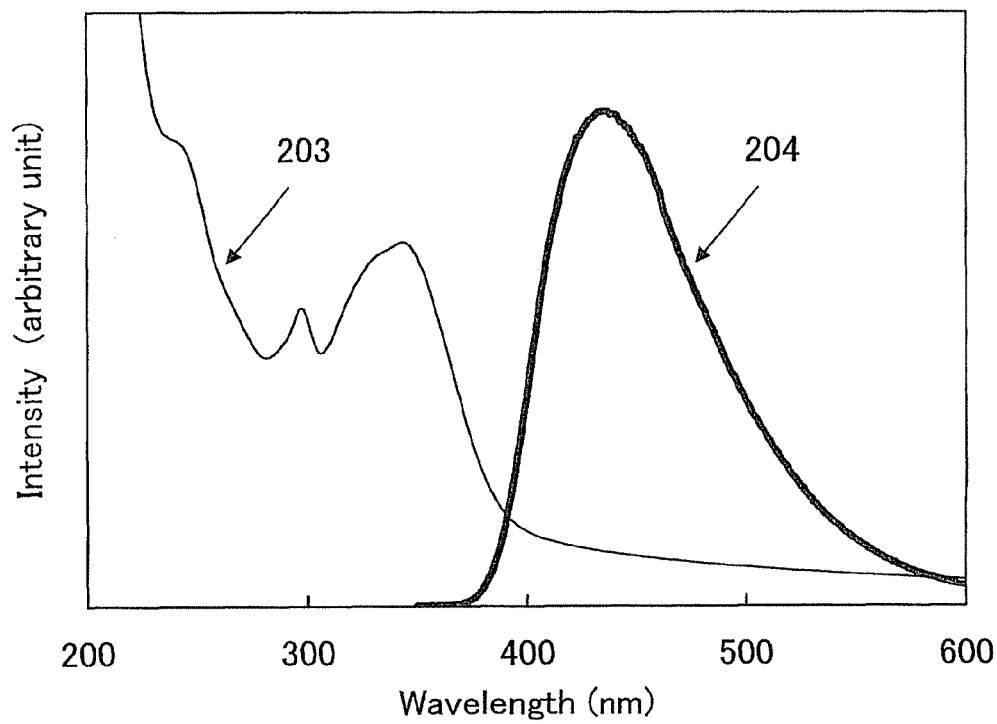

Further, FIG. 10A shows the absorption spectrum 201 and emission spectrum 202 of a toluene solution of YGATAZ1. Furthermore, FIG. 10B shows the absorption spectrum 203 and emission spectrum 204 of the thin film of YGATAZ1. For the measurements, an ultraviolet-visible light spectrophotometer (V-550, manufactured by JASCO Corporation) was used. The solution was put into a quartz cell to form one sample, and YGATAZ1 was evaporated over a quartz substrate to form the thin film as another sample. FIGS. 10A and 10B show the absorption spectra of the solution and the thin film, from each of which the absorption spectrum of quartz was subtracted. In FIGS. 10A and 10B, the horizontal axis represents wavelength (nm), and the vertical axis represents intensity (arbitrary unit). In the case of the toluene solution of YGATAZ1, the absorption was observed at around 343 nm and the maximum emission wavelength was 402 nm (excitation wavelength: 343 nm). Further, in the case of the thin film of YGATAZ1, the absorption was observed at around 343 nm and the maximum emission wavelength was 435 nm (excitation wavelength: 332 nm).

Moreover, as a result of measurements with a photoelectron spectrometer (AC-2 photoelectron spectrometer manufactured by Riken Keiki, Co., Ltd.) in the atmosphere, the ionized potential of the thin film of YGATAZ1 was 5.46 eV. Accordingly, it was understood that the HOMO level was −5.46 eV. Furthermore, with the use of the absorption spectrum data of the thin film of YGATAZ1, the absorption edge was obtained by a Tauc plot assuming direct transition. The absorption edge was estimated as an optical energy gap, whereby the energy gap was 3.27 eV. From the obtained values of the energy gap and HOMO level, the LUMO level was −2.19 eV.

Thus, it was understood that YGATAZ1 is a substance having high singlet excitation energy (band gap).

Further, the optimal molecular structure of the ground state of YGATAZ1 was estimated by B3LYP/6-311 (d, p) of density functional theory (DFT). DFT was applied to the present calculation because the accuracy of calculation is higher than that of the Hartree-Fock (HF) method, which does not consider electron correlation, and calculation costs are lower than those of a Moller Plesset (MP) perturbation method, which has the same level of accuracy of calculation as that of DFT. The calculations were performed with a high performance computer (HPC) (Altix 3700 DX manufactured by SGI). By applying B3LYP/6-311 (d, p) of time-dependent density functional theory (TDDFT) to the molecular structure which was structurally optimized by DFT, the triplet excitation energy of YGATAZ1 was calculated to be 2.76 eV, which corresponds to 449.6 nm when being converted into wavelength. From the above results, it was understood that the triazole derivative of the present invention is a substance having high excitation energy. In particular, it was understood that the triazole derivative of the present invention is a substance having high triplet excitation energy.

Synthesis Example 2

In this example, a synthesis method of 4-(9H-carbazol-9-yl)-4'-(3,5-diphenyl-4H-1,2,4-triazol-4-yl)triphenylamine (abbreviation: YGATAZ2) represented by a structural formula (201) is described.

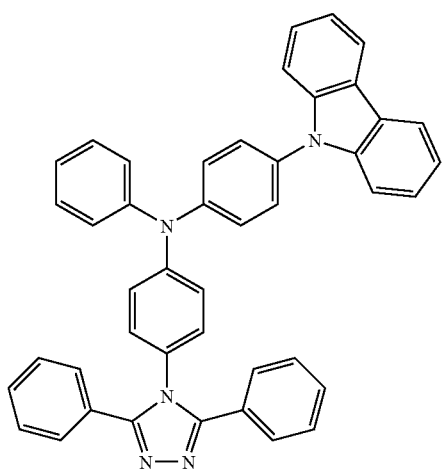

(201)

Step 1: Synthesis of 4-(4-Bromophenyl)-3,5-diphenyl-4H-1,2,4-triazole (1) Synthesis of Benzohydrazide Into a 200 mL three-neck flask was put 25 g (0.17 mol) of ethyl benzoate, 60 mL of ethanol was added thereto, and the mixture was stirred. After that, 20 mL of hydrazine monohydrate was added to the mixture, and this mixture was stirred while being heated at 78° C. for 8 hours. After the reaction, the reaction solution was added to about 500 mL of water, and ethyl acetate was added to this aqueous solution. An organic layer was separated from an aqueous layer, and washed with a saturated aqueous sodium hydrogen carbonate solution and a saturated saline solution in that order. Magnesium sulfate was added to the organic layer, so that the organic layer was dried. This mixture was suction filtered, so that the magnesium sulfate was removed, whereby a filtrate was obtained. The obtained filtrate was concentrated to give a solid. The solid was recrystallized with a mixed solvent of ethanol and hexane, whereby 15 g of a white solid of benzohydrazide, which was the object of the synthesis, was obtained in a yield of 66% (synthesis scheme (b-1)).

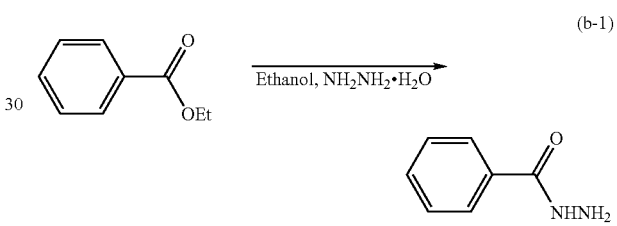

(b-1)

(2) Synthesis of 1,2-Dibenzoylhydrazine

Into a 300 mL three-neck flask was put 10 g (73 mmol) of benzohydrazide obtained by the above Step 1 (1) in Synthesis Example 2, 25 mL of N-methyl-2-pyrrolidone was added thereto, and the mixture was stirred. Then, a mixed solution of 10 mL of N-methyl-2-pyrrolidone and 10 mL (88 mmol) of benzoyl chloride was dripped into the mixture through a 50 mL dropping funnel. This mixture was stirred at 80° C. for 3 hours to be reacted. After the reaction, the reaction solution was added to about 500 mL of water, and the mixture was stirred, whereby a solid was precipitated. The precipitated solid was collected by suction filtration. The collected solid was washed with water, and methanol was added to the obtained solid such that the solid was washed, whereby 10 g of a powdery white solid of 1,2-dibenzoylhydrazine, which was the object of the synthesis, was obtained in a yield of 57% (synthesis scheme (b-2)).

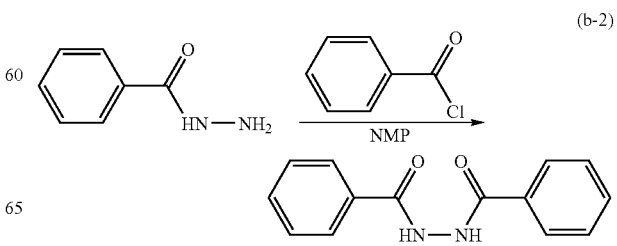

(b-2)

(3) Synthesis of 1,2-Bis[chloro(phenyl)methylidene]hydrazone

Into a 200 mL three-neck flask were put 5.0 g (21 mmol) of 1,2-dibenzoylhydrazine obtained by the above Step 1 (2) in Synthesis Example 2 and 9.5 g (46 mmol) of phosphorus pentachloride, and 80 mL of toluene was added to this mixture. This mixture was stirred at 120° C. for 3 hours to be reacted. After the reaction, the reaction solution was added to about 100 mL of water, and the mixture was stirred. An organic layer was separated from an aqueous layer, and washed with water and a saturated aqueous sodium hydrogen carbonate solution. Magnesium sulfate was added to the organic layer, so that the organic layer was dried. This mixture was suction filtered, so that the magnesium sulfate was removed, whereby a filtrate was obtained. The obtained filtrate was concentrated to give a solid. The solid was washed with methanol, whereby 4.9 g of a powdery light-yellow solid of 1,2-bis[chloro(phenyl)methylidene]hydrazone, which was the object of the synthesis, was obtained in a yield of 85% (synthesis scheme (b-3)).

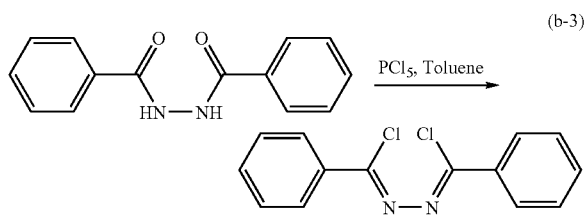

(b-3)

(4) Synthesis of 4-(4-Bromophenyl)-3,5-diphenyl-4H-1,2,4-triazole

Into a 100 mL three-neck flask were put 4.5 g (16 mmol) of 1,2-bis[chloro(phenyl)methylidene]hydrazone obtained by the above Step 1 (3) in Synthesis Example 2, 2.0 g (16 mmol) of 4-bromoaniline, and 30 mL of N,N-dimethylaniline. The atmosphere in the flask was replaced with nitrogen. This mixture was stirred while being heated at 135° C. for 5 hours. After the reaction, the reaction solution was added to about 100 mL of 1 M dilute hydrochloric acid, and the mixture was stirred for 30 minutes, whereby a solid was precipitated. The precipitated solid was suction filtered, whereby a solid was obtained. The obtained solid was dissolved in toluene, and the mixture was washed with water and a saturated aqueous sodium carbonate solution. Magnesium sulfate was added to an organic layer, so that the organic layer was dried. This mixture was suction filtered, so that the magnesium sulfate was removed, whereby a filtrate was obtained. The obtained filtrate was concentrated to give a solid. The solid was recrystallized with a mixed solvent of ethanol and hexane, whereby 2.3 g of a powdery white solid of 4-(4-bromophenyl)-3,5-diphenyl-4H-1,2,4-triazole, which was the object of the synthesis, was obtained in a yield of 38% (synthesis scheme (b-4)).

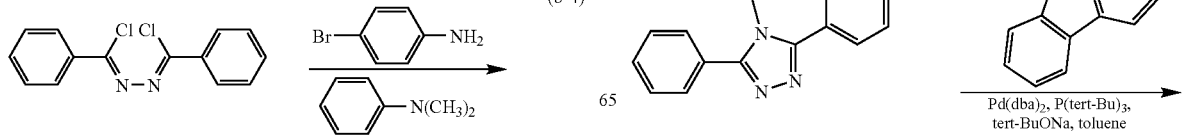

(b-4)

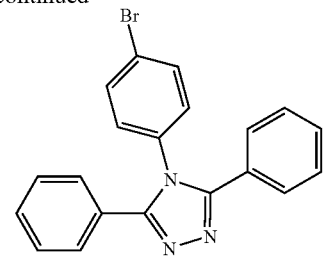

Step 2: Synthesis of 4-(9H-carbazol-9-yl)-4'-(3,5-diphenyl-4H-1,2,4-triazol-4-yl)triphenylamine (abbreviation: YGATAZ2)

Into a 100 mL three-neck flask were put 0.80 g (2.1 mmol) of 4-(4-bromophenyl)-3,5-diphenyl-4H-1,2,4-triazole obtained by the above Steps 1 (1) to 1 (4) in Synthesis Example 2, 0.71 g (2.1 mmol) of 4-(9H-carbazol-9-yl)diphenylamine (abbreviation: YGA) obtained by the above Steps 2 (1) and 2 (2) in Synthesis Example 1, 0.5 g (5.5 mmol) of sodium-tert-butoxide, and 0.050 g (0.10 mmol) of bis(dibenzylideneacetone)palladium(0). The atmosphere in the flask was replaced with nitrogen. To this mixture were added 15 mL of toluene and 0.05 mL of a 10% hexane solution of tri(tert-butyl)phosphine. This mixture was stirred while being heated at 80° C. for 5 hours to be reacted. After the reaction, toluene was added to the reaction mixture, and the mixture was heated. This suspension was suction filtered through Celite (produced by Wako Pure Chemical Industries, Ltd., Catalog No. 531-16855). An obtained filtrate was washed with water, a saturated aqueous sodium hydrogen carbonate solution, and a saturated saline solution in that order. Then, an organic layer was separated from an aqueous layer. To the organic layer was added magnesium sulfate, so that the organic layer was dried. This mixture was suction filtered, so that the magnesium sulfate was removed, whereby a filtrate was obtained. The filtrate was concentrated to give a solid. The obtained solid was dissolved in toluene, and the solution was purified by silica gel column chromatography. In the column chromatography, as developing solvents, toluene was used first and a mixed solvent (toluene:ethyl acetate=1:4) was used next. An obtained fraction was concentrated to give a solid. The obtained solid was recrystallized with a mixed solvent of chloroform and hexane, whereby 0.85 g of 4-(9H-carbazol-9-yl)-4'-(3,5-diphenyl-4H-1,2,4-triazol-4-yl)triphenylamine (abbreviation: YGATAZ2), which was the object of the synthesis, was obtained in a yield of 64% (synthesis scheme (b-5)).

(b-5)

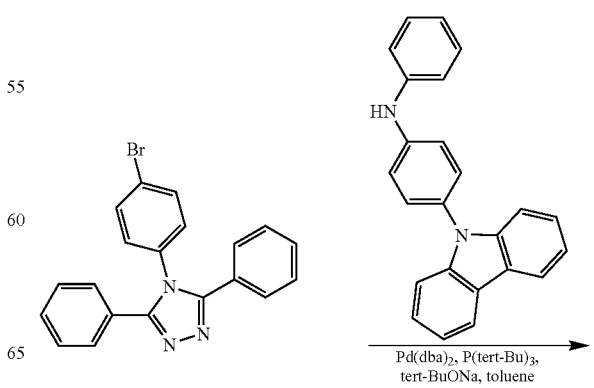

-continued

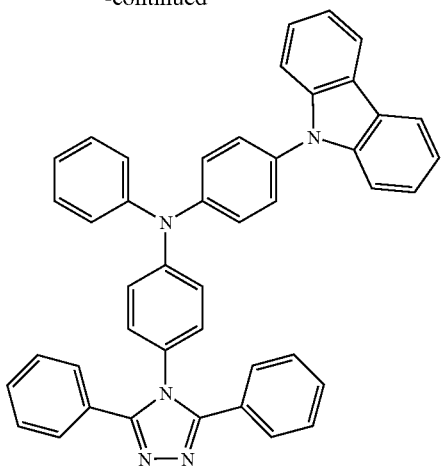

Sublimation purification of 0.85 g of the obtained white solid was performed by a train sublimation method. In the sublimation purification, with a reduced pressure of 7.0 Pa and an argon flow rate of 3 mL/min, the white powder was heated at 310° C. for 15 hours, whereby 0.75 g of a resulting substance was obtained in a yield of 88%.

Figure 11A:
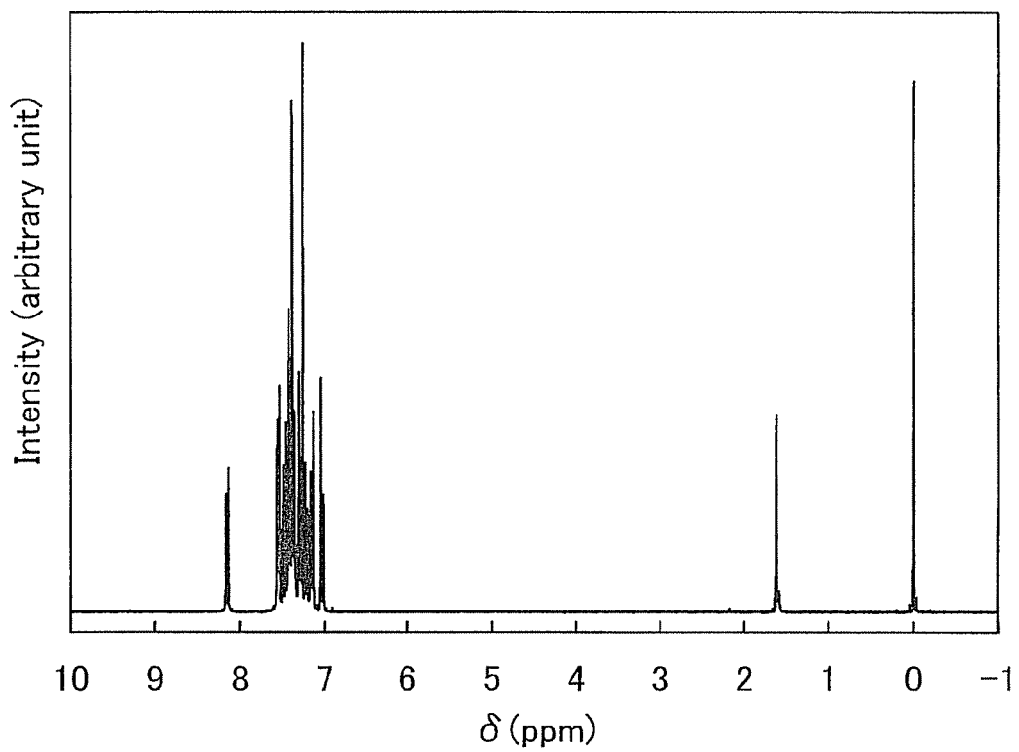
FIGS. 11A and 11B show $^1$H NMR charts of YGATAZ2.
Figure 11B:
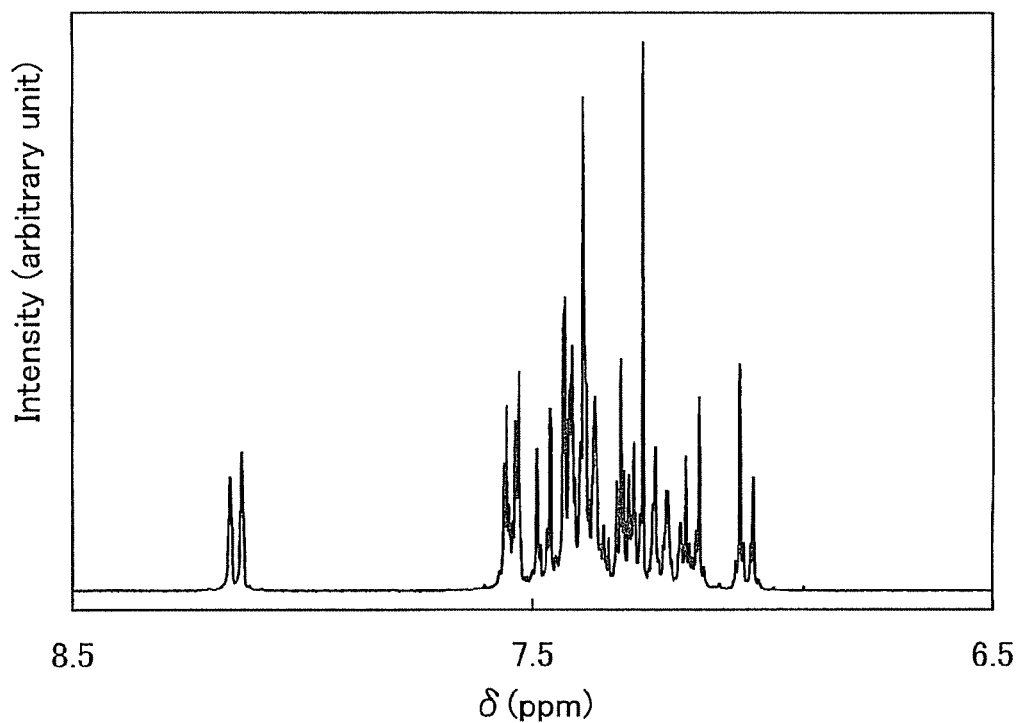

Note that the solid obtained by the above Step 2 was measured by $^1$H NMR. The measurement data are given below. In addition, FIGS. 11A and 11B show $^1$H NMR charts. Note that FIG. 11B is a chart showing an enlarged view of the range of the range of 6.5 ppm to 8.5 ppm in FIG. 11A.

$^1$H NMR (CDCl$_3$, 300 MHz): δ=7.03 (d, J=9.3 Hz, 2H), 7.11-7.59 (m, 27H), 8.15 (d, J=7.8 Hz, 2H).

Figure 12A:
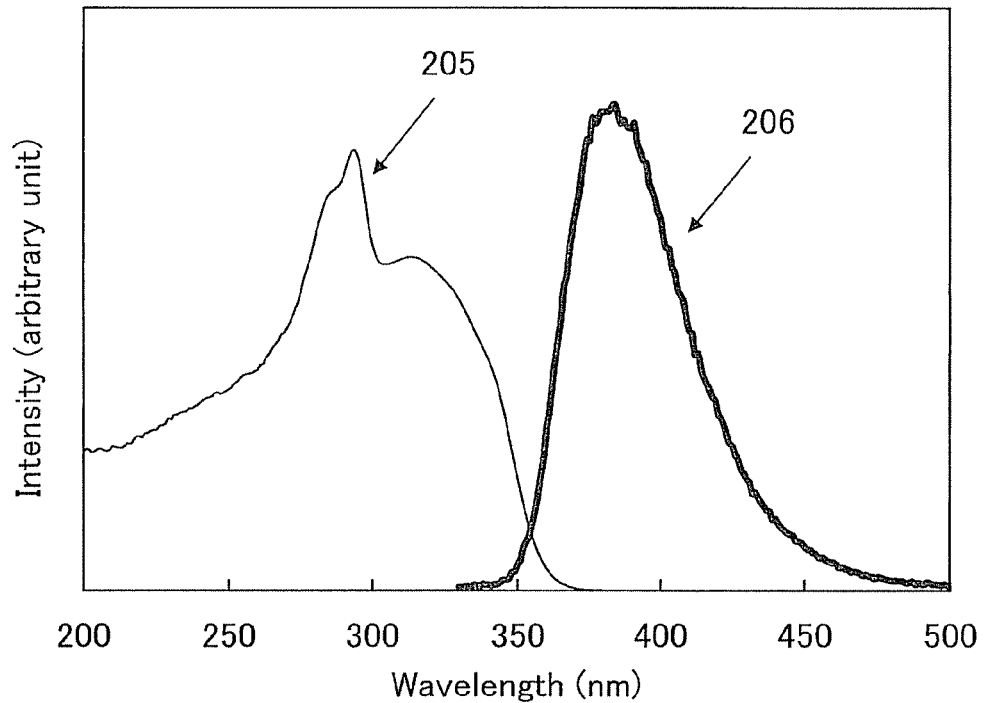
FIGS. 12A and 12B show the absorption spectrum and emission spectrum of YGATAZ2.
Figure 12B:
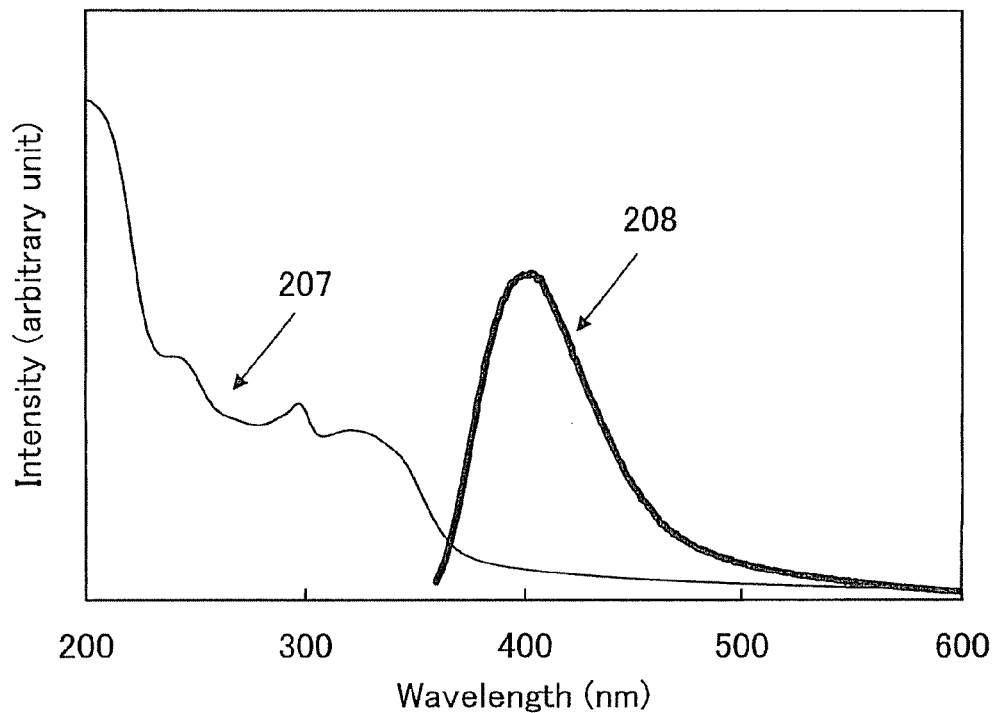

Further, FIG. 12A shows the absorption spectrum 205 and emission spectrum 206 of a toluene solution of YGATAZ2. Furthermore, FIG. 12B shows the absorption spectrum 207 and emission spectrum 208 of the thin film of YGATAZ2. For the measurements, an ultraviolet-visible light spectrophotometer (V-550, manufactured by JASCO Corporation) was used. The solution was put into a quartz cell to form one sample, and YGATAZ2 was evaporated over a quartz substrate to form a thin film as another sample. FIGS. 12A and 12B show the absorption spectra of the solution and the thin film, from each of which the absorption spectrum of quartz was subtracted. In FIGS. 12A and 12B, the horizontal axis represents wavelength (nm), and the vertical axis represents intensity (arbitrary unit). In the case of the toluene solution of YGATAZ2, the absorption was observed at around 314 nm and the maximum emission wavelength was 384 nm (excitation wavelength: 327 nm). Further, in the case of the thin film of YGATAZ2, the absorption was observed at around 321 nm and the maximum emission wavelength was 403 nm (excitation wavelength: 345 nm). Note that the wavelength of each absorption spectrum indicated the wavelength of the peak at the longest wavelength.

Moreover, as a result of measurements with a photoelectron spectrometer (AC-2 photoelectron spectrometer manufactured by Riken Keiki, Co., Ltd.) in the atmosphere, the ionized potential of the thin film of YGATAZ2 was 5.48 eV. Accordingly, it was understood that the HOMO level was −5.48 eV. Furthermore, with the use of the absorption spectrum data of the thin film of YGATAZ2, the absorption edge was obtained by a Tauc plot assuming direct transition. The absorption edge was estimated as an optical energy gap, whereby the energy gap was 3.40 eV. From the obtained values of the energy gap and HOMO level, the LUMO level was −2.08 eV.

Thus, it was understood that YGATAZ2 is a substance having high singlet excitation energy (band gap).

Further, the optimal molecular structure of the ground state of YGATAZ2 was estimated by B3LYP/6-311 (d, p) of density functional theory (DFT). DFT was applied to the present calculation because the accuracy of calculation is higher than that of the Hartree-Fock (HF) method, which does not consider electron correlation, and calculation costs are lower than those of a Moller Plesset (MP) perturbation method, which has the same level of accuracy of calculation as DFT. The calculations were performed with a high performance computer (HPC) (Altix 3700 DX manufactured by SGI). By applying B3LYP/6-311 (d, p) of time-dependent density functional theory (TDDFT) to the molecular structure which was structurally optimized by DFT, the triplet excitation energy of YGATAZ2 was calculated to be 2.98 eV, which corresponds to 416.4 nm when being converted into wavelength. From the above results, it was understood that the triazole derivative of the present invention is a substance having high excitation energy. In particular, it was understood that the triazole derivative of the present invention is a substance having high triplet excitation energy.

Example 2

Figure 13:
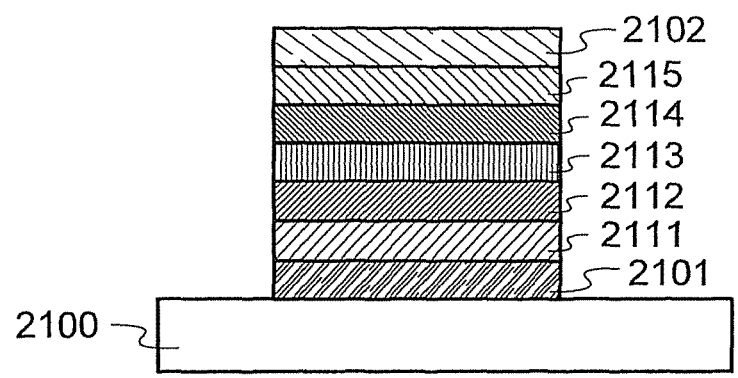
FIG. 13 illustrates a light-emitting element of Example 2.

In this example, the light-emitting elements of the present invention are described using FIG. 13. Chemical formulae of materials used in this example are illustrated below.

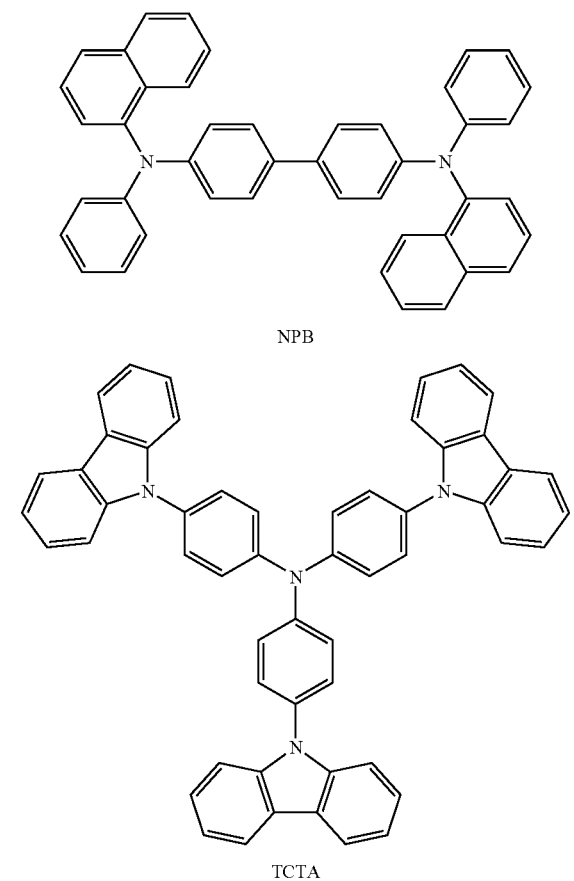

NPB

TCTA

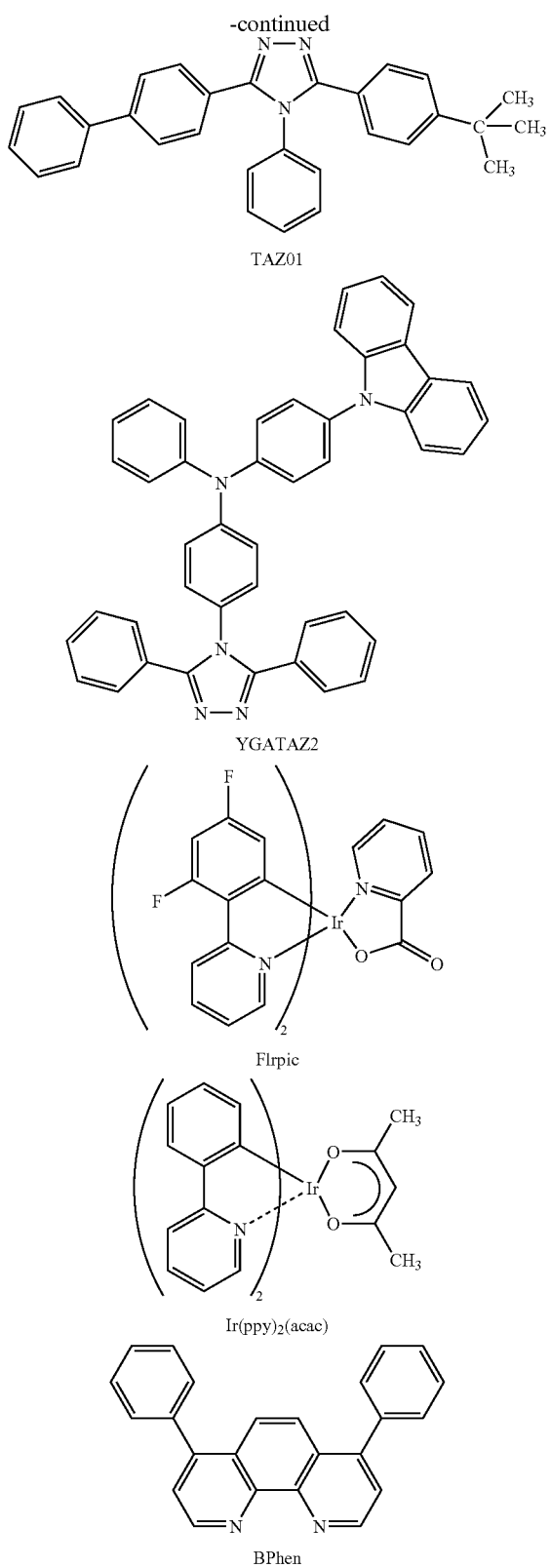

TAZ01

YGATAZ2

FIrpic

Ir(ppy)$_2$(acac)

BPhen

Methods of manufacturing the light-emitting elements of this example are described below.

(Light-Emitting Element 1)

First, a film of indium tin oxide containing silicon oxide was formed over a glass substrate 2100 by a sputtering method to form a first electrode 2101. Note that the thickness of the first electrode 2101 was set to be 110 nm and that the area of the electrode was set to be 2 mm by 2 mm.

Next, the substrate having the first electrode was fixed to a substrate holder provided in a vacuum evaporation apparatus in such a way that a surface of the substrate, on which the first electrode was formed, faced downward, and then the pressure was reduced to about $10^{-4}$ Pa. Then, 4,4'-bis[N-(1-naphthyl)-N-phenylamino]biphenyl (abbreviation: NPB) and molybdenum(VI) oxide were co-evaporated over the first electrode 2101, whereby a layer 2111 containing a composite material of an organic compound and an inorganic compound was formed. The thickness of the layer 2111 was set to be 40 nm and the weight ratio of NPB to molybdenum(VI) oxide was adjusted so to be 4:1 (=NPB:molybdenum oxide). Note that the co-evaporation method is an evaporation method in which evaporation is performed from a plurality of evaporation sources at the same time in one treatment chamber.

Next, a film of 4,4',4''-tris(carbazol-9-yl)triphenylamine (abbreviation: TCTA) was formed over the layer 2111 containing a composite material to a thickness of 20 nm by an evaporation method using resistance heating to form a hole-transporting layer 2112.

Furthermore, YGATAZ2, which is the triazole derivative of the present invention synthesized in Synthesis Example 2 of Example 1, and bis[2-(4',6'-difluorophenyl)pyridinato-N,C$^{2'}$] iridium(III)picolinate (abbreviation: FIrpic) were co-evaporated, whereby a 30-nm-thick light-emitting layer 2113 was formed over the hole-transporting layer 2112. Here, the weight ratio of YGATAZ2 to FIrpic was adjusted so as to be 1:0.05 (=YGATAZ2:FIrpic).

Then, a film of 3-(4-biphenylyl)-4-phenyl-5-(4-tert-butylphenyl)-1,2,4-triazole (abbreviation: TAZ01) was formed over the light-emitting layer 2113 to a thickness of nm by an evaporation method using resistance heating to form an electron-transporting layer 2114.

Furthermore, bathophenanthroline (abbreviation: BPhen) and lithium were co-evaporated over the electron-transporting layer 2114, whereby a 20-nm-thick electron-injecting layer 2115 was formed. Here, the weight ratio of BPhen to lithium was adjusted so as to be 1:0.01 (=BPhen:lithium).

Lastly, a film of aluminum was formed over the electron-injecting layer 2115 to a thickness of 200 nm by an evaporation method using resistance heating to form a second electrode 2102. Thus, a light-emitting element 1 was manufactured.

Figure 14:
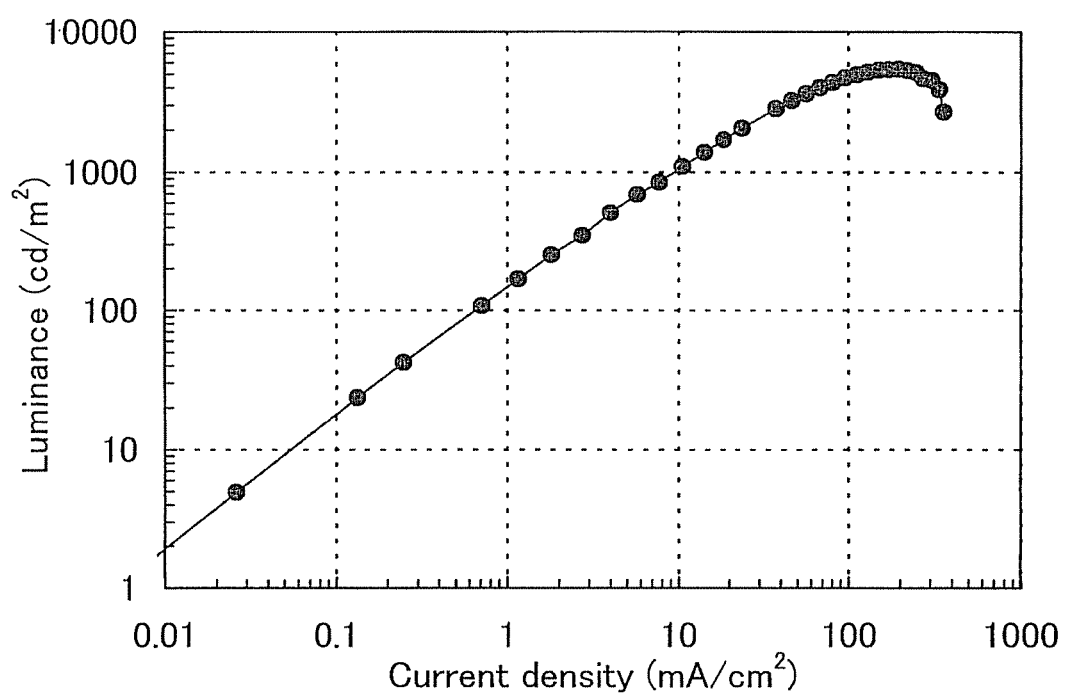
FIG. 14 shows the current density vs. luminance characteristic of a light-emitting element manufactured in Example 2.
Figure 15:
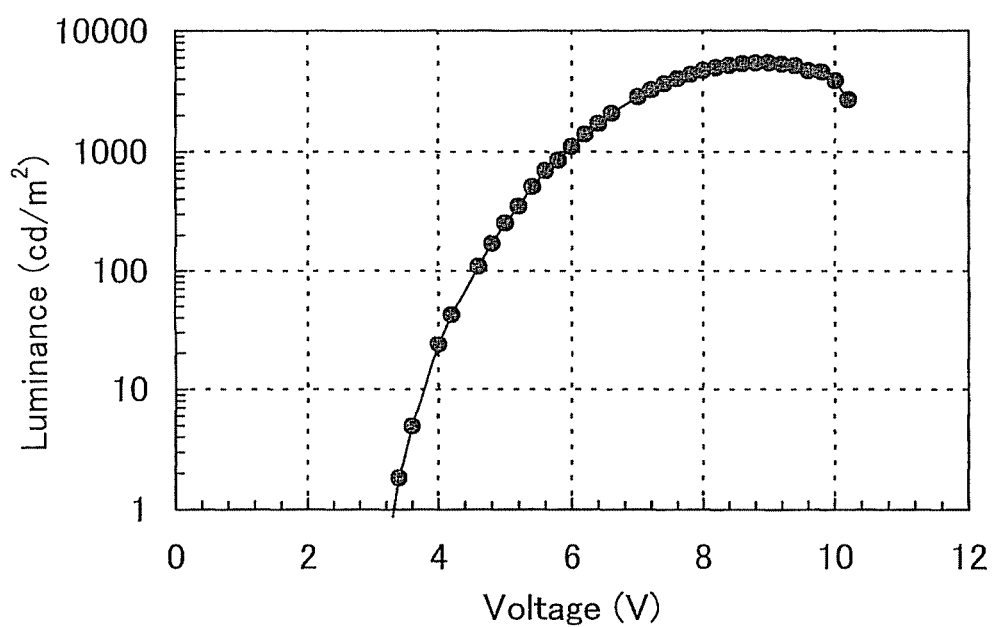
FIG. 15 shows the voltage vs. luminance characteristic of the light-emitting element manufactured in Example 2.
Figure 16:
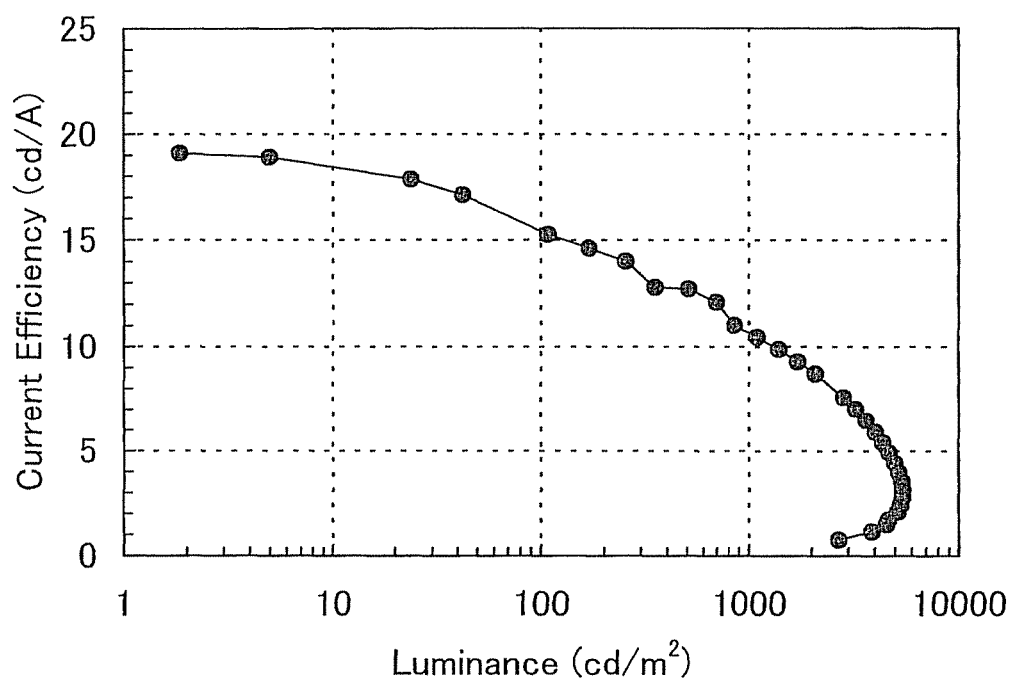
FIG. 16 shows the luminance vs. current density characteristic of the light-emitting element manufactured in Example 2.
Figure 17:
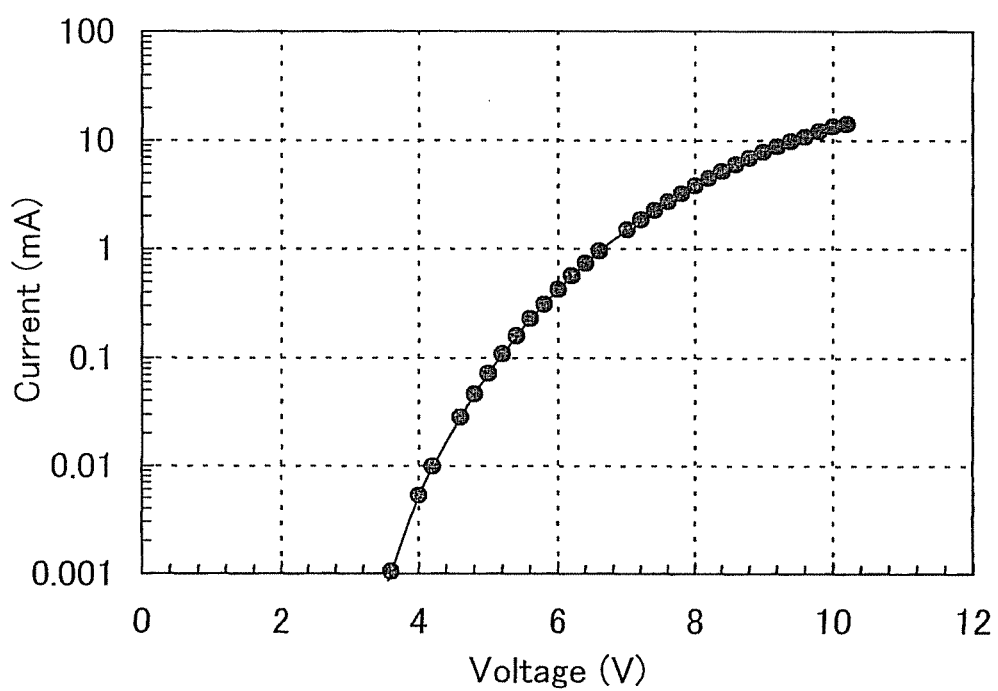
FIG. 17 shows the voltage vs. current characteristic of the light-emitting element manufactured in Example 2.
Figure 18:
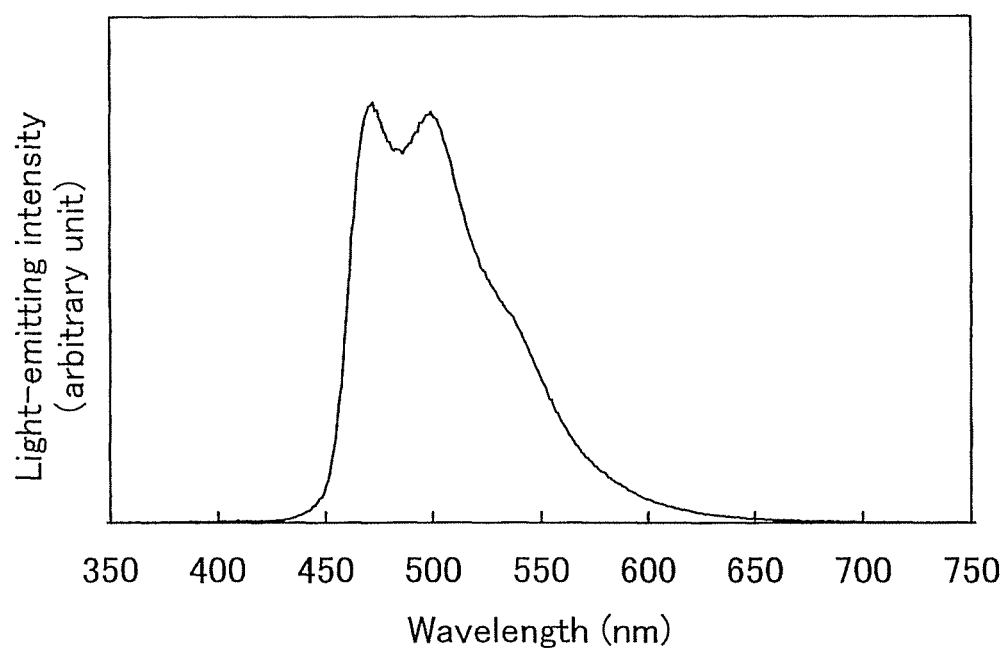
FIG. 18 shows the emission spectrum of the light-emitting element manufactured in Example 2.

FIG. 14 shows the current density vs. luminance characteristic of the light-emitting element 1. Further, FIG. 15 shows the voltage vs. luminance characteristic of the light-emitting element 1. Further, FIG. 16 shows the luminance vs. current efficiency characteristic of the light-emitting element 1. Further, FIG. 17 shows the voltage vs. current characteristic of the light-emitting element 1. Further, FIG. 18 shows the emission spectrum at a current of 1 mA of the light-emitting element 1. The CIE chromaticity coordinates of the light-emitting element 1 at a luminance of 1000 cd/m$^2$ were (x, y)=(0.18, 0.38). As an emission color of the light-emitting element 1, blue light emission due to FIrpic, which was a guest material, was obtained.

(Light-Emitting Element 2)

For a light-emitting element 2, bis(2-phenylpyridinato-N, C$^{2'}$)iridium(III)acetylacetonate (abbreviation: Ir(Ppy)$_2$ (acac)), instead of FIrpic in the light-emitting layer 2113 of the light-emitting element 1, and YGATAZ2 were co-evaporated over the hole-transporting layer 2112 to form the 30-nm-thick light-emitting layer 2113. Here, the weight ratio of YGATAZ2 to Ir(Ppy)$_2$(acac) was adjusted so as to be 1:0.05

(=YGATAZ2:Ir(ppy)$_2$(acac)). In addition, the light-emitting element 2 was manufactured in a similar manner to the light-emitting element 1 except that the 10-nm-thick electron-transporting layer 2114 was formed over the light-emitting layer 2113 by using BPhen instead of TAZ01.

Figure 19:
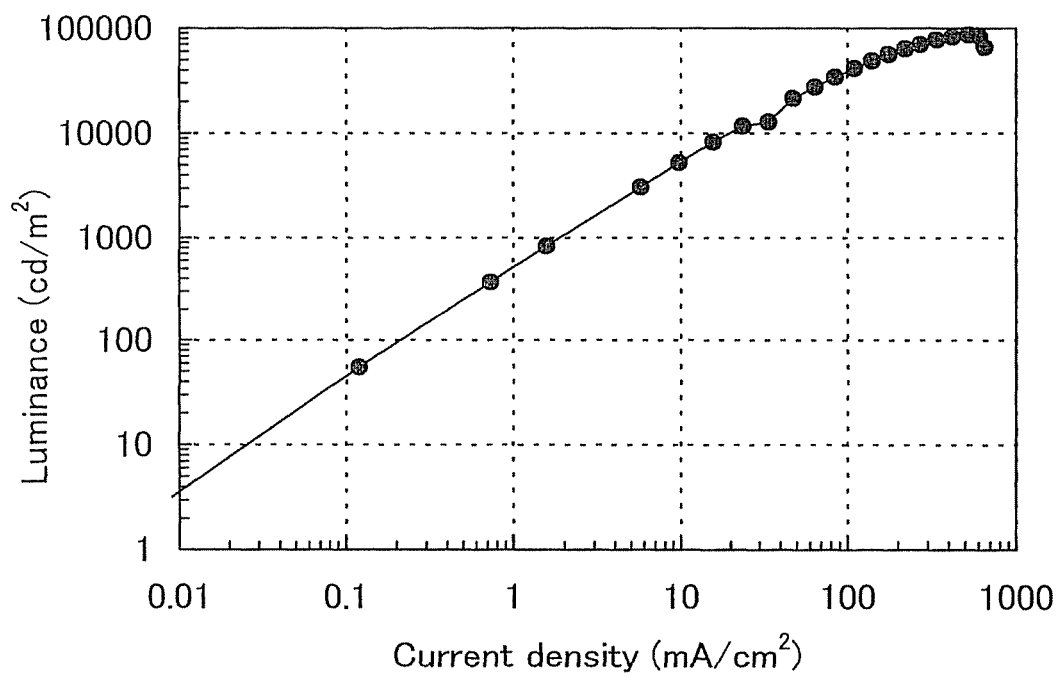
FIG. 19 shows the current density vs. luminance characteristic of a light-emitting element manufactured in Example 2.
Figure 20:
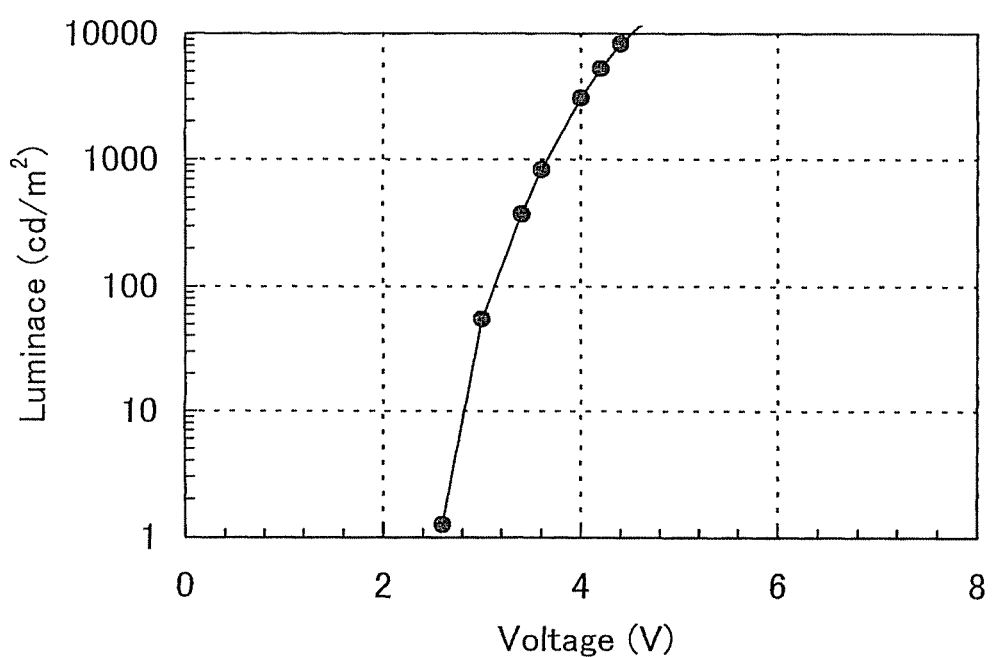
FIG. 20 shows the voltage vs. luminance characteristic of the light-emitting element manufactured in Example 2.
Figure 21:
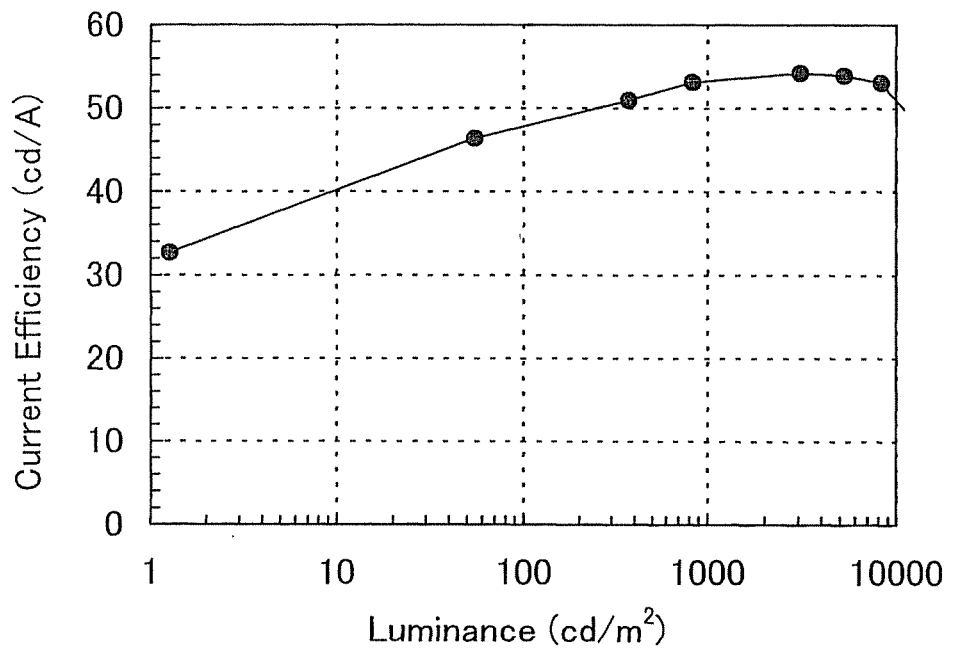
FIG. 21 shows the luminance vs. current density characteristic of the light-emitting element manufactured in Example 2.
Figure 22:
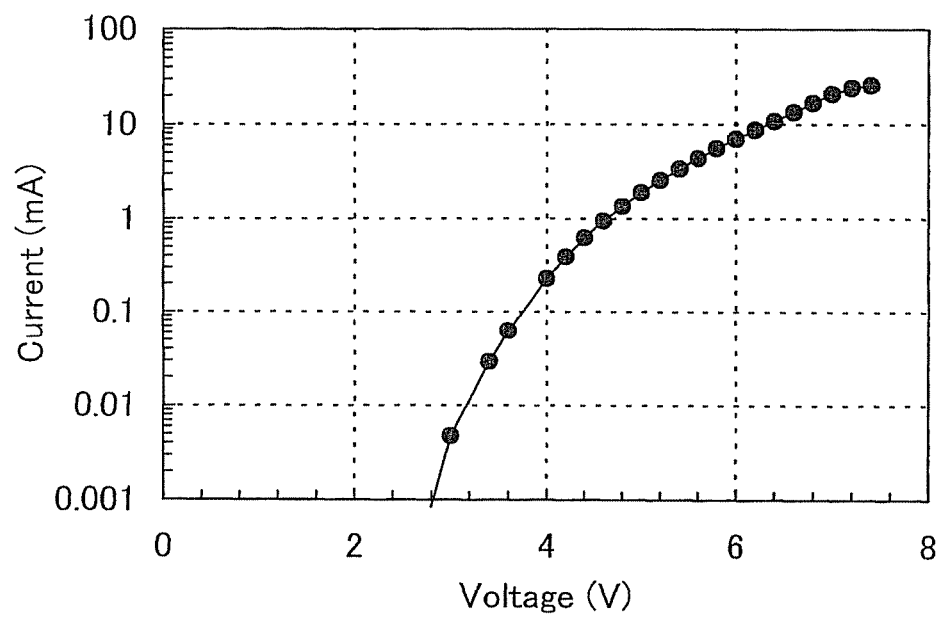
FIG. 22 shows the voltage vs. current characteristic of the light-emitting element manufactured in Example 2.
Figure 23:
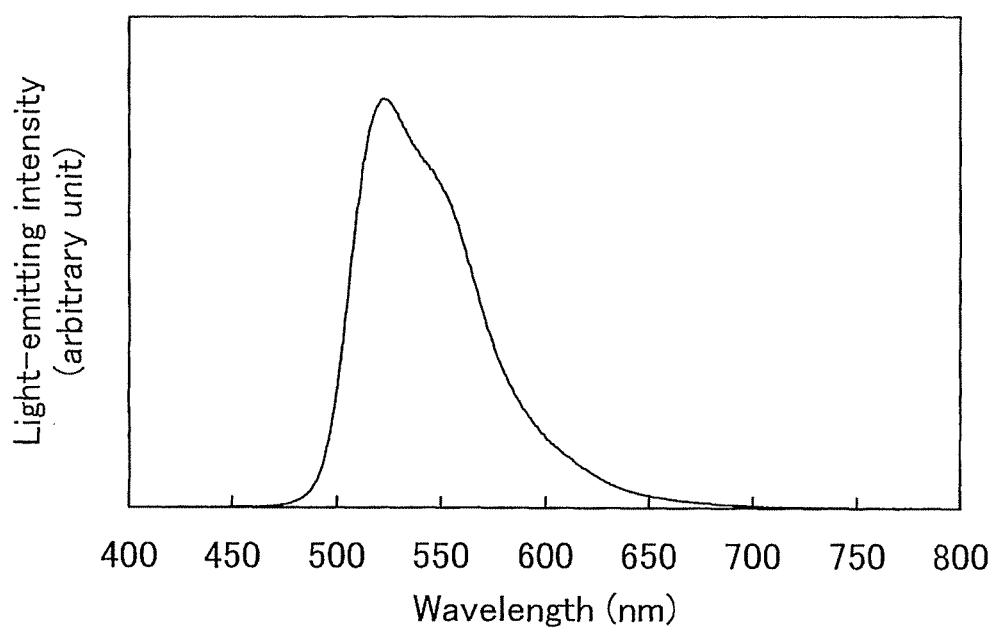
FIG. 23 shows the emission spectrum of the light-emitting element manufactured in Example 2.

FIG. 19 shows the current density vs. luminance characteristic of the light-emitting element 2. Further, FIG. 20 shows the voltage vs. luminance characteristic of the light-emitting element 2. Further, FIG. 21 shows the luminance vs. current efficiency characteristic of the light-emitting element 2. Further, FIG. 22 shows the voltage vs. current characteristic of the light-emitting element 2. Further, FIG. 23 shows the emission spectrum at a current of 1 mA of the light-emitting element 2. The CIE chromaticity coordinates of the light-emitting element 2 at a luminance of 1000 cd/m$^2$ were (x, y)=(0.31, 0.65). As an emission color of the light-emitting element 2, blue light emission due to Ir(Ppy)$_2$(acac), which was a guest material, was obtained.

Accordingly, it is understood that by manufacturing a light-emitting element using the triazole derivative of the present invention as a host material of a light-emitting layer and a phosphorescent compound as a guest material, a light-emitting element that emits light with high efficiency at low driving voltage can be obtained. Thus, it is understood that by implementing the present invention, a light-emitting element with less power consumption can be obtained.

The present application is based on Japanese Patent Application serial No. 2007-330608 filed with Japan Patent Office on Dec. 21, 2007, the entire contents of which are hereby incorporated by reference.

EXPLANATION OF REFERENCE

100: substrate, 101: first electrode, 102: second electrode, 103: layer containing organic compound, 111: hole-injecting layer, 112: hole-transporting layer, 113: light-emitting layer, 114: electron-transporting layer, 115: electron-injecting layer.

401: driver circuit (source-side driver circuit), 402: pixel portion, 403: driver circuit (gate-side driver circuit), 404: sealing substrate, 405: sealing material, 407: space, 408: wiring, 409: flexible printed circuit (FPC), 410: element substrate, 411: switching TFT, 412: current-controlling TFT, 413: first electrode, 414: insulator, 416: layer containing organic compound, 417: second electrode, 418: light-emitting element, 423: n-channel TFT, 424: p-channel

501: first electrode, 502: second electrode, 511: first light-emitting unit, 512: second light-emitting unit, 513: charge generation layer.

901: chassis, 902: liquid crystal layer, 903: backlight, 904: chassis, 905: driver IC, 906: terminal, 951: substrate, 952: electrode, 953: insulating layer, 954: partition layer, 955: EL layer, 956: electrode.

2001: chassis, 2002: light source, 2100: glass substrate, 2101: first electrode, 2102: second electrode, 2111: layer containing composite material, 2112: hole-transporting layer, 2113: light-emitting layer, 2114: electron-transporting layer, 2115: electron-injecting layer.

3001: lighting apparatus, 3002: television set.

9101: chassis, 9102: supporting base, 9103: display portion, 9104: speaker portion, 9105: video input terminal, 9201: main body, 9202: chassis, 9203: display portion, 9204: keyboard, 9205: external connection port, 9206: pointing device, 9401: main body, 9402: chassis, 9403: display portion, 9404: audio input portion, 9405: audio output portion, 9406: operation key, 9407: external connection port, 9408: antenna, 9501: main body, 9502: display portion, 9503: chassis, 9504: external connection port, 9505: remote control receiving portion, 9506: image receiving portion, 9507: battery, 9508: audio input portion, 9509: operation key, 9510: eye piece portion.

The invention claimed is:

1. A light-emitting element comprising:
a light-emitting layer between a pair of electrodes,
wherein the light-emitting layer comprises a triazole derivative and a substance which emits blue phosphorescence,
wherein the triazole derivative is represented by a formula (G9);

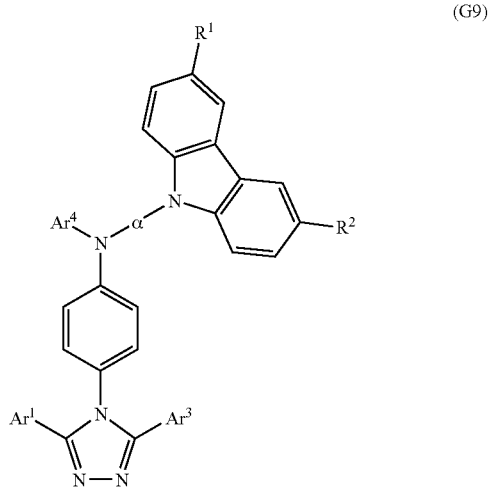

(G9)

wherein Ar$^1$, Ar$^3$, and Ar$^4$ represent an aryl group,
wherein α represents an unsubstituted phenylene group,
wherein R$^1$ and R$^2$ each represent hydrogen or an alkyl group having 1 to 4 carbon atoms, and
wherein the aryl group is selected from an unsubstituted phenyl group, an o-tolyl group, a m-tolyl group, and a p-tolyl group.

2. The light-emitting element according to claim 1, wherein the substance is represented by the following formula:

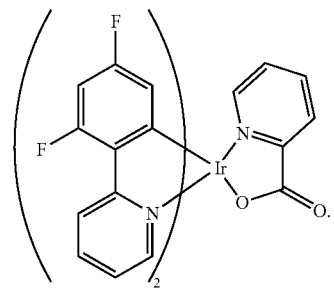

3. An electronic device comprising a display portion, wherein the display portion comprises the light-emitting element according to claim 1.

4. The light-emitting element according to claim 1, wherein the aryl group is an unsubstituted phenyl group.

5. The light-emitting element according to claim 1, wherein the triazole derivative is represented by the following formula:

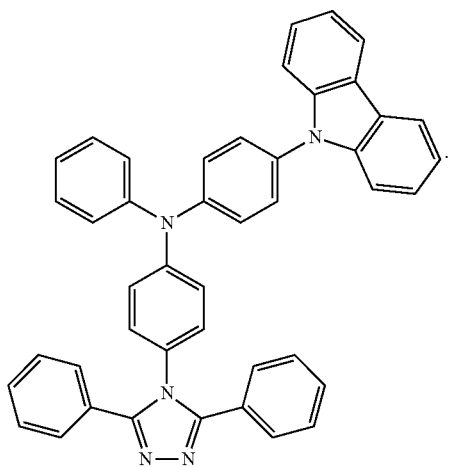 [SMILES: c1ccc(-c2nnc(-c3ccccc3)n2-c2ccc(N(c3ccccc3)c3ccc(-n4c5ccccc5c5ccccc54)cc3)cc2)cc1]

6. A lighting apparatus comprising the light-emitting element according to claim 1.

7. A light-emitting element comprising:
a light-emitting layer between a pair of electrodes,
wherein the light-emitting layer comprises a triazole derivative and a substance which emits blue phosphorescence,
wherein the triazole derivative is represented by a formula (G4);

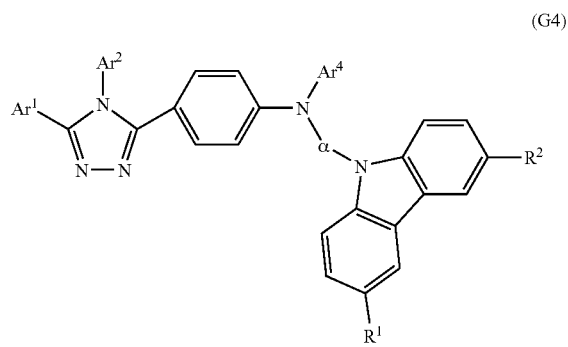

wherein $Ar^1$, $Ar^2$, and $Ar^4$ represent an aryl group,
wherein α represents an unsubstituted phenyl group, and
wherein $R^1$ and $R^2$ each represent hydrogen or an alkyl group having 1 to 4 carbon atoms.

8. The light-emitting element according to claim 7, wherein the substance is represented by the following formula:

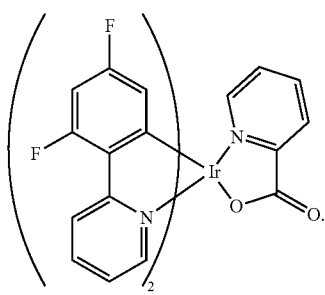

9. An electronic device comprising a display portion,
wherein the display portion comprises the light-emitting element according to claim 7.

10. The light-emitting element according to claim 7, wherein the aryl group is an unsubstituted phenyl group.

11. The light-emitting element according to claim 7, wherein the triazole derivative is represented by the following formula:

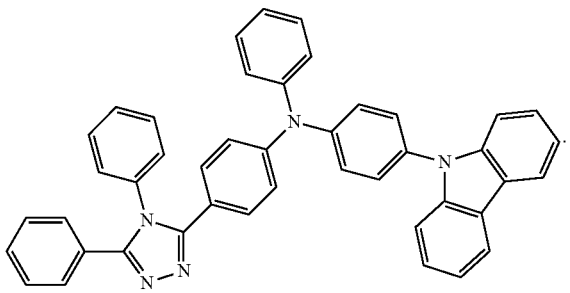 [SMILES: c1ccc(-c2nnc(-c3ccc(N(c4ccccc4)c4ccc(-n5c6ccccc6c6ccccc65)cc4)cc3)n2-c2ccccc2)cc1]

12. A lighting apparatus comprising the light-emitting element according to claim 7.

* * * * *